(12) United States Patent
Grand et al.

(10) Patent No.: US 11,560,597 B2
(45) Date of Patent: Jan. 24, 2023

(54) APPLICATION OF EPIGENETIC CHROMOSOMAL INTERACTIONS IN CANCER DIAGNOSTICS

(71) Applicant: Oxford BioDynamics, PLC, Oxford (GB)

(72) Inventors: Francis Hector Grand, Oxford (GB); Aroul Selvam Ramadass, Oxford (GB); Alexandre Akoulitchev, Oxford (GB); Ewan Hunter, Oxford (GB)

(73) Assignee: Oxford BioDynamics, PLC, Oxford (GB)

( * ) Notice: Subject to any disclaimer, the term of this patent is extended or adjusted under 35 U.S.C. 154(b) by 635 days.

(21) Appl. No.: 16/465,133

(22) PCT Filed: Nov. 30, 2017

(86) PCT No.: PCT/GB2017/053615
§ 371 (c)(1),
(2) Date: May 29, 2019

(87) PCT Pub. No.: WO2018/100381
PCT Pub. Date: Jun. 7, 2018

(65) Prior Publication Data
US 2019/0338367 A1 Nov. 7, 2019

Related U.S. Application Data

(60) Provisional application No. 62/428,893, filed on Dec. 1, 2016.

(51) Int. Cl.
*C12Q 1/6886* (2018.01)
*C12Q 1/6827* (2018.01)

(52) U.S. Cl.
CPC ......... *C12Q 1/6886* (2013.01); *C12Q 1/6827* (2013.01); *C12Q 2521/301* (2013.01); *C12Q 2521/501* (2013.01); *C12Q 2523/101* (2013.01); *C12Q 2565/501* (2013.01)

(58) Field of Classification Search
CPC ..... C12Q 1/6886; C12Q 1/6827; A61P 35/00; A61P 43/00
See application file for complete search history.

(56) References Cited

U.S. PATENT DOCUMENTS

2009/0117076 A1* 5/2009 Chen .................... A61K 38/212
424/85.7

FOREIGN PATENT DOCUMENTS

| WO | 2007004057 | | 1/2007 | |
|---|---|---|---|---|
| WO | 2007093819 | | 8/2007 | |
| WO | 2008084405 | A3 | 7/2008 | |
| WO | 2009147386 | A1 | 12/2009 | |
| WO | 2010036323 | A1 | 4/2010 | |
| WO | 2012005595 | A2 | 1/2012 | |
| WO | WO-2012159025 | A2 * | 11/2012 | .......... C12Q 1/6869 |
| WO | 2016207647 | | 12/2016 | |
| WO | 2016207653 | | 12/2016 | |
| WO | 2016207661 | | 12/2016 | |
| WO | WO-2016207647 | A1 * | 12/2016 | ............. G16H 50/70 |
| WO | 2017106290 | | 6/2017 | |
| WO | 2017191477 | | 11/2017 | |

OTHER PUBLICATIONS

Mukhopadhyay et al, Formation of distinct chromatin conformation signatures epigenetically CrossMark regulate macrophage activation, 2014, International Immunopharmacology, 18, 7-11 (Year: 2014).*
Jakub et al, A pilot study of chromosomal aberrations and epigenetic changes in peripheral blood samples to identify patients with melanoma, 2015,1-6 (Year: 2015).*
Wang et al, The Properties of Genome Conformation and Spatial Gene Interaction and Regulation Networks of Normal and Malignant Human Cell Types, 2013, PLOS ONE, 8, e58793, pp. 1-13 (Year: 2013).*
Garland et al, Chromatin Conformation Signatures Associated with Epigenetic Deregulation of the FIP1L1 and PDGFRA Genes, 602. Disordered Gene Expression in Hematologic Malignancy, Including Disordered Epigenetic Regulation: Poster I | Dec. 2, 2016 (post art), pp. 1-3 (Year: 2016).*
Belton et al, Chromosome Conformation Capture Carbon Copy (5C) in Budding Yeast, 2015, Cold Spring Harb Protoc; doi:10. 1101/pdb.prot085191, pp. 593-598 (Year: 2015).*
Fang et al, Mapping of long-range chromatin interactions by proximity ligation-assisted ChIP-seqCell Research, (2016) 26:1345-1348. published on line Nov. 25, 2016. (Year: 2016).*
Crutchley, et al., "Chromatin conformation signatures: ideal human disease biomarkers?", Biomarkers in Medicine, (Aug. 1, 2010), vol. 4, No. 4, doi:10.2217/bmm.10.68, ISSN 1752-0363, pp. 611-629.
Flavahan et al, "Insulator dysfunction and oncogene activation in IDH mutant gliomas", Nature. Jan. 7, 2016; 529(7584): 110-114. doi:10.1038/nature16490.
Grand, et al., "Chromatin Conformation Signatures Associated with Epigenetic Deregulation of the FIP1L1 and PDGFRA Genes" Blood (2016) 128 (22) : 1525 (602. Disordered Gene Expression In Hematologic Malignancy, Including Disordered Epigenetic Regulation: Poster I | Dec. 2, 2016).
Kolovos, et al., "Targeted Chromatin Capture (T2C): a novel high resolution high throughput method to detect genomic interactions and regulatory elements", Epigenetics & Chromatin, Biomed Central Ltd, London, UK, (Jun. 16, 2014), vol. 7, No. 1, doi:10.1186/ 1756-8935-7-10, ISSN 1756-8935, p. 10.
Oxford BioDynamics Announcement of Jun. 13, 2017.
Rao, et al., "A three-dimensional map of the human genome at kilobase resolution reveals principles of chromatin looping", Cell. Dec. 18, 2014; 159(7): 1665-1680. doi:10.1016/j.cell.2014.11.021.

(Continued)

Primary Examiner — Narayan K Bhat
(74) Attorney, Agent, or Firm — FisherBroyles, LLP; Victoria L. Boyd; Adelaide K. Leitzel

(57) ABSTRACT

The invention provides a method of determining the epigenetic chromosome interactions which are relevant to a prognostic companion epigenetic test for cancer.

6 Claims, 9 Drawing Sheets

Specification includes a Sequence Listing.

(56) References Cited

OTHER PUBLICATIONS

Sandhu, et al., "Chromatin interaction networks and higher order architectures of eukaryotic genomes", Journal of Cellular Biochemistry, US, (Aug. 18, 2011), vol. 112, No. 9, doi:10.1002/jcb.23155, ISSN 0730-2312, pp. 2218-2221.

Zhao, et al., "Circular chromosome conformation capture (4C) uncovers extensive networks of epigenetically regulated intra- and interchromosomal interactions", Nature Genetics, Nature Publishing Group, New York, US, (Nov. 1, 2006), vol. 38, No. 11, doi:10.1038/NG1891, ISSN 1061-4036, pp. 1341-1347.

Chromatin Conformation Signatures Associated with Epigenetic Deregulation of the FIP1L1 and PDGFRA Genes. Abstract presented at the American Society for Haematology (ASH) conference in San Diego on Dec. 3-6, 2016.

EpiSwitchTM MIQE-Compliant Detection of a FIP1L1-PDGFRA 3C interaction in Idiopathic Hypereosinophillic Syndrome (IHES) and Glioma Patients. Presented at the American Society for Haematology (ASH) conference in San Diego on Dec. 3-6, 2016.

Chromatin Conformation Signatures Associated with Epigenetic Deregulation of the FIP1L1 and PDGFRA Genes. Poste presented at the American Society for Haematology (ASH) conference in San Diego on Dec. 3-6, 2016.

\* cited by examiner

SEQUENCE LISTING

```
<160> NUMBER OF SEQ ID NOS: 72

<210> SEQ ID NO 1
<211> LENGTH: 501
<212> TYPE: DNA
<213> ORGANISM: Homo sapiens

<400> SEQUENCE: 1
ttccacgtgg cctaccacag catgtcaggc ctggggcag aatcttgcca tactgtgcag      60
cccaaatttg aatgccaaag gctttcgttt gtctctgggg ggccacagtc taggtctagt    120
tctgtgcagg agttgtaata tttgctcttc tctccctcct ccagctcgca gacctctgaa    180
gagagtgcca ttgagacggg ttccagcagt tccaccttca tcaagagaga ggacgagacc    240
attgaagaca tcgaaaagat aaaacaggtg ttagtgagga tatggggaaa taaaaccctc    300
atacacttct ggtgggattg taaaatggtg cagctgcttt gaagaacagc ctggccattt    360
tctcaaatgg tgaaacatgg agttaccatg tgagtcctcc accttagagg aatgaaaaca    420
tattcagaca aaaacttgta cgtgaatatt catagcagca ttattcttaa tagaaagtgg    480
aaaaagaaaa cctcgcagct g                                              501

<210> SEQ ID NO 2
<211> LENGTH: 647
<212> TYPE: DNA
<213> ORGANISM: Homo sapiens

<400> SEQUENCE: 2
tgggagtggg tggagtgaga acctgggaga aggccagccc tttatatcca ggcagacagc     60
tccaagtgcc accatggatc agccagtctt gcaggggtga tgctattcag ctacagatgg    120
cttgatcctg agtcatttct tccttttcca tgcagtgtgt ccaccgtgat ctggctgctc    180
gcaacgtcct cctggcacaa ggaaaaattg tgaagatctg tgactttggc ctggccagag    240
acatcatgca tgattcgaaa agataaaaca ggtgttagtg aggatatggg gaaataaaac    300
cctcatacac ttctggtggg attgtaaaat ggtgcagctg ctttgaagaa cagcctggcc    360
attttctcaa atggtgaaac atggagttac catgtgagtc ctcaccttag aggaatgaa    420 aacatattca gacaaaaact tgtacgtgaa tattcatagc agcattattc ttaatagaaa    480
gtggaaaaag aaaacctcgc agctgcatca actgatgaat ggatagatta aatgtgttat    540
atccatacag cggaatatta tttggcaagg acaataaaat gaagtactgg tagatgttac    600
aacacggatg aaccttacaa atgtggaagc taaagatgtc agtccgt                   647

<210> SEQ ID NO 3
<211> LENGTH: 462
<212> TYPE: DNA
<213> ORGANISM: Homo sapiens

<400> SEQUENCE: 3
gcagctgcga ggttttcttt ttccactttc tattaagaat aatgctgcta tgaatattca     60
```

```
cgtacaagtt tttgtctgaa tatgttttca ttcctctaag gtggaggact cacatggtaa    120
ctccatgttt caccatttga gaaaatggcc aggctgttct tcaaagcagc tgcaccattt    180
tacaatccca ccagaagtgt atgagggttt tatttcccca tatcctcact aacacctgtt    240 ttatctttc gaggtccttg ctgaacctgg acctataaat gacgtcaatg atagtgatcc     300
ctactgcaga atctacaag tggctataaa gaactctgta ggtaagaaat tctgtaagat     360
cagaaagtac aatgaattca cttcataata aattacttgg tggacaccaa atgggtgcta    420
aattgattgg gtagaaggaa ttgtatgccc aagccacatg gc                      462

<210> SEQ ID NO 4
<211> LENGTH: 499
<212> TYPE: DNA
<213> ORGANISM: Homo sapiens

<400> SEQUENCE: 4
agtacttcct ctcccctccc atattgttaa aaatagttta cattgcttcc caggctgggc     60
tggtggagtt ggcacgagat gtcagaggaa cctgagtcat gctcaggccc aagccctgtt    120
ggcaggcaga ccactgcttt ctggccttcc gtgactatct gaaaaaaatc gtgaatggct    180
agagctactc ttcacttgct gaacattttc aaaaagaatt gagaacttct ggattaaatt    240
gccttcttcc tcgaaaagat aaaacaggtg ttagtgagga tatggggaaa taaaccctc     300 atacacttct ggtgggattg taaaatggtg cagctgcttt gaagaacagc ctggccattt    360
tctcaaatgg tgaaacatgg agttaccatg tgagtcctcc accttagagg aatgaaaaca    420
tattcagaca aaaacttgta cgtgaatatt catagcagca ttattcttaa tagaaagtgg    480
aaaaagaaaa cctcgcagc                                                499

<210> SEQ ID NO 5
<211> LENGTH: 609
<212> TYPE: DNA
<213> ORGANISM: Homo sapiens

<400> SEQUENCE: 5
cctctcccac acaaacctgc tactgagtac cttcgctaac ttaaccattc attcaccctg     60
gaagaccacc tactagcaga aggattctta acaaatgtaa agaaagtaag gactttacac    120
taacaataca aaactaactc tctctttgac aattcaaaaa acaaaagatg ttgaactttg    180
acatttacag aattaaatgt caaatgtgac acaataccat cacatctggc taactaactc    240
ttatgctttt tttagtaagg aacaactttt gagcctcaat atcttaattc ttaaaatgat    300
aaagaacact taactcaatt tgttgagatc aaataaggta atgtaaaagt gggatttta    360 tttttactta tttattcgaa aaccctggga ccctccaga tgggactaac tggggaaagt    420
ggacaagtta caaacaaaga aactcaaagg aaagtcattg cactgatct ctaagatgct    480 atcacatgtg attggtggtt gatttttatta caaattata agcaaagtac tacaaaggtg    540
gctttaaaaa gaaaataaag caattcacag aaactacttt ttcatgtagc ttgtatgtgt    600
gctccatgt                                                           609

<210> SEQ ID NO 6
<211> LENGTH: 586
<212> TYPE: DNA
<213> ORGANISM: Homo sapiens

<400> SEQUENCE: 6
aaatgatgag gcacgggtga ataagatagt tggaagtgac acatacagat ttcaaataat     60
```

-continued

```
tccctaaagg tgtatggttt tctttcccta caaatcctac tttcagttct tttgtacatg      120
gacccagagt ggaattgctg gatcatatga taattctatt tttaacttct tgatggacct      180 ctgttttttgt tttgttttttt acagaggctg caacatttta tattcctact aataatgcac    240
aggggttcgg atttctccac atccttgcca acacttgata tttcctgggt ttttgataa       300 tggccatcct aataggtgtg gggacatgag gttttcaata tgcttgtggg acatcgaaaa      360
ccctgggacc cttccagatg ggactaactg gggaaagtgg acaagttaca aacaaagaaa      420
ctcaaaggaa agtcattggc actgatctct aagatgctat cacatgtgat tggtggttga      480
ttttattaac aaattataag caaagtacta caaaggtggc tttaaaaaga aaataaagca      540
attcacagaa actactttt catgtagctt gtatgtgtgc tccatg                      586
```

<210> SEQ ID NO 7
<211> LENGTH: 20
<212> TYPE: DNA
<213> ORGANISM: Homo sapiens
<400> SEQUENCE: 7

```
ttccacgtgg cctaccacag                                                   20
```

<210> SEQ ID NO 8
<211> LENGTH: 20
<212> TYPE: DNA
<213> ORGANISM: Homo sapiens
<400> SEQUENCE: 8

```
cagctgcgag gttttctttt                                                   20
```

<210> SEQ ID NO 9
<211> LENGTH: 20
<212> TYPE: DNA
<213> ORGANISM: Homo sapiens
<400> SEQUENCE: 9

```
tgggagtggg tggagtgaga                                                   20
```

<210> SEQ ID NO 10
<211> LENGTH: 23
<212> TYPE: DNA
<213> ORGANISM: Homo sapiens
<400> SEQUENCE: 10

```
acggactgac atctttagct tcc                                               23
```

<210> SEQ ID NO 11
<211> LENGTH: 20
<212> TYPE: DNA
<213> ORGANISM: Homo sapiens
<400> SEQUENCE: 11

```
gcagctgcga ggttttcttt                                                   20
```

<210> SEQ ID NO 12
<211> LENGTH: 20
<212> TYPE: DNA
<213> ORGANISM: Homo sapiens
<400> SEQUENCE: 12

```
gccatgtggc ttgggcatac                                                   20
```

```
<210> SEQ ID NO 13
<211> LENGTH: 21
<212> TYPE: DNA
<213> ORGANISM: Homo sapiens

<400> SEQUENCE: 13
agtacttcct ctcccctccc a                                              21

<210> SEQ ID NO 14
<211> LENGTH: 21
<212> TYPE: DNA
<213> ORGANISM: Homo sapiens

<400> SEQUENCE: 14
gcagctgcga ggttttcttt t                                              21

<210> SEQ ID NO 15
<211> LENGTH: 22
<212> TYPE: DNA
<213> ORGANISM: Homo sapiens

<400> SEQUENCE: 15
cctctcccac acaaacctgc ta                                             22

<210> SEQ ID NO 16
<211> LENGTH: 24
<212> TYPE: DNA
<213> ORGANISM: Homo sapiens

<400> SEQUENCE: 16
acatggagca cacatacaag ctac                                           24

<210> SEQ ID NO 17
<211> LENGTH: 21
<212> TYPE: DNA
<213> ORGANISM: Homo sapiens

<400> SEQUENCE: 17
aaatgatgag gcacgggtga a                                              21

<210> SEQ ID NO 18
<211> LENGTH: 23
<212> TYPE: DNA
<213> ORGANISM: Homo sapiens

<400> SEQUENCE: 18
catggagcac acatacaagc tac                                            23

<210> SEQ ID NO 19
<211> LENGTH: 480
<212> TYPE: DNA
<213> ORGANISM: Homo sapiens

<400> SEQUENCE: 19
ttccacgtgg cctaccacag catgtcaggc ctggggcag aatcttgcca tactgtgcag      60
cccaaatttg aatgccaaag ctttcgtttt gtctctgggg ggccacagtc taggtctagt   120
tctgtgcagg agttgtaata tttgctcttc tctccctcct ccagctcgca gacctctgaa   180
gagagtgcca ttgagacggg ttccagcagt tccaccttca tcaagagaga ggacgagacc   240
attgaagaca tcgaaaagat aaaacaggtg ttagtgagga tatggggaaa taaaaccctc   300
atacacttct ggtgggattg taaaatggtg cagctgcttt gaagaacagc ctggccattt   360
```

```
tctcaaatgg tgaaacatgg agttaccatg tgagtcctcc accttagagg aatgaaaaca    420
tattcagaca aaaacttgta cgtgaatatt catagcagca ttattcttaa tagaaagtgg    480

<210> SEQ ID NO 20
<211> LENGTH: 647
<212> TYPE: DNA
<213> ORGANISM: Homo sapiens

<400> SEQUENCE: 20
tgggagtggg tggagtgaga acctgggaga aggccagccc tttatatcca ggcagacagc     60
tccaagtgcc accatggatc agccagtctt gcagggtga tgctattcag ctacagatgg     120
cttgatcctg agtcatttct ccttttcca tgcagtgtgt ccaccgtgat ctggctgctc     180
gcaacgtcct cctggcacaa ggaaaaattg tgaagatctg tgactttggc ctggccagag    240
acatcatgca tgattcgaaa agataaaaca ggtgttagtg aggatatggg gaaataaaac    300
cctcatacac ttctggtggg attgtaaaat ggtgcagctg cttttgaagaa cagcctggcc    360 attttctcaa atggtgaaac atggagttac catgtgagtc ctccaccttca gaggaatgaa    420 aacatattca gacaaaaact tgtacgtgaa tattcatagc agcattattc ttaatagaaa    480
gtggaaaaag aaaacctcgc agctgcatca actgatgaat ggatagatta aatgtgttat    540
atccatacag cggaatatta tttggcaagg acaataaaat gaagtactgg tagatgttac    600
aacacggatg aaccttacaa atgtggaagc taaagatgtc agtccgt             647

<210> SEQ ID NO 21
<211> LENGTH: 462
<212> TYPE: DNA
<213> ORGANISM: Homo sapiens

<400> SEQUENCE: 21
gcagctgcga ggttttcttt ttccactttc tattaagaat aatgctgcta tgaatattca     60
cgtacaagtt tttgtctgaa tatgttttca ttcctctaag gtggaggact cacatggtaa    120
ctccatgttt caccatttga gaaaatggcc aggctgttct tcaaagcagc tgcaccattt    180
tacaatccca ccagaagtgt atgagggttt tatttcccca tatcctcact aacacctgtt    240
ttatcttttc gaggtccttg ctgaacctgg acctataaat gacgtcaatg atagtgatcc    300
ctactgcaga aatctacaag tggctataaa gaactctgta ggtaagaaat tctgtaagat    360
cagaaagtac aatgaattca cttcataata aattacttgg tggacaccaa atgggtgcta    420
aattgattgg gtagaaggaa ttgtatgccc aagccacatg gc                     462

<210> SEQ ID NO 22
<211> LENGTH: 499
<212> TYPE: DNA
<213> ORGANISM: Homo sapiens

<400> SEQUENCE: 22
agtacttcct ctccctccc atattgttaa aaatagttta cattgcttcc caggctgggc     60
tggtggagtt ggcacgagat gtcagaggaa cctgagtcat gctcaggccc aagccctgtt    120
ggcaggcaga ccactgcttt ctggccttcc gtgactatcg aaaaaaatc gtgaatggct    180 agagctactc ttcacttgct gaacattttc aaaagaatt gagaacttct ggattaaatt    240
gccttcttcc tcgaaaagat aaaacaggt ttagtgagga tatggggaaa taaaccctc     300 atacacttct ggtgggattg taaatggtg cagctgcttt gaagaacagc ctggccattt    360
```

| | |
|---|---|
| tctcaaatgg tgaaacatgg agttaccatg tgagtcctcc accttagagg aatgaaaaca | 420 |
| tattcagaca aaaacttgta cgtgaatatt catagcagca ttattcttaa tagaaagtgg | 480 |
| aaaaagaaaa cctcgcagc | 499 |

```
<210> SEQ ID NO 23
<211> LENGTH: 609
<212> TYPE: DNA
<213> ORGANISM: Homo sapiens

<400> SEQUENCE: 23
```

| | |
|---|---|
| cctctcccac acaaacctgc tactgagtac cttcgctaac ttaaccattc attcaccctg | 60 |
| gaagaccacc tactagcaga aggattctta acaaatgtaa agaaagtaag gactttacac | 120 |
| taacaataca aaactaactc tctctttgac aattcaaaaa acaaaagatg ttgaactttg | 180 |
| acatttacag aattaaatgt caaatgtgac acaataccat cacatctggc taactaactc | 240 |
| ttatgctttt tttagtaagg aacaacttt gagcctcaat atcttaattc ttaaaatgat | 300 |
| aaagaacact taactcaatt tgttgagatc aaataaggta atgtaaaagt gggatttta | 360 |
| ttttactta tttattcgaa acccctggga cccttccaga tgggactaac tggggaaagt | 420 |
| ggacaagtta caaacaaaga aactcaaagg aaagtcattg gcactgatct ctaagatgct | 480 |
| atcacatgtg attggtggtt gatttatta acaaattata agcaaagtac tacaaaggtg | 540 |
| gctttaaaaa gaaaataaag caattcacag aaactacttt tcatgtagc ttgtatgtgt | 600 |
| gctccatgt | 609 |

```
<210> SEQ ID NO 24
<211> LENGTH: 586
<212> TYPE: DNA
<213> ORGANISM: Homo sapiens

<400> SEQUENCE: 24
```

| | |
|---|---|
| aaatgatgag gcacgggtga ataagatagt tggaagtgac acatacagat ttcaaataat | 60 |
| tccctaaagg tgtatggttt tcttccccta caaatcctac tttcagttct tttgtacatg | 120 |
| gacccagagt ggaattgctg gatcatatga taattctatt tttaacttct tgatggacct | 180 |
| ctgttttgt tttgttttt acagaggctg caacatttta tattcctact aataatgcac | 240 |
| aggggttcgg atttctccac atccttgcca acacttgata tttcctgggt ttttgataa | 300 |
| tggccatcct aataggtgtg gggacatgag gttttcaata tgcttgtggg acatcgaaaa | 360 |
| ccctgggacc cttccagatg ggactaactg gggaaagtgg acaagttaca acaaagaaa | 420 |
| ctcaaaggaa agtcattggc actgatctct aagatgctat cacatgtgat tggtggttga | 480 |
| ttttattaac aaattataag caaagtacta caaaggtggc tttaaaaaga aaataaagca | 540 |
| attcacagaa actacttttt catgtagctt gtatgtgtgc tccatg | 586 |

```
<210> SEQ ID NO 25
<211> LENGTH: 28
<212> TYPE: DNA
<213> ORGANISM: Homo sapiens

<400> SEQUENCE: 25
```

| | |
|---|---|
| tcagcaagga cctcgaaaag ataaaaca | 28 |

```
<210> SEQ ID NO 26
<211> LENGTH: 24
<212> TYPE: DNA
<213> ORGANISM: Homo sapiens
```

```
<400> SEQUENCE: 26
atttattcga aaaccctggg accc                                           24

<210> SEQ ID NO 27
<211> LENGTH: 20
<212> TYPE: DNA
<213> ORGANISM: Homo sapiens

<400> SEQUENCE: 27
gcagctgcga ggttttcttt                                                20

<210> SEQ ID NO 28
<211> LENGTH: 22
<212> TYPE: DNA
<213> ORGANISM: Homo sapiens

<400> SEQUENCE: 28
cctctcccac acaaacctgc ta                                             22

<210> SEQ ID NO 29
<211> LENGTH: 20
<212> TYPE: DNA
<213> ORGANISM: Homo sapiens

<400> SEQUENCE: 29
gccatgtggc ttgggcatac                                                20

<210> SEQ ID NO 30
<211> LENGTH: 24
<212> TYPE: DNA
<213> ORGANISM: Homo sapiens

<400> SEQUENCE: 30
acatggagca cacatacaag ctac                                           24

<210> SEQ ID NO 31
<211> LENGTH: 50
<212> TYPE: DNA
<213> ORGANISM: Homo sapiens

<400> SEQUENCE: 31
cttatagcct gtctctcttg ctgatcgagg ttgcaacgag ctgagattgc               50

<210> SEQ ID NO 32
<211> LENGTH: 24
<212> TYPE: DNA
<213> ORGANISM: Homo sapiens

<400> SEQUENCE: 32
ttggagttcc agggtgatac tgtc                                           24

<210> SEQ ID NO 33
<211> LENGTH: 23
<212> TYPE: DNA
<213> ORGANISM: Homo sapiens

<400> SEQUENCE: 33
accaacgcta ttcttggctt cca                                            23

<210> SEQ ID NO 34
<211> LENGTH: 800
<212> TYPE: DNA
```

<213> ORGANISM: Homo sapiens
<220> FEATURE:
<221> NAME/KEY: misc_feature
<222> LOCATION: (472)..(504)
<223> OTHER INFORMATION: n is a, c, g, or t

<400> SEQUENCE: 34

| | | | | | |
|---|---|---|---|---|---|
| gcaagctcca | cctcctgggt | tcaagtgatt | ctcctgcctc | agcctcctga | gtagctggga | 60 |
| ttacaggtgt | gccccaccat | gctctgctaa | tttatctatt | tttagtagag | atggggtttc | 120 |
| accatgttgg | tcaggctggt | cttgaattcc | tgaccttgtg | atccaccgc | ctcggcctcc | 180 |
| caaagtgctg | ggattacaga | catgagacac | tgcaccctgc | cccattcctt | ttaatctccc | 240 |
| ttggaattag | ctgtttggtt | gatttggagt | tccagggtga | tactgtctga | gtcataaatg | 300 |
| atttatttgt | gaatttctgt | ggctggtcac | gtattttggt | cctgtttgta | tttcccttcc | 360 |
| cctctctgtg | tctccttata | gcctgtctct | cttgctgatc | gaggttgcaa | cgagctgaga | 420 |
| ttgcacgcca | ctgcactccc | agcctgggcg | acggagtgag | actccatctc | annnnnnnnn | 480 |
| nnnnnnnnnn | nnnnnnnnnn | nnntgatga | cagcccaacc | tgtcacttt | ttcagatccc | 540 |
| tttttatgaa | agaatttgct | taagttgtgt | ctgaagacaa | accaatttct | ttggaccctg | 600 |
| ggtattcttt | ttctaaggga | ataccatgtt | attttgtgtt | acagattgtt | tgcgatcttt | 660 |
| cataggctga | tctttctaga | gttggttaat | atccatgtag | gttagattga | aaaacttgaa | 720 |
| ttcagaaatg | tacggtgttg | gagcagacat | ggatctggaa | gccaagaata | gcgttggtgt | 780 |
| tgttgttgat | ggtgaatctg | | | | | 800 |

<210> SEQ ID NO 35
<211> LENGTH: 49
<212> TYPE: DNA
<213> ORGANISM: Homo sapiens

<400> SEQUENCE: 35
gggccaagtg tgactctcag gttttcgacc tgcctcagcc tcccaaagt            49

<210> SEQ ID NO 36
<211> LENGTH: 23
<212> TYPE: DNA
<213> ORGANISM: Homo sapiens

<400> SEQUENCE: 36
atgcaggagg taaaatggag ggt                                        23

<210> SEQ ID NO 37
<211> LENGTH: 23
<212> TYPE: DNA
<213> ORGANISM: Homo sapiens

<400> SEQUENCE: 37
caaagagaca gctccgtcag aga                                        23

<210> SEQ ID NO 38
<211> LENGTH: 800
<212> TYPE: DNA
<213> ORGANISM: Homo sapiens

<400> SEQUENCE: 38

| | | | | | |
|---|---|---|---|---|---|
| ccactgcacc | agagcaaaga | gcaaaaggag | agatgcagga | ggtaaaatgg | agggtgggaa | 60 |
| gagaatggct | gaaggagagg | gtggccttat | tggcccattt | caaggatttt | gactttgatt | 120 |
| catatgatgt | gggaaggcct | tggagaattt | tccgagggga | ctatactatc | tgatgtatgt | 180 |

```
ttcagtatga aatagaatct ctctggctgc tatgatctga aggaggacaa gggagcaggg      240
attccacggg ggcattgatt gcacagagcc aggtaagagt gatgatgctt ggaccaaagt      300
ggtggcactg ggtggagggt cagaaccgac aagatttgct ctcggattag atgtgggata      360
tgggggtgtg agaggggcca agtgtgactc tcaggttttc gacctgcctc agcctcccaa      420
agtgctggga ttacaggtgt gagccaccgc acctggcctt ctgtctgtat ttttaaaaaa      480
aagatattca tgacaaccaa ggggagaggt aaggtcacag tgatgtgctc tgggtcaaag      540
attgttgagc ctggaccatt ggagagggga ggaaaagatg gaggtgtggg gtcaagggga      600
gaggctgcag aggacaggac agtgtgtggc caaggctgct gttgttcct tcatcaccct       660 ggccaggctg aggtccaggc agtgttctct gacggagctg tctctttgca cacgaggagc      720
ctgaaatatg gaaaagtaag tcgggctctt gatgttcctg tttgctgact gagactacaa      780
ggctattttt gaatccccat                                                  800
```

```
<210> SEQ ID NO 39
<211> LENGTH: 37
<212> TYPE: DNA
<213> ORGANISM: Homo sapiens

<400> SEQUENCE: 39
ttgaggacaa ggacctcgag atactgccga gaaatcc                                37

<210> SEQ ID NO 40
<211> LENGTH: 23
<212> TYPE: DNA
<213> ORGANISM: Homo sapiens

<400> SEQUENCE: 40
atgttgtcta acctgtatgt tct                                               23

<210> SEQ ID NO 41
<211> LENGTH: 20
<212> TYPE: DNA
<213> ORGANISM: Homo sapiens

<400> SEQUENCE: 41
cttcctctgc cgggtgctaa                                                   20

<210> SEQ ID NO 42
<211> LENGTH: 540
<212> TYPE: DNA
<213> ORGANISM: Homo sapiens

<400> SEQUENCE: 42
atgagtcctg aaacagagag agaggtcatg ctgttggtgt ggtgtaggag gtgggatgcc       60
tcacacatcc tcacttaaag cctcacactt ccggtgtgta tctttctagt acattttgaa      120
tcccagaaga cctccatgaa cccacatatt tccagaggtt tctcctctca caaaatactt      180
ttcagggaca aaaagagaa aatactaatt gaaatacact gcctaactga atatattccc       240
acctcccagc ccaggcttag ctcacatcct accttcttga tgaagctgtt cccccatatc      300
catgccctca ctaatgtctc agtttttaga aattttacag tgcttataaa ctttcttctg      360
atgttgtcta acctgtatgt tctttgagga caaggacctc gagatactgc cgagaaatcc      420
acgaccccaa aaggagaaaa aatggcacga atcttagttc cccattcctc ctacccaccc      480
tagatgttct aacggttagc acccggcaga ggaagagcag aagttcacaa gaagggtctg      540
```

<210> SEQ ID NO 43
<211> LENGTH: 40
<212> TYPE: DNA
<213> ORGANISM: Homo sapiens

<400> SEQUENCE: 43
tcacccagaa taaggcttct cgattctaag ttctacaaga                              40

<210> SEQ ID NO 44
<211> LENGTH: 20
<212> TYPE: DNA
<213> ORGANISM: Homo sapiens

<400> SEQUENCE: 44
cagtgcggtg ggagtactgt                                                   20

<210> SEQ ID NO 45
<211> LENGTH: 20
<212> TYPE: DNA
<213> ORGANISM: Homo sapiens

<400> SEQUENCE: 45
ttcagcaggt gcgtgttcag                                                   20

<210> SEQ ID NO 46
<211> LENGTH: 20
<212> TYPE: DNA
<213> ORGANISM: Homo sapiens

<400> SEQUENCE: 46
agtgcggtgg gagtactgtg                                                   20

<210> SEQ ID NO 47
<211> LENGTH: 20
<212> TYPE: DNA
<213> ORGANISM: Homo sapiens

<400> SEQUENCE: 47
acatttcagc aggtgcgtgt                                                   20

<210> SEQ ID NO 48
<211> LENGTH: 800
<212> TYPE: DNA
<213> ORGANISM: Homo sapiens

<400> SEQUENCE: 48
tcccattttg aaagcttatc ctttaatgac gagcttcagc cagtgcggtg ggagtactgt       60
gatcctcacg tggtggtgac ggggaggcag acattgagaa ctgaagggct ccctttgatc      120
attagcctta cataggatgc ctttaatgtt gagctagatt ggaagcccaa gtgactgctg      180
aagtgcacca aattaactca gaagtcacca atttcactcc atttatggaa gggtattaac      240 aggggggttga gaaacaattt aaggaaatgt taaataatgt attatttcca aatcactgca      300
tcatataatt aacatcctac ctgttgttag caattatttta taggtcatac agtataccaa     360
aatcagccaa agcaataaat cacccagaat aaggcttctc gattctaagt tctacaagat      420
gatcaaggaa ggcttccgga tgctcagccc tgaacacgca cctgctgaaa tgtaagagcc      480
aaaaaatttt tcctttaggt cacgttttcc cttttatttt tcttttttaga dacagaaacc     540 cagatgttga gggttttcat aacacagttt gaaatgtcac ttggattctt tatgacacac      600
tggtcaaatg tcatttctgt agtttatttt cataatctct tgtcaccaaa aatacagaaa      660

```
gtttcagtaa tatttcatac atgcagtgtt ttatgttatc tatatgtcag tccatatgtc    720
cagttgcata gccctggaat tattactgaa gttgctggat gcccatacat ttgaaaacaa    780
gctgagggca ttgaggaggg                                                800
```

<210> SEQ ID NO 49
<211> LENGTH: 51
<212> TYPE: DNA
<213> ORGANISM: Homo sapiens

<400> SEQUENCE: 49

```
aaacccagc agccctgcc caagtcgagg gagcagctcc ccacccagcc c              51
```

<210> SEQ ID NO 50
<211> LENGTH: 24
<212> TYPE: DNA
<213> ORGANISM: Homo sapiens

<400> SEQUENCE: 50

```
agaaagaggc aaagttagga agca                                           24
```

<210> SEQ ID NO 51
<211> LENGTH: 24
<212> TYPE: DNA
<213> ORGANISM: Homo sapiens

<400> SEQUENCE: 51

```
aaaacagcaa cctattcaga gagc                                           24
```

<210> SEQ ID NO 52
<211> LENGTH: 800
<212> TYPE: DNA
<213> ORGANISM: Homo sapiens

<400> SEQUENCE: 52

```
gagccgcacc atcctgggca tcacttactg gaggctactg agccagggca gtgggaattg     60
gagcatgggt cagtggggaa aacagctggc tgcctgggaa cccccatctc ttttccaccc    120
cactcctcca aaagtcaaag gaagaaagag gcaaagttag gaagcagctg tagcagcatt    180
aagcgcattt catttccccc atcctaaggg gaaaggtcgg ccctccccag gacttctttg    240
tgtccggagt tgccccctcc ccagatgctc agttctttgc caagattgcc acttgccaga    300
ggaacacccc atttcctttg ggatagctca gcctcaccct tccctagcaa cagctgaaca    360
aaccccgccc ctcaaaaccc cagcagcccc tgcccaagtc gagggagcag ctccccaccc    420
agccccagga tctgggtcca gcagacctgg agagtctgcc ctggctgcac agaccgtggt    480
gggactgtct ggcggaactg ttgtctggag acaatgcagc ccatgtgaca ggccttaatg    540
agtcccttct ggaatcccac aatggccaag tggcacaggc tctctgaata ggttgctgtt    600
tttcagcagt ggcaggggct gtgttgtggc aacctcctct cttattcaac ctccggcatc    660
tctcttcttt tcctttcttt cttacctttg tctttatct actttaactc tcctgttccc    720
ttttgatctc ttccttctcc tccaccctcc tgatttctgt tgtttcttag acacaaaatc    780
gcccttcact cctgccctgt                                                800
```

<210> SEQ ID NO 53
<211> LENGTH: 34
<212> TYPE: DNA
<213> ORGANISM: Homo sapiens

<400> SEQUENCE: 53
tatgcttgtg ggacatcgac aaaagcaatt atgc                                34

<210> SEQ ID NO 54
<211> LENGTH: 25
<212> TYPE: DNA
<213> ORGANISM: Homo sapiens

<400> SEQUENCE: 54
tggaagtgac acatacagat ttcaa                                          25

<210> SEQ ID NO 55
<211> LENGTH: 20
<212> TYPE: DNA
<213> ORGANISM: Homo sapiens

<400> SEQUENCE: 55
ctttctgcac cgtagccagc                                                20

<210> SEQ ID NO 56
<211> LENGTH: 800
<212> TYPE: DNA
<213> ORGANISM: Homo sapiens

<400> SEQUENCE: 56
cagctaaaga ctactttcc aagcctcttg cagctagcta tggacaaatg atgaggcacg     60
ggtgaataag atagttggaa gtgacacata cagatttcaa ataattccct aaaggtgtat   120
ggttttcttt ccctacaaat cctactttca gttcttttgt acatggaccc agagtggaat   180
tgctggatca tatgataatt ctatttttaa cttcttgatg gacctctgtt tttgttttgt   240
tttttacaga ggctgcaaca ttttatattc ctactaataa tgcacagggg ttcggatttc   300
tccacatcct tgccaacact tgatatttcc tgggtttttt gataatggcc atcctaatag   360
gtgtggggac atgaggtttt caatatgctt gtgggacatc gacaaaagca attatgctaa   420
tttccttccc tgtgggctca attccttttt tgacacgatg acttggagga gtcattatga   480
ttactccaaa caggaaagac actcgcccag ctgtccgccc gcagagagct ggctacggtg   540
cagaaagctg aggaggcgtc tggagttttt gggtgttaat gattctgcct gcccacaggt   600
cgggtcttgg ggtctggagc gtttgggaag gtggttgaag aacagccta tggattaagc     660 cggtcccaac ctgtcatgaa agttgcagtg aagatgctaa aacgtaagtg ctccttcctg   720 gggattttttt gagcacgggg attttttgag catggggata ttaagggaat ttctcaaaat   780
catgcagcta gtaaataaga                                               800

<210> SEQ ID NO 57
<211> LENGTH: 50
<212> TYPE: DNA
<213> ORGANISM: Homo sapiens

<400> SEQUENCE: 57
cctcggcgac agagtgagac tctgtcgatc tcattctttg gtttctgaac                50

<210> SEQ ID NO 58
<211> LENGTH: 23
<212> TYPE: DNA
<213> ORGANISM: Homo sapiens

<400> SEQUENCE: 58
ggtatgtgcc tgtagtccca act                                            23

<210> SEQ ID NO 59
<211> LENGTH: 23
<212> TYPE: DNA
<213> ORGANISM: Homo sapiens

<400> SEQUENCE: 59
gaaggatggt gaaacgctta cgg                                              23

<210> SEQ ID NO 60
<211> LENGTH: 800
<212> TYPE: DNA
<213> ORGANISM: Homo sapiens
<220> FEATURE:
<221> NAME/KEY: misc_feature
<222> LOCATION: (156)..(191)
<223> OTHER INFORMATION: n is a, c, g, or t

<400> SEQUENCE: 60
taattgcatc actgcactcc agcctgggca acagtgagaa cttgtcttaa agaaacaaag      60
caggttcttt cctctcagaa gcccctctct cttactagag agagagctgt tctcctctct     120
ctttcttcta ttaaacctcc gctcctaaaa acacannnnn nnnnnnnnnn nnnnnnnnnn     180
nnnnnnnnnn ncctaaaaa actagcctgg gcaacatggt aaaaccctgt ctctacaaaa      240
aacacaaata aactagccag gcctggtggt atgtgcctgt agtcccaact attcagggaa     300
gctgaggtgg gaggtttgct tgagaccggg aagtccaggc tgcagtgagc cgagatggcg     360
ccactgcact ctagcctcgg cgacagagtg agactctgtc gatctcattc tttggtttct     420
gaactcagcc cactttccct cacataatac agatcttccc gagagtcccg taagcgtttc     480
accatccttc ttttttccag tttgcctttg taaagctcat ttcttttac tgtgaaatta     540 ataaatagca ataatacaaa tctcttttaa ggtatataaa aattcttccc tgaggagctc     600
tgtaggaatt ataagtagat cacgattcaa tttattctaa tatacgagtt taacccaatt     660
tacaatttac atatctttag gaaatggctt catgctttca gaccacaaat attccaaaag     720
gaataatttc agtgtattta atattccagt gaacagaacg aatcaaaggg gctaagtact     780
gaccagtgga tactggtcac                                                 800

<210> SEQ ID NO 61
<211> LENGTH: 50
<212> TYPE: DNA
<213> ORGANISM: Homo sapiens

<400> SEQUENCE: 61
actttactgt gtccccatca cgtgtcgaca gagtctcact ctgtcgccga                 50

<210> SEQ ID NO 62
<211> LENGTH: 23
<212> TYPE: DNA
<213> ORGANISM: Homo sapiens

<400> SEQUENCE: 62
caagcatctc tcaggatccc cat                                              23

<210> SEQ ID NO 63
<211> LENGTH: 23
<212> TYPE: DNA
<213> ORGANISM: Homo sapiens

<400> SEQUENCE: 63
actattcagg gaagctgagg tgg                                            23

<210> SEQ ID NO 64
<211> LENGTH: 800
<212> TYPE: DNA
<213> ORGANISM: Homo sapiens
<220> FEATURE:
<221> NAME/KEY: misc_feature
<222> LOCATION: (1)..(128)
<223> OTHER INFORMATION: n is a, c, g, or t
<220> FEATURE:
<221> NAME/KEY: misc_feature
<222> LOCATION: (610)..(645)
<223> OTHER INFORMATION: n is a, c, g, or t

<400> SEQUENCE: 64
nnnnnnnnnn nnnnnnnnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnnnnnnaa gaatgctcca aggctcaacg aatgcctcca tcagaatgcc tgggaatcca   180
ttcagagaaa ggtgctacaa agccatgatg ctcaagtaat tagcaagaaa gttcaaggat   240
gaggaggaga tccagcaaac tcctacagcc ctcatttatg cccgctaaag caataaatcc   300
ctgcaggacc aagcatctct caggatcccc atggatgcgg aggataaaca cagagcagag   360
acaaggttac tgctacttta ctgtgtcccc atcacgtgtc gacagagtct cactctgtcg   420
ccgaggctag agtgcagtgg cgccatctcg gctcactgca gcctggactt cccggtctca   480
agcaaacctc ccacctcagc ttccctgaat agttgggact acaggcacat accaccaggc   540
ctggctagtt tatttgtgtt ttttgtagag cagggttttt accatgttgc ccaggctagt   600
tttttagggn nnnnnnnnnn nnnnnnnnnn nnnnnnnnnn nnnnntgtgt ttttaggagc   660
ggaggtttaa tagaagaaag agagaggaga acagctctct ctctagtaag agagagggc    720 ttctgagagg aaagaacctg ctttgtttct ttaagacaag ttctcactgt tgcccaggct   780
ggagtgcagt gatgcaatta                                              800

<210> SEQ ID NO 65
<211> LENGTH: 50
<212> TYPE: DNA
<213> ORGANISM: Homo sapiens

<400> SEQUENCE: 65
gagttcagaa accaaagaat gagatcgagt gattgctagg tgatggacct               50

<210> SEQ ID NO 66
<211> LENGTH: 23
<212> TYPE: DNA
<213> ORGANISM: Homo sapiens

<400> SEQUENCE: 66
gaaggatggt gaaacgctta cgg                                            23

<210> SEQ ID NO 67
<211> LENGTH: 23
<212> TYPE: DNA
<213> ORGANISM: Homo sapiens

<400> SEQUENCE: 67
tgcaccccaa caggagtttt cta                                            23

<210> SEQ ID NO 68
<211> LENGTH: 800

```
<212> TYPE: DNA
<213> ORGANISM: Homo sapiens

<400> SEQUENCE: 68
gtgaccagta tccactggtc agtacttagc cctttgatt cgttctgttc actggaatat      60
taaatacact gaaattattc cttttggaat atttgtggtc tgaaagcatg aagccatttc    120
ctaaagatat gtaaattgta aattgggtta aactcgtata ttagaataaa ttgaatcgtg    180
atctacttat aattcctaca gagctcctca gggaagaatt tttatatacc ttaaaagaga    240
tttgtattat tgctatttat taatttcaca gtaaaaagaa atgagcttta caaaggcaaa    300
ctggaaaaaa gaaggatggt gaaacgctta cgggactctc gggaagatct gtattatgtg    360
agggaaagtg ggctgagttc agaaaccaaa gaatgagatc gagtgattgc taggtgatgg    420
acctgtaggg agagatcact agatgagttc aggtggtaaa tagaaaactc ctgttggggt    480
gcagtgagag atgaaggtag tgaaatgaaa ggatggggat caattttata tgagggcttt    540
aatttgaaat gggaatttgg tgatattctc agagcagcac aagttttcat gccatggaaa    600
agcagcagga aaaatgtaaa ccttgccaat aacacgggaa agtctccaag ggtgcccagt    660
gacttacttg cctataaaca aagccattcc tgagcacttc tggctatgaa atttcaaaat    720
acatgtttta gagaatttta ctgacacttt tatgatttta gaggataatt tagatttcat    780
aaattttgtt tccttccctt                                                800

<210> SEQ ID NO 69
<211> LENGTH: 53
<212> TYPE: DNA
<213> ORGANISM: Homo sapiens

<400> SEQUENCE: 69
gctggaggat tgcttgagct tgggaggtcg atctcattct ttggtttctg aac              53

<210> SEQ ID NO 70
<211> LENGTH: 22
<212> TYPE: DNA
<213> ORGANISM: Homo sapiens

<400> SEQUENCE: 70
gcttctggag gccagggatt at                                                22

<210> SEQ ID NO 71
<211> LENGTH: 23
<212> TYPE: DNA
<213> ORGANISM: Homo sapiens

<400> SEQUENCE: 71 agccccttttg attcgttctg ttc                                              23

<210> SEQ ID NO 72
<211> LENGTH: 800
<212> TYPE: DNA
<213> ORGANISM: Homo sapiens
```

```
<400> SEQUENCE: 72
cacactcatg cttcataaga aagggctagt ggcttctgga ggccagggat tatttttatt        60
tagttttatt tagttgtcta cttcactgca ctgaactctt aagagctttt aatttattaa       120
tcatttggct gaaatcagga aaggtgtttt ttttccctaa aaacattttt atcaatatgt       180
cttagggcag gcagaggagc tcatgccctg tgatcccagc actttgggag gctgaggtgg       240
gggaatcgct tgagcccagg agttcaagac cagcctgggc aatacagtga taccctattt       300
ctacaaaaaa taaaaaactt agcctggcgt ggtgctgccc tcccatggtc ctagctactt       360
ggaaggccgt ggctggagga ttgcttgagc ttgggaggtc gatctcattc tttggtttct       420
gaactcagcc cactttccct cacataatac agatcttccc gagagtcccg taagcgtttc       480
accatccttc ttttttccag tttgcctttg taaagctcat ttcttttttac tgtgaaatta       540 ataaatagca ataatacaaa tctctttttaa ggtatataaa aattcttccc tgaggagctc       600
tgtaggaatt ataagtagat cacgattcaa tttattctaa tatacgagtt taacccaatt       660
tacaatttac atatctttag gaaatggctt catgctttca gaccacaaat attccaaaag       720
gaataatttc agtgtattta atattccagt gaacagaacg aatcaaaggg gctaagtact       780
gaccagtgga tactggtcac                                                   800
```

APPLICATION OF EPIGENETIC CHROMOSOMAL INTERACTIONS IN CANCER DIAGNOSTICS

CROSS REFERENCE TO RELATED APPLICATIONS

The present application is filed under 35 U.S.C. § 371 as the U.S. national phase of International Patent Application No. PCT/GB2017/053615, filed Nov. 30, 2017, which designated the United States and claims priority to U.S. Provisional Application No. 62/428,893 filed Dec. 1, 2016, each of which is hereby incorporated in its entirety including all tables, figures and claims.

SEQUENCE LISTING

The instant application contains a Sequence Listing which has been submitted in ASCII format via EFS-Web and is hereby incorporated by reference in its entirety. Said ASCII copy, created on May 29, 2019, is named 12440.001US1_SeqListing.txt and is 29 kilobytes in size.

FIELD OF THE INVENTION

The invention relates to detecting chromosome interactions.

BACKGROUND OF THE INVENTION

The global population have grown to expect fast-paced and effective services in all aspects of technology, and particularly in the field of medicine. Improvements in personalised therapy often rely on use of a biomarker such as protein, mRNA, antibody and SNP markers.

SUMMARY OF THE INVENTION

The inventors have investigated the role of chromosome interactions in prognosis of cancer. Their work shows that specific chromosome interactions are associated with particular outcomes, such as responsiveness to therapy. As part of this work the inventors have also developed a new epigenetic test assay that is particularly suited to detection of ligated nucleic acids which are produced in the course of detecting a chromosome interaction.

Accordingly the invention provides a method of determining the epigenetic chromosome interactions which are relevant to a prognostic companion epigenetic test for cancer that distinguishes between subgroups, comprising contacting a first set of nucleic acids from the subgroups with a second set of nucleic acids representing an index population of chromosome interactions, and allowing complementary sequences to hybridise, wherein the nucleic acids in the first and second sets of nucleic acids represent a ligated product comprising sequences from both of the chromosome regions that have come together in the epigenetic chromosome interaction, and wherein the pattern of hybridisation between the first and second set of nucleic acids allows a determination of which epigenetic chromosome interactions are specific to subgroups in the population, wherein the subgroups differ in at least one characteristic related to prognosis. Typically the subgroups differ in respect of responsiveness to tyrosine kinase inhibitor therapy, and/or the cancer is associated with abnormal expression from a kinase gene and/or a tyrosine kinase receptor gene, and/or the cancer is associated with a genetic or epigenetic change in one or more of the following genes: FIP1L1, PDGFRA, Flt3, ABL1, FGFR1 and cKIT.

The invention also provides a method of determining prognosis for a cancer comprising: (a) typing a chromosome interaction which has been identified by the above method, and/or (b) detecting the presence or absence of at least one epigenetic chromosome interaction which is relevant to (i) responsiveness to tyrosine kinase inhibitor therapy, and/or (ii) abnormal expression from a kinase gene and/or a tyrosine kinase receptor gene, and/or (iii) one or more of the following genes: FIP1L1, PDGFRA, Flt3, ABL1, FGFR1 and cKIT.

The invention further provides a method for quantitatively detecting a ligated sequence which is relevant to a chromosome interaction using a probe which is detectable upon activation during a PCR reaction, wherein said ligated sequence comprises sequences from two chromosome regions that come together in an epigenetic chromosome interaction, wherein said method comprises contacting the ligated sequence with the probe during a PCR reaction, and detecting the extent of activation of the probe, and wherein said probe binds the ligation site. The method allows particular interactions to be detected in a MIQE compliant manner using a dual labelled fluorescent hydrolysis probe.

The applicant's work offers to industry for the first time a MIQE compliant chromosome conformation (3C) assay for determining prognosis in an oncological situation.

DETAILED DESCRIPTION OF THE INVENTION

Figure 1:
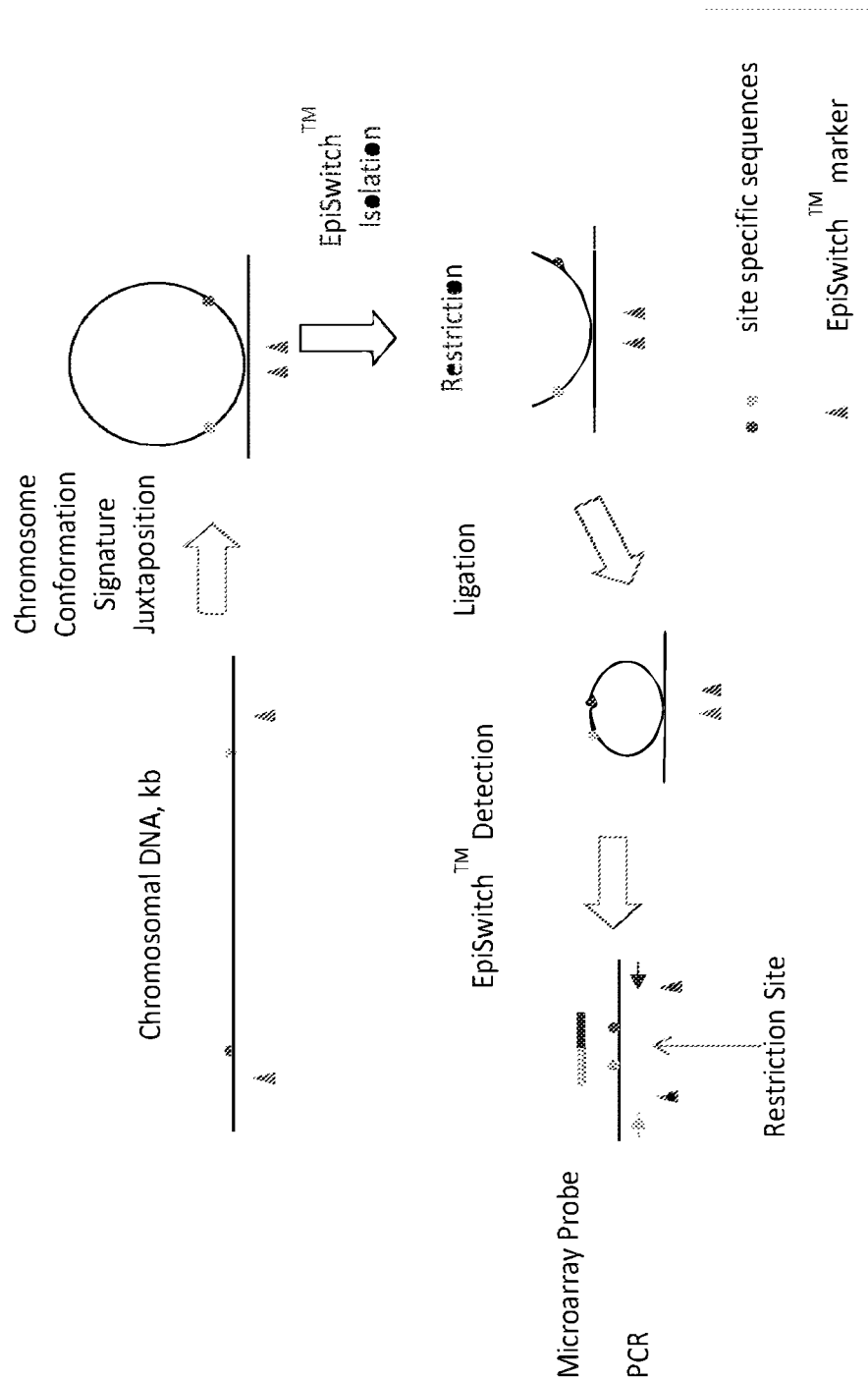
FIG. 1 is a schematic diagram of the 3C process. 3C means chromatin conformation capture, or chromosome conformation capture.
Figure 2:
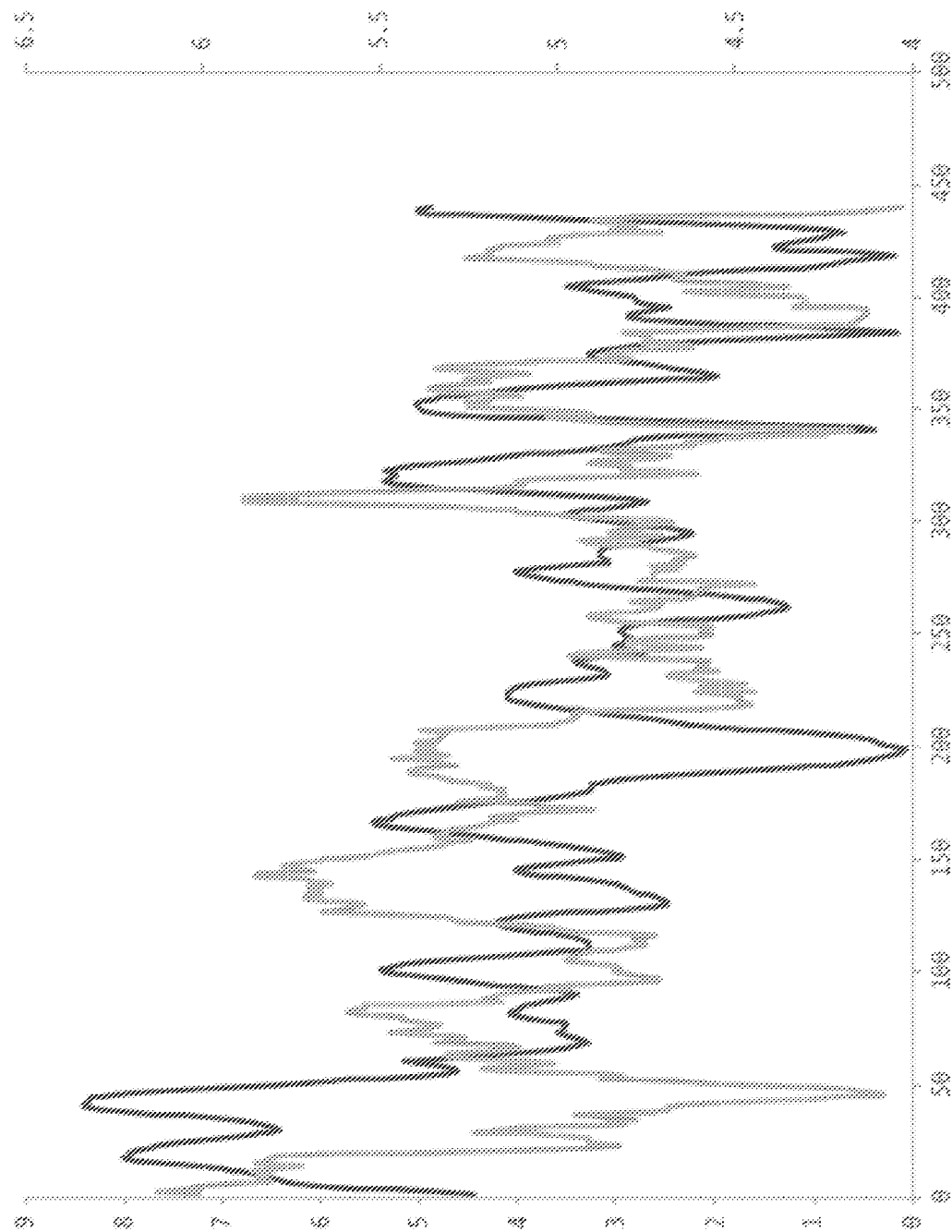
FIG. 2 is a graph of curvature and bendability against sequence position for ligated sequence 1. Predicted curvature in degrees per 10.5 bp helical turn is shown in black (Scale from 0 to 9 on left hand Y-axis), and bendability in a.u. is shown in grey (Scale from 4 to 6.5 on right hand Y-axis). Sequence number in base pairs from 0 to 500 is shown on the X-axis.
Figure 3:
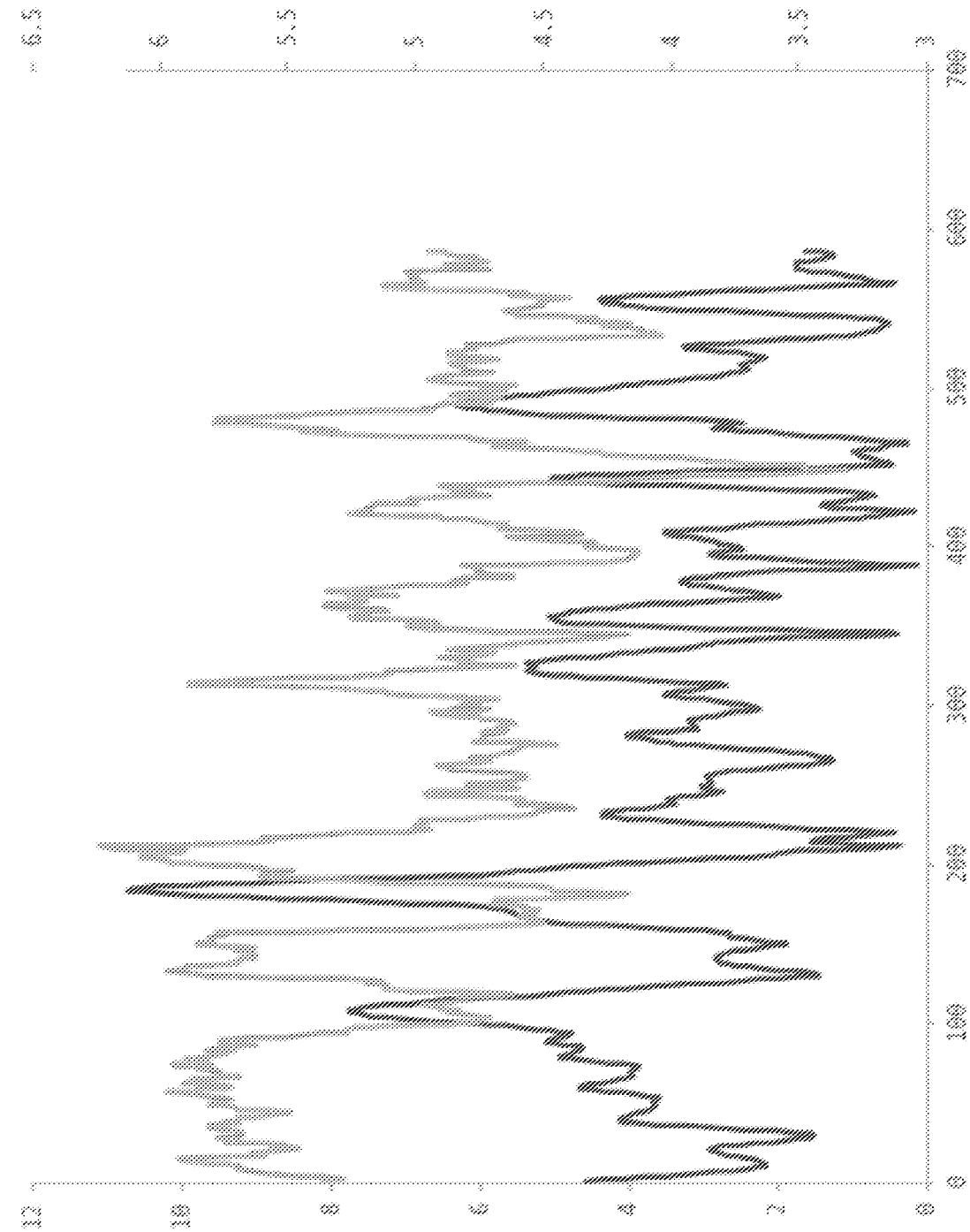
FIG. 3 is a graph of curvature and bendability against sequence position for ligated sequence 2. Predicted curvature in degrees per 10.5 bp helical turn is shown in black (Scale from 0 to 12 on left hand Y-axis), and bendability in a.u. is shown in grey (Scale from 3 to 6.5 on right hand Y-axis). Sequence number in base pairs from 0 to 700 is shown on the X-axis.
Figure 4:
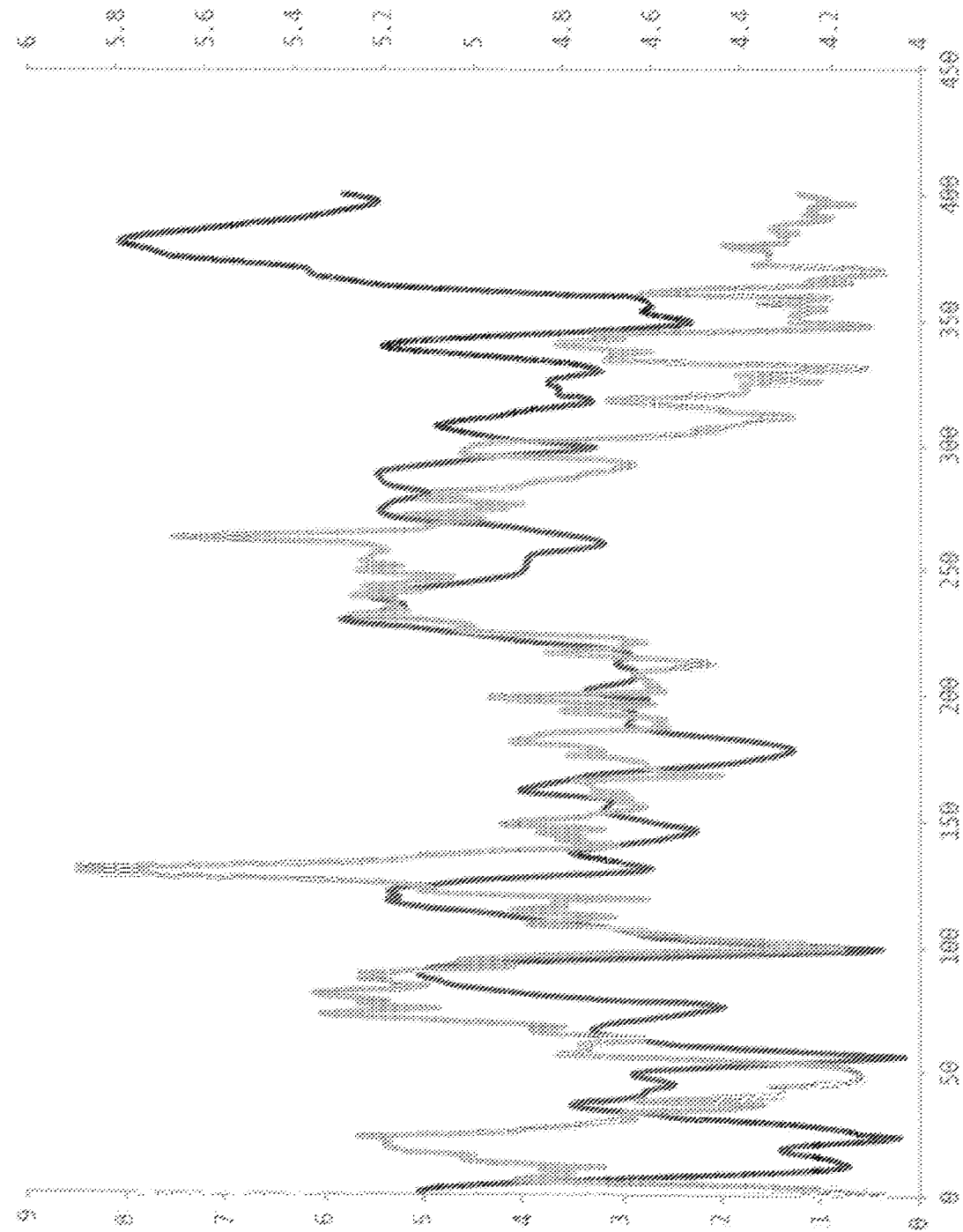
FIG. 4 is a graph of curvature and bendability against sequence position for ligated sequence 3. Predicted curvature in degrees per 10.5 bp helical turn is shown in black (Scale from 0 to 9 on left hand Y-axis), and bendability in a.u. is shown in grey (Scale from 4 to 6 on right hand Y-axis). Sequence number in base pairs from 0 to 450 is shown on the X-axis.
Figure 5:
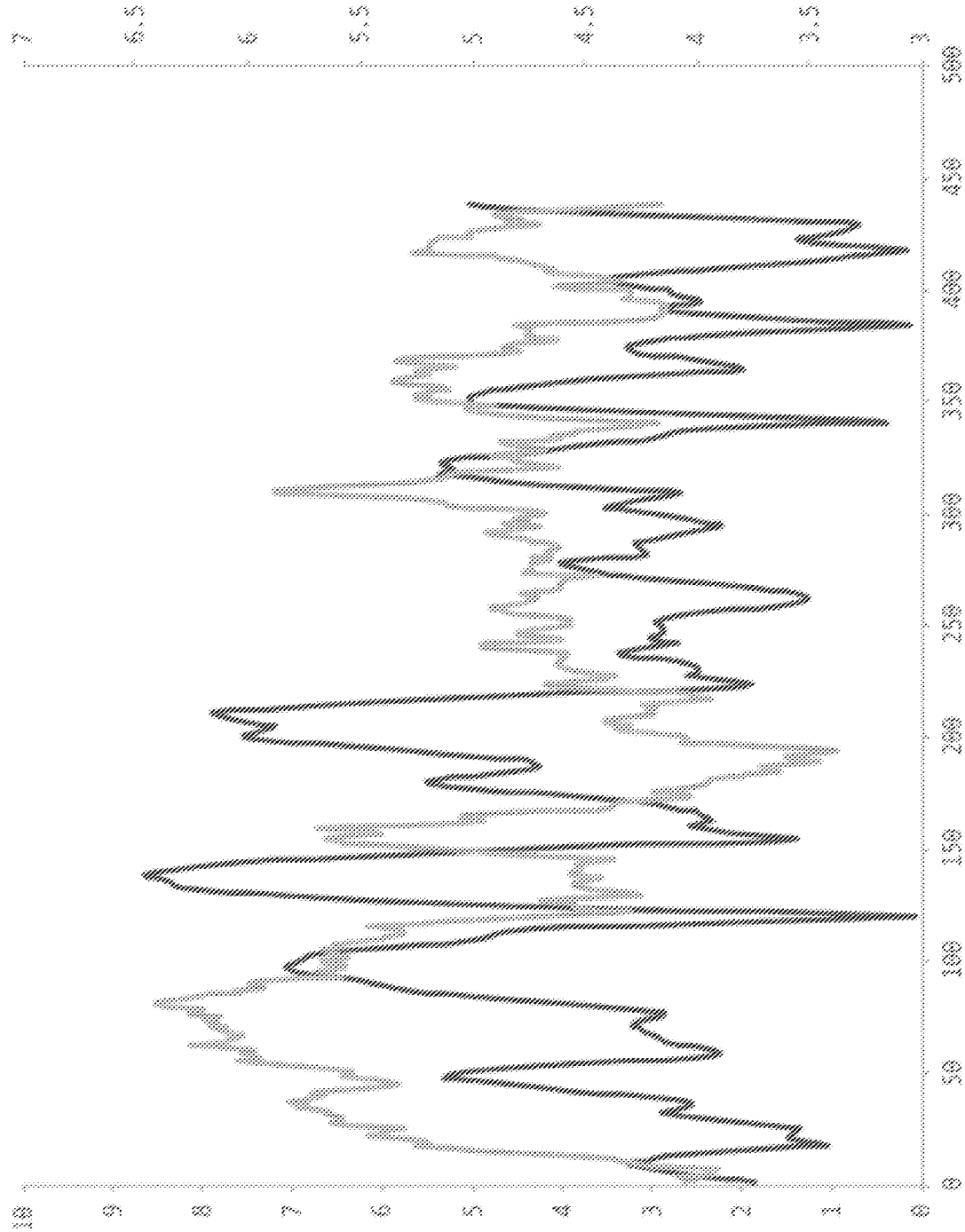
FIG. 5 is a graph of curvature and bendability against sequence position for ligated sequence 4. Predicted curvature in degrees per 10.5 bp helical turn is shown in black (Scale from 0 to 10 on left hand Y-axis), and bendability in a.u. is shown in grey (Scale from 3 to 7 on right hand Y-axis). Sequence number in base pairs from 0 to 500 is shown on the X-axis.
Figure 6:
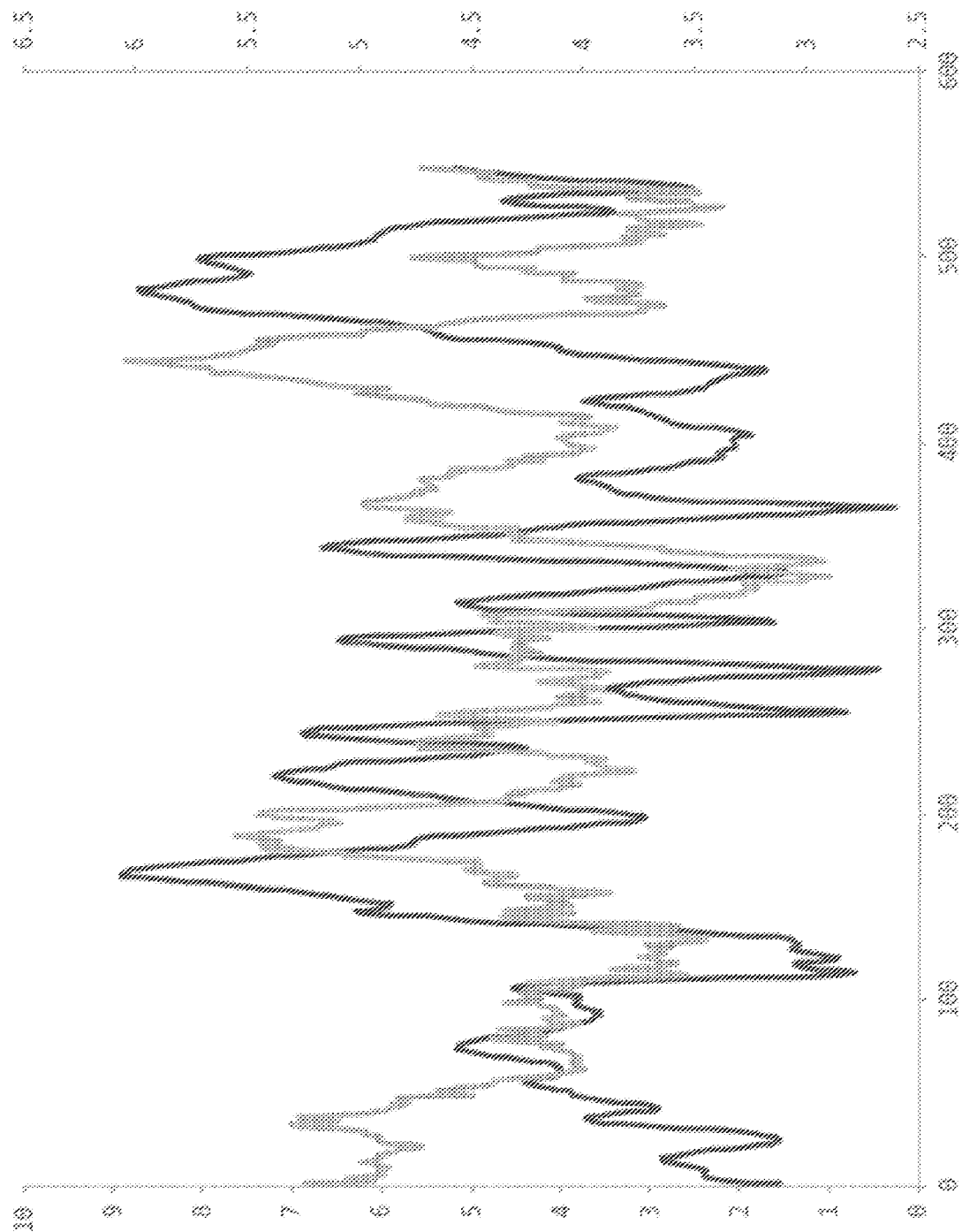
FIG. 6 is a graph of curvature and bendability against sequence position for ligated sequence 5. Predicted curvature in degrees per 10.5 bp helical turn is shown in black (Scale from 0 to 9 on left hand Y-axis), and bendability in a.u. is shown in grey (Scale from 3 to 6.5 on right hand Y-axis). Sequence number in base pairs from 0 to 700 is shown on the X-axis.
Figure 7:
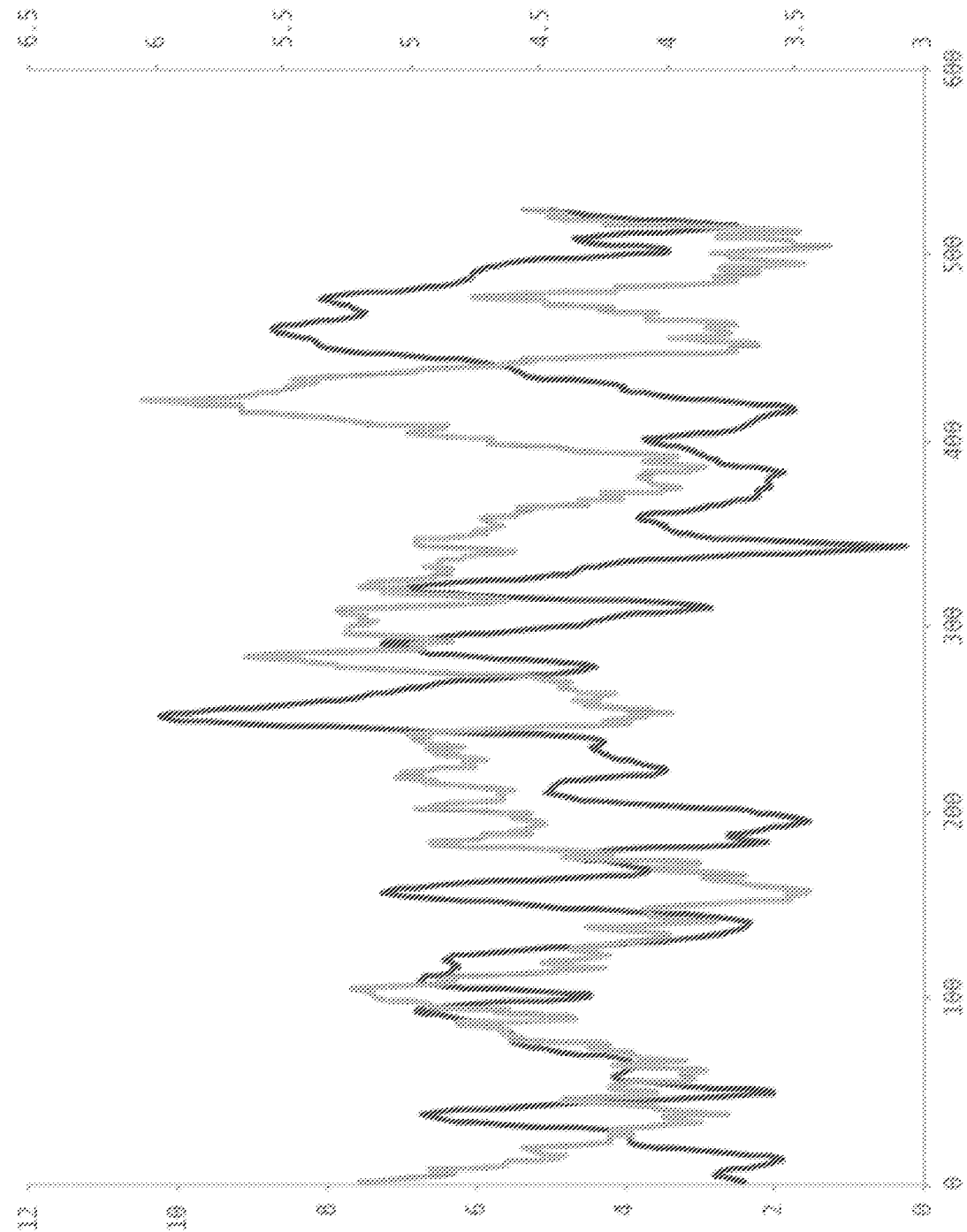
FIG. 7 is a graph of curvature and bendability against sequence position for ligated sequence 6. Predicted curvature in degrees per 10.5 bp helical turn is shown in black (Scale from 0 to 12 on left hand Y-axis), and bendability in a.u. is shown in grey (Scale from 3 to 6.5 on right hand Y-xis). Sequence number in base pairs from 0 to 600 is shown on the X-axis.

The invention relates to identifying particular aberrant processes, in particular with a robust quantitative test. The invention has several different aspects, including inter alia:
- a method for identifying epigenetic chromosome interactions relevant to different subgroups
- a method for identifying the subgroup of an individual
- a method of quantitatively detecting a ligated sequence which is relevant to a chromosome interaction
- a hydrolysis probe which is detectable upon activation during a PCR reaction where the probe binds the ligation site of a ligated nucleic acid
- a method of selecting primers and a probe for use in a PCR reaction
- a method of treating a cancer
- a nucleic acid for use in treating a cancer
- a method of identifying a therapeutic agent.

Cancers Relevant to the Invention

The invention concerns epigenetic interactions relevant to cancer, for example cancers caused by different genetic mechanisms, such as mutations in enzymes (including those responsible for demethylation of DNA), or caused by alternative gene splicing or by break point mutations. The cancer may be caused by upregulation of a receptor. The cancer may be associated with abnormal expression from a kinase gene and/or a tyrosine kinase receptor gene, for example a cytoplasmic kinase gene and/or a serine/threonine kinase gene. The cancer may be associated with a genetic or epigenetic change in one or more of the following genes: FIP1L1, PDGFRA, Flt3, ABL1, FGFR1 and cKIT. The cancer may be associated with a genetic or epigenetic change in proteins that are sensitive to ATP mimetics, optionally tyrosine kinase genes, such as ABL1, Bruton's Tyrosine Kinase, cKIT, FGFR1, PDGFRA and PDGFRB. Tyrosine kinase genes (ABL1, Brutons, cKIT, FGFR1, and PDGFRA) are classed are frequently classed as 'oncogenes,' functionally when expressed. The genetic or epigenetic change in proteins that are sensitive to ATP mimetics may be due to a change in expression of a gene which causes upregulation of a protein that is sensitive to ATP mimetics. For example, FIP1L1 is thought to directly upregulate PDGFRA mRNA expression.

The cancer may be a leukemia, a myeloproliferative neoplasm, a tumour, lung cancer or ovarian cancer. The cancer may be selected from idiopathic hypereosinophilic syndrome (iHES), chronic and acute eosinophilic leukemias, chronic myeloid leukemia (CML), acute myeloid leukemia (AML), Acute Lymphocytic Leukemia (ALL), PDGFRA-positive non-small cell lung carcinoma (NSCLC), glioblastoma (including glioblastoma multiforme and astrocytoma), prostate cancer, advanced ovarian cancer, gastrointestinal stromal tumour (GIST) and renal cell carcinoma.

Chromosome Interactions which are Typed

The invention concerns typing of chromosome interactions, for example those associated with cancer and/or responsiveness to tyrosine kinase inhibitor therapy. The chromosome interactions will affect or be associated with an aspect of disease, such as in any of the disease conditions mentioned herein. The chromosome interactions may affect or be associated with susceptibility to disease, responsiveness to therapy or likelihood of relapse. The chromosome interactions may affect or be associated with prognosis for a patient and/or for a subgroup of patients. Specific chromosome interactions, genes and regions are disclosed herein, and in one embodiment those chromosome interactions, or chromosome interactions in those genes and regions, may be typed. Preferred regions are disclosed as ranges in Table 1a. Specific ligated sequences are disclosed herein. The typing of the chromosome interactions may require detection of such ligated sequences or homologues and/or fragments thereof.

Preferred chromosome interactions, genes and regions (genomic locations) are shown in the tables, including tables 5, 6, 7, 8, 9, 10, 11, 12, 13 and 14. Further preferred chromosome interactions are those which may be defined or detected using any nucleic acid mentioned herein, for example probes or primer pairs.

The chromosome interaction which is typed may or may not be one which occurs between a gene (including coding sequence) and its regulatory region, such as a promoter.

The chromosome interaction may be associated with deregulation of a gene, for example a change in the activity (such as an increase or decrease) in an enhancer. The chromosome interaction may be associated with a mutation, such as a breakpoint mutation, which leads to a fusion genomic (chromosomal) product (which may or may not lead to expression of a fusion protein which has altered activity).

The breakpoint mutation may be:
- any such mutation mentioned herein, or
- within, spanning or including any gene mentioned herein, or
- a breakpoint mutation which is associated with or causes cancer.

The break point mutation may be at least 1,000 nucleotides, 10,000 nucleotides, 50,000 nucleotides, 100,000 nucleotides, 500,000 nucleotides, such as at least 800,000 nucleotides in length, which represent the length of the deleted fragment.

Prognosis

Prognostic as used herein relates to predicting the likely course of a medical condition, such as one or more outcomes. A prognostic factor is a clinical or biologic characteristic that is objectively measurable and that provides information on the likely outcome of the cancer disease, for example in a treated or untreated individual. A predictive factor may provide information on the likely benefit from treatment (for example either in terms of tumor shrinkage or survival). Such predictive factors can be used to identify subpopulations of patients who are most likely to benefit from a given therapy. A marker can have properties relating to prognosis as well as being predictive of the likely benefit from treatment.

Kinases

The invention may relate to a change in a kinase gene or kinase receptor gene, for example in a change in expression and/or a change in the epigenetic form and/or a genetic (genomic sequence) change, and this be associated with cancer and/or cause cancer. Typically therefore the cancer may be associated with abnormal expression of a kinase gene and/or a tyrosine kinase receptor. In one embodiment the cancer is associated with abnormal expression of a cytoplasmic tyrosine kinase (e.g. ABL1) and/or a cytoplasmic kinase (e.g. a serine/threonine kinase). The term 'abnormal expression' may include up-regulation or down-regulation, or may include expression of a different protein.

A 'kinase' in this context is may be defined functionally as undergoing a conformational change during the transfer of ATP to other proteins, in the nucleus, cytoplasm or at the cell membrane, or any other cellular location including extracellular locations. Examples of the kinase family that are relevant include receptor tyrosine kinases (e.g. PDGFRA) which are on the cell surface, and non-receptor kinases, such as cytoplasmic tyrosine kinases (e.g. ABU) and serine/threonine kinases.

Epigenetic Interactions

As used herein, the term 'epigenetic' interactions typically refers to interactions between distal regions on a chromosome, said interactions in one embodiment being dynamic and altering, forming or breaking depending upon the status of the region of the chromosome.

In particular methods of the invention chromosome interactions are detected by first generating a ligated nucleic acid that comprises sequence from both regions of the chromosomes that are part of the interactions. In such methods the regions can be cross-linked by any suitable means. In a preferred embodiment, the interactions are cross-linked using formaldehyde, but may also be cross-linked by any aldehyde, or D-Biotinoyl-e-aminocaproic acid-N-hydroxysuccinimide ester or Digoxigenin-3-O-methylcarbonyl-e-aminocaproic acid-N-hydroxysuccinimide ester. Paraformaldehyde may be used and can cross link DNA chains which are 4 Angstroms apart.

The chromosome interaction may reflect the status of the region of the chromosome, for example, if it is being transcribed or repressed in response to change of the physiological conditions. Chromosome interactions which are specific to subgroups as defined herein have been found to be stable, thus providing a reliable means of measuring the differences between the two subgroups.

In addition, chromosome interactions specific to a characteristic (such as a disease condition) will normally occur early in a biological process, for example compared to other epigenetic markers such as methylation or changes to binding of histone proteins. Thus the method of the invention is able to detect early stages of a biological process. This allows early intervention (for example treatment) which may as a consequence be more effective. Furthermore there is little variation in the relevant chromosome interactions between individuals within the same subgroup.

Location and Causes of Epigenetic Interactions

Epigenetic chromosomal interactions may overlap and include the regions of chromosomes shown to encode relevant or undescribed genes, but equally may be in intergenic regions. The chromosome interactions which are detected in the invention could be caused by changes to the underlying DNA sequence, by environmental factors, DNA methylation, non-coding antisense RNA transcripts, non-mutagenic carcinogens, histone modifications, chromatin remodelling and specific local DNA interactions. The same chromosome interaction may be caused by different factors in different subjects. For example, a particular chromosome interaction may be caused by changes in DNA methylation, e.g. due to mutation in IDH in a different region of the chromosome from where the interaction is observed. The same chromosome interaction may be caused by a change to the underlying sequence, e.g. a deletion in the same region of the chromosome as where the interaction is observed.

The changes which lead to the chromosome interactions may be caused by changes to the underlying nucleic acid sequence, which themselves do not directly affect a gene product or the mode of gene expression. Such changes may be for example, SNP's within and/or outside of the genes, gene fusions and/or deletions of intergenic DNA, microRNA, and non-coding RNA. For example, it is known that roughly 20% of SNPs are in non-coding regions, and therefore the method as described is also informative in a non-coding situation. The regions of the chromosome which come together to form the interaction can be less than 5 kb, 3 kb, 1 kb, 500 base pairs or 200 base pairs apart on the same chromosome. The regions of the chromosome which come together to form the interaction can be more than 5 kb, 10 kb, 50 kb, 100 kb, 200 kb, 500 kb, or more than 800 kb apart on the same chromosome, and can for example be 800 kb to 1,200 kb, such as 900 kb to 1,000 kb apart. Any such values and ranges disclosed herein can refer to a normal chromosome (without a breakpoint mutation) or a chromosome with a breakpoint mutation.

The chromosome interaction which is detected is preferably within any of the genes mentioned herein. However it may also be upstream or downstream of the genes, for example up to 50,000, up to 30,000, up to 20,000, up to 10,000 or up to 5000 bases upstream or downstream from the gene or from the coding sequence.

Types of Clinical Situation

The aim of the present invention is to permit detection of chromosome interactions relevant to a characteristic that defines subgroups in the population. For example, this technology allows stratification based on biomarkers for specific phenotypes (e.g. relating to medical conditions), i.e. by recognising a particular chromosome conformation signature and/or a change in that particular signature. The characteristic that defines the subgroup is relevant to prognosis for a cancer. The methods of the invention may be used in the context of specific characteristics relating to disease, such as responsiveness to treatments, identification of the most effective therapy/drug, monitoring the course of disease, identifying predisposition to disease, identifying the presence of residual disease and/or the likelihood of relapse. Therefore the methods may or may not be used for diagnosis of the presence of a specific condition. In one embodiment the invention may be used to monitor the response to treatment, for example in an ongoing manner. The methods of the invention can be used to type loci where the mechanisms of disease are unknown, unclear or complex. Detection of chromosome interactions provides an efficient way of following changes at the different levels of regulation, some of which are complex. For example in some cases around 37,000 non-coding RNAs can be activated by a single impulse.

Characteristics Relevant to Prognosis

The characteristic can be responsiveness to tyrosine kinase inhibitor therapy. The characteristic can be abnormal expression from a kinase gene and/or from a tyrosine kinase gene, for example the characteristic can be upregulation of tyrosine kinase expression. Kinases which are known to be relevant to prognosis for cancer include receptor tyrosine kinases (e.g. PDGFRA) which are on the cell surface, non-receptor kinases, cytoplasmic tyrosine kinases (e.g. ABL1) and serine/threonine kinases. The characteristic can be abnormal expression from a kinase gene which is responsive to or which encodes a gene product which is responsive to a known inhibitor, e.g. a tyrosine kinase inhibitor. The characteristic can be genetic or epigenetic change in a gene which is responsive to or which encodes a gene product which is responsive to tyrosine kinase inhibitors. The characteristic can be genetic or epigenetic change in one or more of the following genes: FIP1L1, PDGFRA, Flt3, ABL1, FGFR1 and cKIT.

The characteristic can be responsiveness to drugs which are ATP mimetics. Tyrosine kinase genes (for example ABL1, Brutons, cKIT, FGFR1, PDGFRA and PDGFRB) encode proteins that are sensitive to ATP mimetics.

The characteristic can be the response to a specific treatment and/or prophylaxis (in particular to a specific pharmaceutical treatment and/or prophylaxis), for example a tyrosine kinase inhibitor, optionally where the drug is known to target receptor tyrosine kinases e.g. PDGFRA, preferably one or more from a group comprising Dasatinib, crenolanib, dovitinib and Imatinib. The tyrosine kinase inhibitor may be Cediranib, Crenolanib, Dasatinib (Sprycel); Dovitinib, Imatinib (Gleevec); IMC-3G3 (Olaratumab, LY3012207) Lartruvo (PDGFRA); Masitinib (AB1010), Nilotinib (Tasigna); Pazopanib; PKC412 (midostaurin, CGP41251); Quizartinib; Regorafenib; Sorafenib (Nexavar); Sunitinib (Sutent); Vatalanib; 5116836. The characteristic can predisposition to a specific condition, optionally hypereosinophilia.

Subgroups and Personalised Treatment

As used herein, a "subgroup" preferably refers to a population subgroup (a subgroup in a population), more preferably a subgroup in the population of a particular animal such as a particular eukaryote, or mammal (e.g. human, non-human, non-human primate, or rodent e.g. mouse or rat). Most preferably, a "subgroup" refers to a subgroup in the human population.

The invention includes detecting and treating particular subgroups in a population. Within such subgroups the characteristics discussed herein (such as responsiveness to treatment) will be present or absent. Epigenetic interaction differences on a chromosome are, generally speaking, structural differences which exist at a genomic level. The inventors have discovered that these differ between subsets (for example two or at least two subsets) in a given population. Identifying these differences will allow physicians to categorize their patients as a part of one subset of the population as described in the method. The invention therefore provides physicians with a method of personalizing medicine for the patient based on their epigenetic chromosome interactions, and provide an alternative more effective treatment regime, in particular for subgroups of patients whose prognosis is affected as a result of being identified as part of said subgroup.

Typically a subgroup will be at least 1%, 5%, 10%, 30%, 50% or 80% of the population. The population can be the general population. The population can be the group of cancer patients, where the cancer is optionally any one of the following cancers: iHES, chronic and acute eosinophilic leukemias, chronic myeloid leukemia (CML), acute myeloid leukemia (AML), Acute Lymphocytic Leukemia (ALL), PDGFRA-positive non-small cell lung carcinoma (NSCLC), glioblastoma, including glioblastoma multiforme and astrocytoma, prostate Cancer, advanced ovarian cancer, gastrointestinal stromal tumour (GIST) and renal cell carcinoma. One of more subgroups can have any of the above listed cancers, and the method of determining prognosis for a cancer can be carried out on a subject with any of the above cancers.

Generating Ligated Nucleic Acids

Certain embodiments of the invention utilise ligated nucleic acids, in particular ligated DNA. These comprise sequences from both of the regions that come together in a chromosome interaction and therefore provide information about the interaction. The EpiSwitch™ method described herein uses generation of such ligated nucleic acids to detect chromosome interactions.

Thus a method of the invention may comprise a step of generating ligated nucleic acids (e.g. DNA) by:

(i) in vitro crosslinking of epigenetic chromosomal interactions present at the chromosomal locus;

(ii) optionally isolating the cross-linked DNA from said chromosomal locus;

(iii) subjecting said cross-linked DNA to cutting, for example by restriction digestion with an enzyme that cuts it at least once (in particular an enzyme that cuts at least once within said chromosomal locus);

(iv) ligating said cross-linked cleaved DNA ends (in particular to form DNA loops); and (v) identifying the presence of said ligated DNA and/or said DNA loops, in particular using techniques such as PCR (polymerase chain reaction), to identify the presence of a specific chromosomal interaction.

PCR may be used to detect or identify the ligated nucleic acid, for example the size of the PCR product produced may be indicative of the specific chromosome interaction which is present, and may therefore be used to identify the status of the locus. The skilled person will be aware of numerous restriction enzymes which can be used to cut the DNA within the chromosomal locus of interest. It will be apparent that the particular enzyme used will depend upon the locus studied and the sequence of the DNA located therein. A non-limiting example of a restriction enzyme which can be used to cut the DNA as described in the present invention is TaqI.

Embodiments Such as EpiSwitch™ Technology

The EpiSwitch™ Technology relates to the use of microarray EpiSwitch™ marker data in the detection of epigenetic chromosome conformation signatures specific for phenotypes. Embodiments such as EpiSwitch™ which utilise ligated nucleic acids in the manner described herein have several advantages. They have a low level of stochastic noise, for example because the nucleic acid sequences from the first set of nucleic acids of the present invention either hybridise or fail to hybridise with the second set of nucleic acids. This provides a binary result permitting a relatively simple way to measure a complex mechanism at the epigenetic level. EpiSwitch™ technology also has fast processing time and low cost. In one embodiment the processing time is 3 to 6 hours.

Samples and Sample Treatment

The sample will contain DNA from the individual. It will normally contain cells. In one embodiment a sample is obtained by minimally invasive means, and may for example be blood. DNA may be extracted and cut up with a standard restriction enzyme. This can pre-determine which chromosome conformations are retained and will be detected with the EpiSwitch™ platforms. In one embodiment wherein the sample is a blood sample previously obtained from the patient, the described method is advantageous because the procedure is minimally invasive. Due to the synchronisation of chromosome interactions between tissues and blood, including horizontal transfer, a blood sample can be used to detect the chromosome interactions in tissues, such as tissues relevant to disease. For certain conditions, such as cancer, genetic noise due to mutations can affect the chromosome interaction 'signal' in the relevant tissues and therefore using blood is advantageous.

Properties of Nucleic Acids Relevant to the Invention

The nucleic acids which are made or detected in the embodiments of the invention may be the same as, or have any of the properties of, the first and second nucleic acids mentioned herein. The nucleic acids of the invention typically comprise two portions each comprising sequence from one of the two regions of the chromosome which come together in the chromosome interaction. Typically each portion is at least 8, 10, 15, 20, 30 or 40 nucleotides in length, for example 10 to 40 nucleotides in length. Preferred nucleic acids comprise sequence from any of the genes mentioned in any of the tables. Preferred nucleic acids bind any specific probe or primer sequence mentioned herein. Preferably the nucleic acids are DNA. It is understood that where a specific sequence is defined the invention may use the complementary sequence as required in the particular embodiment.

The Second Set of Nucleic Acids—the 'Index' Sequences

The second set of nucleic acid sequences has the function of being a set of index sequences, and is essentially a set of nucleic acid sequences which are suitable for identifying subgroup specific sequence. They can represent the 'background' chromosomal interactions and might be selected in some way or be unselected. They are in general a subset of all possible chromosomal interactions.

The second set of nucleic acids may be derived by any suitable method. They can be derived computationally or they may be based on chromosome interaction in individuals. They typically represent a larger population group than the first set of nucleic acids. In one particular embodiment, the second set of nucleic acids represents all possible epigenetic chromosomal interactions in a specific set of genes. In another particular embodiment, the second set of nucleic acids represents a large proportion of all possible epigenetic chromosomal interactions present in a population described herein. In one particular embodiment, the second set of nucleic acids represents at least 50% or at least 80% of epigenetic chromosomal interactions in at least 20, 50, 100 or 500 genes, for example in 20 to 100 or 50 to 500 genes.

The second set of nucleic acids typically represents at least 100 possible epigenetic chromosome interactions which optionally modify, regulate or in any way mediate a disease state/phenotype in population. The second set of nucleic acids may represent chromosome interactions that affect a disease state in a species, for example comprising nucleic acids sequences which encode cytokines, kinases, or regulators associated with any disease state, predisposition to a disease or a disease phenotype. The second set of nucleic acids typically comprises sequences representing epigenetic interactions relevant and not relevant to the characteristic that defines the subgroup.

In one particular embodiment the second set of nucleic acids derive at least partially from naturally occurring sequences in a population, and are typically obtained by in silico methods. Said nucleic acids may further comprise single or multiple mutations in comparison to a corresponding portion of nucleic acids present in the naturally occurring nucleic acids. Mutations include deletions, substitutions and/or additions of one or more nucleotide base pairs. In one particular embodiment, the second set of nucleic acids may comprise sequence representing a homologue and/or orthologue with at least 70% sequence identity to the corresponding portion of nucleic acids present in the naturally occurring species. In another particular embodiment, at least 80% sequence identity or at least 90% sequence identity to the corresponding portion of nucleic acids present in the naturally occurring species is provided.

Properties of the Second Set of Nucleic Acids

In one particular embodiment, there are at least 100 different nucleic acid sequences in the second set of nucleic acids, preferably at least 1000, 2000 or 5000 different nucleic acids sequences, with up to 100,000, 1,000,000 or 10,000,000 different nucleic acid sequences. A typical number would be 100 to 1,000,000, such as 1,000 to 100,000 different nucleic acids sequences. All, or at least 90% or at least 50%, of these would correspond to different chromosomal interactions.

In one particular embodiment, the second set of nucleic acids represent chromosome interactions in at least 20 different loci or genes, preferably at least 40 different loci or genes, and more preferably at least 100, at least 500, at least 1000 or at least 5000 different loci or genes, such as 100 to 10,000 different loci or genes. The lengths of the second set of nucleic acids are suitable for them to specifically hybridise according to Watson Crick base pairing to the first set of nucleic acids to allow identification of chromosome interactions specific to subgroups. Typically the second set of nucleic acids will comprise two portions corresponding in sequence to the two chromosome regions which come together in the chromosome interaction. The second set of nucleic acids typically comprise nucleic acid sequences which are at least 10, preferably 20, and preferably still 30 bases (nucleotides) in length. In another embodiment, the nucleic acid sequences may be at the most 500, preferably at most 100, and preferably still at most 50 base pairs in length. In a preferred embodiment, the second set of nucleic acids comprises nucleic acid sequences of between 17 and 25 base pairs. In one embodiment at least 100, 80% or 50% of the second set of nucleic acid sequences have lengths as described above. Preferably the different nucleic acids do not have any overlapping sequences, for example at least 100%, 90%, 80% or 50% of the nucleic acids do not have the same sequence over at least 5 contiguous nucleotides.

Given that the second set of nucleic acids acts as an 'index' then the same set of second nucleic acids may be used with different sets of first nucleic acids which represent subgroups for different characteristics, i.e. the second set of nucleic acids may represent a 'universal' collection of nucleic acids which can be used to identify chromosome interactions relevant to different characteristics.

The First Set of Nucleic Acids

The first set of nucleic acids are normally from individuals known to be in two or more distinct subgroups defined by presence or absence of a characteristic relevant to a prognostic companion epigenetic test, such as any such characteristic mentioned herein. The first nucleic acids may have any of the characteristics and properties of the second set of nucleic acids mentioned herein. The first set of nucleic acids is normally derived from a sample from the individuals which has undergone treatment and processing as described herein, particularly the EpiSwitch™ cross-linking and cleaving steps. Typically the first set of nucleic acids represents all or at least 80% or 50% of the chromosome interactions present in the samples taken from the individuals.

Typically, the first set of nucleic acids represents a smaller population of chromosome interactions across the loci or genes represented by the second set of nucleic acids in comparison to the chromosome interactions represented by second set of nucleic acids, i.e. the second set of nucleic acids is representing a background or index set of interactions in a defined set of loci or genes.

In one embodiment the first set of nucleic acids is labelled, and typically nucleic acids from different subgroups are labelled with different labels. This allows them to be distinguished in a detection method.

Nucleic Acids

Nucleic acids described herein may in the form of a library of nucleic acids which comprises at least 200, at least 500, at least 1000, at least 5000 or at least 10000 different nucleic acids of the invention, such as 'second' nucleic acids. The invention provides a particular library of nucleic acids which typically comprises at least 200 different nucleic acids. The library may be in the form of nucleic acids bound to an array.

Hybridisation

The invention requires a means for allowing wholly or partially complementary nucleic acid sequences from the first set of nucleic acids and the second set of nucleic acids to hybridise. In one embodiment all of the first set of nucleic acids is contacted with all of the second set of nucleic acids in a single assay, i.e. in a single hybridisation step. However any suitable assay can be used.

Labelled Nucleic Acids and Pattern of Hybridisation

The nucleic acids mentioned herein may be labelled, preferably using an independent label such as a fluorophore (fluorescent molecule) or radioactive label which assists detection of successful hybridisation. Certain labels can be detected under UV light. The pattern of hybridisation, for example on an array described herein, represents differences in epigenetic chromosome interactions between the two subgroups, and thus provides a method of comparing epigenetic chromosome interactions and determination of which epigenetic chromosome interactions are specific to a subgroup in the population of the present invention.

The term 'pattern of hybridisation' broadly covers the presence and absence of hybridisation between the first and second set of nucleic acids, i.e. which specific nucleic acids from the first set hybridise to which specific nucleic acids from the second set, and so it not limited to any particular assay or technique, or the need to have a surface or array on which a 'pattern' can be detected.

Specific Conditions and Selection of Subgroups

By focusing on chromosome interactions, and changes in chromosome interactions, the inventors have identified groups of patients which could respond to potentially life-saving therapeutic diagnostic interventions, for example using tyrosine kinase inhibitors (TKI), who would be missed using conventional diagnostics.

In one embodiment the method of the invention detects responsiveness to tyrosine kinase inhibitor therapy, for example inhibitors which are ATP mimetics. Preferably the responsiveness to tyrosine kinase inhibitor therapy of cancer is detected, for example in patients with elevated eosinophils. Preferably the cancer is iHES, chronic and acute eosinophilic leukemias, acute myeloid leukemia (AML), PDGFRA positive non-small cell lung carcinoma, glioblastoma, including glioblastoma multiforme and astrocytoma, prostate cancer, advanced ovarian cancer or gastrointestinal stromal tumour (GIST). In such embodiments detection of chromosome interactions in PDGFRA and/or FIP1L1 are preferred, such as any specific interaction described herein (for example by references to specific primers and/or probes).

Preferably, the presence or absence of any of the chromosome interactions within any of the relevant genes mentioned herein are detected, for example in at least 1, 2, 3, 4, 5 or 6 of the genes. Preferably the presence or absence of chromosome interactions represented by any specific primer and/or probe sequence disclosed herein is determined in the method. These numbers of genes or chromosome interactions can be used in any of the different embodiments mentioned herein.

The invention provides a method which comprises detecting the presence or absence of chromosome interactions, typically 1 to 5, or 5 to 20, or 5 to 500 such interactions, in order to determine the presence or absence of a characteristic in an individual. Preferably the chromosome interactions are those in any of the genes mentioned herein.

3C Interactions and Cancers

The different embodiments of the invention may relate to any cancer or gene mentioned herein, for example those listed below.

The inventors have discovered 3C interactions in ABL1, Bruton Tyrosine Kinase, cKIT, FGFR1, F1PL1, FLT3 and PDGFRA which are associated with cancer, including breast cancer, ovarian cancer, leukemias, glioma, lymphomas, and carcinomas.

Typically interactions relevant to, or identified using, methods described herein are associated with the any of the following conditions: Acute Myeloid Leukaemia (AML), Chronic Lymphocytic Leukaemia (CLL), Chronic Myeloid Leukemia (CML), CML-blast crisis, Gastrointestinal Stromal Tumor (GIST), Myelodysplastic Syndromes (MDS), Myeloproliferative Disorders (Myeloproliferative Neoplasms, MPN), X-linked agammaglobulinemia (XLA), B cell malignancy, NHL, Lymphoma (all classifications), Myeloma, Recurrent Mature B-Cell Neoplasms, Chronic Graft Versus Host Disease, Relapsed Hairy Cell Leukemia, Relapsed or Refractory Solid Tumors, Refractory Mantle Cell Lymphoma, Amplified Oesophagogastric Carcinoma, Rheumatoid Arthritis, Mastocytosis, Mast Cell Leukemia, Prostate Tumours, Advanced Melanoma, mutated Malignant Melanoma, 2nd Line, Unresectable or Metastatic Gastrointestinal Stromal Tumors (GIST), Expressing Malignant Mesothelioma, Advanced, Platinum-Refractory Ovarian Cancer, Relapsed Ovarian Epithelial, Fallopian Tube, or Primary Peritoneal Cancer, Ovarian Low Malignant Potential Tumor, Uterine Papillary Serous Carcinoma, extensive-Stage Small Cell Lung Cancer, locally Advanced Nasopharyngeal Carcinoma, relapsed/Refractory Non-Hodgkin's Lymphoma, Metastatic Renal Cell Cancer, Metastatic Gastroenteropancreatic Neuroendocrine Tumor, recurrent Ovarian Clear Cell Carcinoma, Esophageal Squamous Cell Carcinoma, Persistent Uterine Cancer, Breast tumours, Thyroid cancer, Oral adenoma, Acute Leukaemia, Prostate Tumours, Translocated FGFR1-3, Mutated, or Amplified Recurrent Head and Neck Cancer, Recurrent Malignant Glioma expressing the FGFR-TACC Gene Fusion, Advanced Non-Small Cell Lung Cancer.

In one embodiment interactions relevant to, or identified using, methods described herein are associated with the any of the following conditions: iHES, Non-small Cell Lung Cancer (NSCLC), Colorectal Cancer, Metastatic Melanoma, Renal Cell Cancer, Refractory Hodgkin's Lymphoma, Previously Treated Ovarian Cancer, Locally Advanced Nasopharyngeal Carcinoma, Refractory Chronic Lymphocytic Leukemia/Small Lymphocytic Lymphoma (CLL/SLL), Sumitinib-failed Gastrointestinal Stromal Tumors (GIST). Preferred conditions are Glioma, Acute Myeloid Leukaemia and Breast Cancer, iHES and Chronic Leukaemias.

Interactions in ABL1, cytoplasmic tyrosine kinase gene, for example located at 9q34, are associated with the following diseases: Acute Myeloid Leukaemia (AML), Chronic Lymphocytic Leukaemia (CLL), Breast Cancer, (GIST), Myelodysplastic Syndromes (MDS) or Myeloproliferative Disorders (Myeloproliferative Neoplasms, MPN).

Interactions in Bruton Tyrosine Kinase, cytoplasmic tyrosine kinase gene, for example located at Xq22.1, are associated with the following diseases: X-linked agammaglobulinemia (XLA), B cell malignancy, NHL, Lymphoma (all classifications), Myeloma, Chronic Lymphocytic Leukemia, Recurrent Mature B-Cell Neoplasms, Chronic Graft Versus Host Disease, Relapsed Hairy Cell Leukemia, Relapsed or Refractory Solid Tumors, Refractory Mantle Cell Lymphoma, Amplified Oesophagogastric Carcinoma and Rheumatoid Arthritis.

Interactions in cKIT, receptor tyrosine kinase gene, for example located at 4q12, are associated with the following diseases: Mastocytosis and Mast Cell Leukemia and Prostate Tumours, Advanced Melanoma, mutated Malignant Melanoma, 2nd Line Unresectable or Metastatic Gastrointestinal Stromal Tumors (GIST), Expressing Malignant Mesothelioma. Advanced, Platinum-Refractory Ovarian Cancer, Relapsed Ovarian Epithelial, Fallopian Tube, or Primary Peritoneal Cancer, or Ovarian Low Malignant Potential Tumor, extensive-Stage Small Cell Lung Cancer, locally Advanced Nasopharyngeal Carcinoma, relapsed/Refractory Non-Hodgkin's Lymphoma, Metastatic Renal Cell Cancer, Metastatic Gastroenteropancreatic Neuroendocrine Tumor, recurrent Ovarian Clear Cell Carcinoma, Esophageal Squamous Cell Carcinoma, Persistent Uterine Cancer and Breast tumours.

Interactions in FGFR1, receptor tyrosine kinase gene, for example located at 8p11, are associated with the following diseases: Thyroid cancer, Oral adenoma, Chronic Leukaemia, Acute Leukaemia, Prostate Tumours and Breast Cancer, Translocated FGFR1-3, Mutated, or Amplified Recurrent Head and Neck Cancer, Recurrent Malignant Glioma expressing the FGFR-TACC Gene Fusion, Advanced Non-Small Cell Lung Cancer.

Interactions in FIP1L1, polyadenylation specificity factor frequently fused to PDGFRA (for example 4q12) are associated with the following disease: iHES, Chronic Leukaemias.

Interactions in FLT3 receptor tyrosine kinase gene, for example located at 13q11-12.2, are associated with the following diseases: Chronic Leukaemia's, Acute Myeloid Leukaemia and Breast Cancer, iHES, Chronic Leukaemias, Non-small Cell Lung Cancer (NSCLC), Colorectal Cancer, Metastatic Melanoma or Renal Cell Cancer, Glioma, Refractory Hodgkin'S Lymphoma, previously Treated Ovarian Cancer, Locally Advanced Nasopharyngeal Carcinoma, Refractory Chronic Lymphocytic Leukemia/Small Lymphocytic Lymphoma (CLL/SLL), Sumitinib-failed Gastrointestinal Stromal Tumors (GIST).

Interactions in PDGFRA a receptor tyrosine kinase gene, for example located at 4q12, are associated with the following diseases: Glioma, Chronic Leukaemias, Acute Myeloid Leukaemia, Breast Cancer, iHES.

The Individual that is Tested

The individual to be tested may or may not have any symptoms of any disease condition or characteristic mentioned herein. The individual may be at risk of any such condition or characteristic. The individual may be at risk because of the characteristic. The individual may have a worse prognosis because of the characteristic and may require therapy specific to the characteristic. The individual may have recovered or be in the process of recovering from the condition or characteristic. The individual is preferably a mammal, such as a primate, human, non-human mammal or rodent. The individual may be male or female. The individual may be 30 years old or older. The individual may be 29 years old or younger.

Any of the genes, loci, regions and nucleic acids discussed here can be of, or from, any of the types of individuals mentioned herein.

Preferred Gene Regions, Loci, Genes and Chromosome Interactions

For all aspects of the invention preferred gene regions, loci, genes and chromosome interactions are mentioned herein. Typically in the methods of the invention chromosome interactions are detected from at least 1, 2, 3, 4, 5, or 6 of the relevant genes listed herein. Preferably the presence or absence of at least 1, 2, 3, 4, 5 or 6 of the relevant specific chromosome interactions represented by the primer and/or probe sequences mentioned herein is detected.

The region may be upstream or downstream of any of the genes mentioned herein, for example 50 kb upstream or 20 kb downstream, for example from the coding sequence.

In one embodiment the chromosome interactions which are detected are present at any of the positions or in any of the regions shown in the tables. In the case where ligated products are detected in the method then sequence shown in any of the primer or probe sequences disclosed herein may be detected. Thus typically sequence from both regions of the ligated product (i.e. from both sites of the chromosome interaction) could be detected. In preferred embodiments primer and/or probes are used in the method which comprise or consist of the same or complementary sequence to a primer and/or probe disclosed herein. In some embodiments primers and/or probes are used which comprise sequence which is homologous to any of the primer and/or probe sequences shown herein.

Detection of a Ligated Product by Quantitative PCR (qPCR)

In one embodiment a ligated sequence which is relevant to a chromosomal interaction is detected quantitatively, for example using fluorescence detection. This embodiment can be carried out on any ligated sequence disclosed herein or which is relevant to the typing/detection methods disclosed herein, but is not restricted to such sequences or methods. Thus the embodiment relating to qPCR can be carried out to detect any ligated sequence which comprises sequences from regions of chromosomes that have been brought together in any chromosome interaction, which may have any of the characteristics mentioned herein.

Thus the invention provides a method for quantitatively detecting a ligated sequence which is relevant to a chromosome interaction using a probe which is detectable upon activation during a PCR reaction, wherein said ligated sequence comprises sequences from two chromosome regions that come together in an epigenetic chromosome interaction, wherein said method comprises contacting the ligated sequence with the probe during a PCR reaction, and detecting the extent of activation of the probe, and wherein said probe binds the ligation site.

The primer and probe sequences may be any such specific sequence disclosed or homologues and/or fragments of the specific sequences. The primer sequences are typically capable of amplifying the ligated product made in the process of detecting a chromosome interaction, such as a 3C or EpiSwitch™ method, for example any such method or ligated product described herein. The primers are typically unidirectional. Optionally, the primer sequences are designed to be unique for the ligated product of the 3C interaction in question. The probe is typically capable of specifically binding a sequence in the ligated product which includes the ligation site. The probe is typically a 'hydrolysis' probe from which one or more moieties may be cleaved/released in order to activate a label during the PCR reaction.

The ligated sequence can be prepared by crosslinking a sample of nucleic acid, followed by breaking the nucleic acid into smaller pieces, e.g. by enzyme digest or by a physical shearing process. A ligation step is then performed. The ligated sequence is typically derived from a sample from an individual or a cell line which has undergone treatment and processing as described herein, particularly the EpiSwitch™ cross-linking and cleaving steps. The ligated sequence can be a ligated product as defined in or made by any of the above methods. The ligation site of the ligated sequence may comprise the restriction enzyme recognition sequence of the restriction enzyme used to cut the crosslinked nucleic acid. A preferred restriction enzyme is TaqI or any modified form of TaqI (which for example recognises the same restriction site). The ligated DNA molecule can comprise a nucleic acid sequence of length 10 to 100 to nucleotide bases, or 10 to 400 nucleotide bases, or 10 to 500 nucleotide bases, or 200 to 600 nucleotide bases, or 200 to 800 nucleotide bases or 200 to 1000 nucleotide bases.

Preferably only one set of primers (i.e. two PCR primers capable together of amplification) is used in the detection, and a nested PCR with more than one set of primers is not performed. Preferably the primers are unidirectional. Even more preferably, the primer sequence is chosen so that it is unique for the 3C interaction in question. In one embodiment the detection method is performed in the presence of other nucleic acids (such as other ligated products) which are not amplified and/or to which the probe does not bind. Typically other nucleic acids (such as ligated products) may represent at least 10%, 30% or at least 50% of the nucleic acids or ligated products which are present.

Situations Detected by the qPCR

The qPCR method described herein may be used to detect chromosome interactions in any situation where they are relevant, for example any situation described in. It will typically be used to detect a chromosome interaction associated with a subgroup, for example as defined herein. It may be used detect a change in a chromosome interaction and/or a chromosome interaction associated with a mutation, change in expression from a gene or deregulation of a gene.

The qPCR method described herein may be used to detect chromosome interactions where the sequences from two chromosome regions that come together in an epigenetic chromosome interaction lie at least 1000 base pairs apart or at least 10,000 base pairs apart or at least 100,000 base pairs apart in the chromosome. The qPCR method described herein may be used to detect long range chromosome interactions where the sequences from two chromosome regions that come together in an epigenetic chromosome interaction lie greater than 100,000 base pairs apart and the interaction therefore generates a DNA loop greater than 100 kilobases, optionally greater than 500 kilobases, preferably greater than 900 kilobases. The qPCR method described herein may be used to detect long range chromosome interactions associated with a genetic or epigenetic change in genes responsive to tyrosine kinase inhibitor therapy, such as PDGFRA.

Design/Structure of a qPCR Probe

The probe for use in the qPCR reaction may be designed to bind specifically to the ligated DNA molecule in the vicinity of the ligation site, at a site on the ligated DNA molecule which comprises the ligation site, optionally having sequence that is complementary to sequence from each of said chromosome regions. The probe spans the junction of both fragments, and for example has sequence that binds at least 5, 10 or 20 nucleotide bases 5' and 3' to the ligation site. The probe may comprise a nucleic acid sequence of length 10 to 40 nucleotide bases, or preferably comprise nucleic acid sequences of length 10 to 35 nucleotide bases, or more preferably comprise nucleic acid sequences of length 20 to 30 nucleotide bases. The probe can have a sequence which has at least 70% homology/identity to the sequence of the ligated DNA molecule or other levels of identity as defined herein.

Labelling of a qPCR Probe

The probe is generally labelled with a detectable label which has an inactive and active state, so that it is only detected when activated. The extent of activation will be related to the extent of template (ligation product) present in the PCR reaction. Detection may be carried out during all or some of the PCR, for example for at least 50% or 80% of the cycles of the PCR.

The probe can comprise a fluorophore covalently attached to one end of the oligonucleotide, and a quencher attached to the other end of the nucleotide, so that the fluorescence of the fluorophore is quenched by the quencher. In one embodiment the fluorophore is attached to the 5'end of the oligonucleotide, and the quencher is covalently attached to the 3' end of the oligonucleotide. Fluorophores that can be used in the methods of the invention include FAM, TET, JOE, Yakima Yellow, HEX, Cyanine3, ATTO 550, TAMRA, ROX, Texas Red, Cyanine 3.5, LC610, LC 640, ATTO 647N, Cyanine 5, Cyanine 5.5 and ATTO 680. Quenchers that can be used with the appropriate fluorophore include TAM, BHQ1, DAB, Eclip, BHQ2 and BBQ650, optionally wherein said fluorophore is selected from HEX, Texas Red and FAM. Preferred combinations of fluorophore and quencher include FAM with BHQ1 and Texas Red with BHQ2. Other preferred combinations are shown in Table 3.

Use of the Probe in a qPCR Assay

Hydrolysis probes of the invention are typically temperature gradient optimised with concentration matched negative controls. Preferably single-step PCR reactions are optimized. More preferably a standard curve is calculated. An advantage of using a specific probe that binds across the junction of the ligated sequence is that specificity for the ligated sequence can be achieved without using a nested PCR approach. The methods described herein allow accurate and precise quantification of low copy number targets. The target ligated sequence can be purified, for example gel-purified, prior to temperature gradient optimization. The target ligated sequence can be sequenced. Preferably PCR reactions are performed using about 10 ng, or 5 to 15 ng, or 10 to 20 ng, or 10 to 50 ng, or 10 to 200 ng template DNA. Forward and reverse primers are designed such that one primer binds to the sequence of one of the chromosome regions represented in the ligated DNA sequence, and the other primer binds to other chromosome region represented in the ligated DNA sequence, for example, by being complementary to the sequence.

Choice of Ligated DNA Target

The invention provides a method of selecting primers and a probe for use in a PCR method as defined herein comprising selecting primers based on their ability to bind and amplify the ligated sequence and selecting the probe sequence based properties of the target sequence to which it will bind, in particular the curvature of the target sequence.

Probes are typically designed/chosen to bind to ligated sequences which are juxtaposed restriction fragments spanning the restriction site. In one embodiment of the invention, the predicted curvature of possible ligated sequences relevant to a particular chromosome interaction is calculated, for example using a specific algorithm referenced herein. The curvature can be expressed as degrees per helical turn, e.g. 10.5° per helical turn. Ligated sequences are selected for targeting where the ligated sequence has a curvature propensity peak score of at least 5° per helical turn, typically at least 10°, 15° or 20° per helical turn, for example 5° to 20° per helical turn. Preferably the curvature propensity score per helical turn is calculated for at least 20, 50, 100, 200 or 400 bases, such as for 20 to 400 bases upstream and/or downstream of the ligation site. Thus in one embodiment the target sequence in the ligated product has any of these levels of curvature. Target sequences can also be chosen based on lowest thermodynamic structure free energy.

Preferred Embodiments for Sample Preparation and Chromosome Interaction Detection Methods of preparing samples and detecting chromosome conformations are described herein. Optimised (non-conventional) versions of these methods can be used, for example as described in this section.

Typically the sample will contain at least $2 \times 10^5$ cells. The sample may contain up to $5 \times 10^5$ cells. In one embodiment, the sample will contain $2 \times 10^5$ to $5.5 \times 10^5$ cells Crosslinking of epigenetic chromosomal interactions present at the chromosomal locus is described herein. This may be performed before cell lysis takes place. Cell lysis may be performed for 3 to 7 minutes, such as 4 to 6 or about 5 minutes. In some embodiments, cell lysis is performed for at least 5 minutes and for less than 10 minutes.

Digesting DNA with a restriction enzyme is described herein. Typically, DNA restriction is performed at about 55° C. to about 70° C., such as for about 65° C., for a period of about 10 to 30 minutes, such as about 20 minutes.

Preferably a frequent cutter restriction enzyme is used which results in fragments of ligated DNA with an average fragment size up to 4000 base pair. Optionally the restriction enzyme results in fragments of ligated DNA have an average fragment size of about 200 to 300 base pairs, such as about 256 base pairs. In one embodiment, the typical fragment size is from 200 base pairs to 4,000 base pairs, such as 400 to 2,000 or 500 to 1,000 base pairs.

In one embodiment of the EpiSwitch method a DNA precipitation step is not performed between the DNA restriction digest step and the DNA ligation step.

DNA ligation is described herein. Typically the DNA ligation is performed for 5 to 30 minutes, such as about 10 minutes.

The protein in the sample may be digested enzymatically, for example using a proteinase, optionally Proteinase K. The protein may be enzymatically digested for a period of about 30 minutes to 1 hour, for example for about 45 minutes. In one embodiment after digestion of the protein, for example Proteinase K digestion, there is no cross-link reversal or phenol DNA extraction step.

In one embodiment PCR detection is capable of detecting a single copy of the ligated nucleic acid, preferably with a binary read-out for presence/absence of the ligated nucleic acid.

Therapy and Identifying Therapeutic Agents

The inventors have discovered how chromosome interactions relate to therapy of cancer, including how compounds used in the treatment of cancer can also act directly on 3C chromosome conformations. For example, the ATP mimetic imatinib, known to act directly on activated tyrosine kinases, has been found act directly on 3C chromosome conformations in imatinib responsive genes such as cKIT.

Identifying or monitoring a change in chromosome conformation associated with the target of a known therapeutic agent can therefore be used to identify compounds which result in the same change in conformation and have the same therapeutic effect. Identifying or monitoring a change in chromosome conformation associated with the target of a known therapeutic agent can therefore be used to identify subjects, or cells, that are susceptible to treatment by the therapeutic agent or other therapeutic agents which can also cause the change in chromosome conformation.

Further the invention provides therapeutic nucleic acids which can be used to prevent or treat cancer by altering a relevant chromosome interaction, for example as mentioned herein. Such a nucleic acid may be DNA or RNA, and may function by 'interference' such as RNAi.

Homologues and Fragments

The invention includes use of homologues and/or fragments of nucleic acids mentioned here, including the specific sequences disclosed herein. Such homologues and/or fragments may have the same binding properties as the original nucleic acid, for example being capable of specifically binding the relevant ligated product.

Homologues of polynucleotide/nucleic acid (e.g. DNA) typically have at least 70% homology, preferably at least 80%, at least 85%, at least 90%, at least 95%, at least 97%, at least 98% or at least 99% homology, for example over a region of at least 10, 15, 20, 30, 100 or more contiguous nucleotides, or across the portion of the nucleic acid which is from the region of the chromosome involved in the chromosome interaction. The homology may be calculated on the basis of nucleotide identity (sometimes referred to as "hard homology").

For example the UWGCG Package provides the BEST-FIT program which can be used to calculate homology and/or % sequence identity (for example used on its default settings) (Devereux et al (1984) Nucleic Acids Research 12, p 387-395). The PILEUP and BLAST algorithms can be used to calculate homology and/or % sequence identity and/or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10.

Software for performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W5 T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two polynucleotide sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs by 1, 2, 3, 4 or more bases, such as less than 10, 15 or 20 bases (which may be substitutions, deletions or insertions of nucleotides). These changes may be measured across any of the regions mentioned above in relation to calculating homology and/or % sequence identity.

Fragments typically have lengths which are at least 90%, 80% or 50% of the original sequence. They may have a truncation of at least 5, 8 or 10 nucleotides from the 5' and/or 3' end.

Arrays

The second set of nucleic acids may be bound to an array, and in one embodiment there are at least 15,000, 45,000, 100,000 or 250,000 different second nucleic acids bound to the array, which preferably represent at least 300, 900, 2000 or 5000 loci. In one embodiment one, or more, or all of the different populations of second nucleic acids are bound to more than one distinct region of the array, in effect repeated on the array allowing for error detection. The array may be based on an Agilent SurePrint G3 Custom CGH microarray platform. Detection of binding of first nucleic acids to the array may be performed by a dual colour system.

Therapeutic Agents

Therapeutic agents are mentioned herein. The invention provides such agents for use in preventing or treating the relevant condition. This may comprise administering to an individual in need a therapeutically effective amount of the agent. The methods of the invention may be used to select an individual for treatment. The methods of the invention, and in particular the method for carrying out a prognostic companion epigenetic test, may include a treatment step where a person identified by the method may then be administered with an agent that prevents or treats the relevant condition for example a tyrosine kinase inhibitor, preferably one from the group of known tyrosine kinase inhibitors which includes Cediranib, Crenolanib, Dasatinib (Sprycel); Dovitinib, Imatinib (Gleevec); IMC-3G3 (Olaratumab, LY3012207) Lartruvo (PDGFRA); Masitinib (AB1010), Nilotinib (Tasigna); Pazopanib; PKC412 (midostaurin, CGP41251); Quizartinib; Regorafenib; Sorafenib (Nexavar); Sunitinib (Sutent); Vatalanib; 5116836, more preferably one or more from a group comprising Dasatinib, crenolanib, dovitinib and Imatinib.

The formulation of the agent will depend upon the nature of the agent. The agent will be provided in the form of a pharmaceutical composition containing the agent and a pharmaceutically acceptable carrier or diluent. Suitable carriers and diluents include isotonic saline solutions, for example phosphate-buffered saline. Typical oral dosage compositions include tablets, capsules, liquid solutions and liquid suspensions. The agent may be formulated for parenteral, intravenous, intramuscular, subcutaneous, transdermal or oral administration.

The dose of an agent may be determined according to various parameters, especially according to the substance used; the age, weight and condition of the individual to be treated; the route of administration; and the required regimen. A physician will be able to determine the required route of administration and dosage for any particular agent. A suitable dose may however be from 0.1 to 100 mg/kg body weight such as 1 to 40 mg/kg body weight, for example, to be taken from 1 to 3 times daily.

Forms of the Substance Mentioned Herein

Any of the substances, such as nucleic acids or therapeutic agents, mentioned herein may be in purified or isolated form. The may be in a form which is different from that found in nature, for example they may be present in combination with other substance with which they do not occur in nature. The nucleic acids (including portions of sequences defined herein) may have sequences which are different to those found in nature, for example having at least 1, 2, 3, 4 or more nucleotide changes in the sequence as described in the section on homology. The nucleic acids may have heterologous sequence at the 5' or 3' end. The nucleic acids may be chemically different from those found in nature, for example they may be modified in some way, but preferably are still capable of Watson-Crick base pairing. Where appropriate the nucleic acids will be provided in double stranded or single stranded form. The invention provides all of the specific nucleic acid sequences mentioned herein in single or double stranded form, and thus includes the complementary strand to any sequence which is disclosed.

The invention also provides a kit for carrying out any process of the invention, including detection of a chromosomal interaction associated with a particular subgroup. Such a kit can include a specific binding agent capable of detecting the relevant chromosomal interaction, such as agents capable of detecting a ligated nucleic acid generated by processes of the invention. Preferred agents present in the kit include probes capable of hybridising to the ligated nucleic acid or primer pairs, for example the hydrolysable probes as described herein, capable of amplifying the ligated nucleic acid in a PCR reaction or a qPCR reaction.

The invention also provides a device that is capable of detecting the relevant chromosome interactions. The device preferably comprises any specific binding agents, probe or primer pair capable of detecting the chromosome interaction, such as any such agent, probe or primer pair described herein.

The nucleic acids mentioned herein may be in the form of DNA.

Specific Embodiments

The EpiSwitch™ platform technology detects epigenetic regulatory signatures of regulatory changes between normal and abnormal conditions at loci. The EpiSwitch™ platform identifies and monitors the fundamental epigenetic level of gene regulation associated with regulatory high order structures of human chromosomes also known as chromosome conformation signatures. Chromosome signatures are a distinct primary step in a cascade of gene deregulation. They are high order biomarkers with a unique set of advantages against biomarker platforms that utilize late epigenetic and gene expression biomarkers, such as DNA methylation and RNA profiling.

EpiSwitch™ Array Assay

The custom EpiSwitch™ array-screening platforms come in 4 densities of, 15K, 45K, 100K, and 250K unique chromosome conformations, each chimeric fragment is repeated on the arrays 4 times, making the effective densities 60K, 180K, 400K and 1 Million respectively.

Custom Designed EpiSwitch™ Arrays

The 15K EpiSwitch™ array can screen the whole genome including around 300 loci interrogated with the EpiSwitch™ Biomarker discovery technology. The EpiSwitch™ array is built on the Agilent SurePrint G3 Custom CGH microarray platform; this technology offers 4 densities, 60K, 180K, 400K and 1 Million probes. The density per array is reduced to 15K, 45K, 100K and 250K as each EpiSwitch™ probe is presented as a quadruplicate, thus allowing for statistical evaluation of the reproducibility. The average number of potential EpiSwitch™ markers interrogated per genetic loci is 50; as such the numbers of loci that can be investigated are 300, 900, 2000, and 5000.

EpiSwitch™ Custom Array Pipeline

The EpiSwitch™ array is a dual colour system with one set of samples, after EpiSwitch™ library generation, labelled in Cy5 and the other of sample (controls) to be compared/analyzed labelled in Cy3. The arrays are scanned using the Agilent SureScan Scanner and the resultant features extracted using the Agilent Feature Extraction software. The data is then processed using the EpiSwitch™ array processing scripts in R. The arrays are processed using standard dual colour packages in Bioconductor in R: Limma*. The normalisation of the arrays is done using the normalised within Arrays function in Limma* and this is done to the on chip Agilent positive controls and EpiSwitch™ positive controls. The data is filtered based on the Agilent Flag calls, the Agilent control probes are removed and the technical replicate probes are averaged, in order for them to be analysed using Limma*. The probes are modelled based on their difference between the 2 scenarios being compared and then corrected by using False Discovery Rate. Probes with Coefficient of Variation (CV)<=30% that are <=-1.1 or =>1.1 and pass the p<=0.1 FDR p-value are used for further screening. To reduce the probe set further Multiple Factor Analysis is performed using the FactorMineR package in R.

* Note: LIMMA is Linear Models and Empirical Bayes Processes for Assessing Differential Expression in Microarray Experiments. Limma is a R package for the analysis of gene expression data arising from microarray or RNA-Seq.

The pool of probes is initially selected based on adjusted p-value, FC and CV<30% (arbitrary cut off point) parameters for final picking. Further analyses and the final list are drawn based only on the first two parameters (adj. p-value; FC).

Statistical Pipeline

EpiSwitch™ screening arrays are processed using the EpiSwitch™ Analytical Package in R in order to select high value EpiSwitch™ markers for translation on to the EpiSwitch™ PCR platform.

Step 1

Probes are selected based on their corrected p-value (False Discovery Rate, FDR), which is the product of a modified linear regression model. Probes below p-value <=0.1 are selected and then further reduced by their Epigenetic ratio (ER), probes ER have to be <=-1.1 or =>1.1 in order to be selected for further analysis. The last filter is a coefficient of variation (CV), probes have to be below <=0.3.

Step 2

The top 40 markers from the statistical lists are selected based on their ER for selection as markers for PCR translation. The top 20 markers with the highest negative ER load and the top 20 markers with the highest positive ER load form the list.

Step 3

The resultant markers from step 1, the statistically significant probes form the bases of enrichment analysis using hypergeometric enrichment (HE). This analysis enables marker reduction from the significant probe list, and along with the markers from step 2 forms the list of probes translated on to the EpiSwitch™ PCR platform.

The statistical probes are processed by HE to determine which genetic locations have an enrichment of statistically significant probes, indicating which genetic locations are hubs of epigenetic difference.

The most significant enriched loci based on a corrected p-value are selected for probe list generation. Genetic locations below p-value of 0.3 or 0.2 are selected. The statistical probes mapping to these genetic locations, with the markers from step 2, form the high value markers for EpiSwitch™ PCR translation.

Array Design and Processing

1. Genetic loci are processed using the SII software (currently v3.2) to:
    a. Pull out the sequence of the genome at these specific genetic loci (gene sequence with 50 kb upstream and 20 kb downstream)
    b. Define the probability that a sequence within this region is involved in CC's
    c. Cut the sequence using a specific RE
    d. Determine which restriction fragments are likely to interact in a certain orientation
    e. Rank the likelihood of different CC's interacting together.
2. Determine array size and therefore number of probe positions available (x)
3. Pull out x/4 interactions.
4. For each interaction define sequence of 30 bp to restriction site from part 1 and 30 bp to restriction site of part 2. Check those regions aren't repeats, if so exclude and take next interaction down on the list. Join both 30 bp to define probe.
5. Create list of x/4 probes plus defined control probes and replicate 4 times to create list to be created on array
6. Upload list of probes onto Agilent Sure design website for custom CGH array.
7. Use probe group to design Agilent custom CGH array.

Array Processing

1. Process samples using EpiSwitch™ SOP for template production.
2. Clean up with ethanol precipitation by array processing laboratory.
3. Process samples as per Agilent SureTag complete DNA labelling kit—Agilent Oligonucleotide Array-based CGH for Genomic DNA Analysis Enzymatic labelling for Blood, Cells or Tissues
4. Scan using Agilent C Scanner using Agilent feature extraction software.

Publications

The contents of all publications mentioned herein are incorporated by reference into the present specification and may be used to further define the features relevant to the invention.

EXAMPLES

Example 1. Analysis of Chromosome Interactions in Cancer

Introduction

Current oncology diagnosis methods based on genomic DNA are expensive, semi-quantitative and fail to capture all breakpoint variants. Diagnosis methods based on nested RT-PCR require live cells, must be confirmed using other methods and have complex RNA processing step. The method developed in the present work captures all breakpoint variants, is quantitative, has no RNA stability issues, uses small sample volumes and has fast processing time. Thus the method reduces the chance of misdiagnosis and giving the wrong treatment.

The present work also identifies a 3C interaction which is therapeutically responsive to a tyrosine kinase inhibitor. This forms the basis of prognostic test which can be used to detect patients that can be treated with tyrosine kinase inhibitors. Current tests are not accurate or sensitive, for example due to breakpoint variation. Misdiagnosis will lead to patients not receiving tyrosine kinase inhibitor therapy, and instead receiving steroids to which they are unresponsive. Prognosis for untreated patients with iHES for example is poor.

We investigated epigenetic interactions relating to cancer and their utility in the stratification of patients for treatment with tyrosine-kinase inhibitors. Using a high-resolution chromosome-conformation capture or 3C analysis platform known as EpiSwitch™ and quantitative PCR, we mapped, evaluated, and quantified the conformational juxtaposition between FIP1L1 and PDGFRA in glioma-cell lines with and without IDH mutations. Deregulation of PDGFRA by interstitial deletion at 4q12 and fusion to FIP1L1 associated with chronic eosinophilic leukemia prompted our group to also investigate whether the same chromosome-conformation interactions are present in EOL-1 and other leukemic cell lines.

By using a high-resolution chromosome-conformation capture or a 3C analysis platform known as EpiSwitch™ a selection of 3C epigenetic-interactions related to the mutation were identified. To optimize the primers we use a temperature gradient on a 96 well plate assay with the Qiagen QIAgility High-Precision Automated PCR System and tested 72 primers in 36 separate temperature gradient PCRs. A total of 20 individual OBD predicted 3C interactions were screened. Multiple primer sets for each predicted interaction were used when possible. We optimized single step PCRs using 10 ng of target-3C template from two AML cell lines EOL-1 and HL-60. Using SYBR detection and concentration matched negative controls, PCR amplification (of the targets) was performed. The negative controls included EOL-1 without formaldehyde processed as a 3C sample (with digestion and ligation), and normal genomic DNA. All PCR products were run on LabChip. The PCR products of expected size were purified using gel (Invitrogen) and sequenced in the forward and reverse primer orientations. Primers were used at 3.2 pmol/µL per reaction with template concentration of 1 ng/µL per 100 bp. Products showing 100% homology to the predicted 3C fragment were advanced for qPCR design.

To screen for IDH1 SNP rs11554137 and IDH1 R132H mutations, 10 ng of 3C template was used with conventional IDH1 genomic primers derived from academic publications; these primer sequences were designed externally and are not included in this application.

Single step qPCR was performed using hydrolysis-probe based qPCRs with concentration matched negative controls. The detection of the B7 462 bp interaction was then optimized using a hydrolysis probe designed against the junction region of the targeted 3C DNA fragment. The probes used in the qPCR assays are specific for the 3C DNA fragments. A EOL-1 template (10 ng) was used to optimize the probes in a temperature gradient based qPCR (58-68° C.). Primers were selected for hydrolysis probe qPCR assay development. The B7 product was used to design a 3C fragment specific qPCR. A dual label hydrolysis probe, labeled with 5'-FAM/BHQ1-3' or 5'Texas Red/BHQ2-3', was used to detect the sequenced interaction. The probe was designed to span the junctional region of the 3C fragment thereby ensuring the detection of the 3C product was specific for the FIP1L1 and PDGFRA interaction. A qPCR standard curve ($10^6$-1 copy) was produced from the sequenced product.

A dual label 5'FAM-BHQ1-3' labelled hydrolysis probe was used to detect the sequenced interaction. All samples were screened at 20 ng and MMP1 copy number recorded. The sequenced PCR product B7 was used to generate standard curves for qPCR screening. The qPCR templates, adjusted to 20 ng of 3C library DNA, were used with concentration-matched negative controls. Controls included 3C libraries derived from adipose biopsies and normal blood. Additional negative controls included cell line material without formaldehyde fixation, digested and ligated library material, and normal genomic DNA. This study was performed according to the American Society of Hematology's guidelines. Cell lines were provided by the ATCC. Patient material with ethical consent was provided by Tissue Solutions (Oxford BioDynamics TSD-OBD2273).

Of the six FIP1L1—PDGFRA 3C sequence orientations sequences identified, two reoccurred (Table 1). Specifically the genomic sequence labeled GBA461 GB_GBA496A6 was identified four times. Genomic sequence FH147946_FH149AA7 was identified twice. Using single-step PCR, these six interactions were amplified in the AML cell line EOL-1. The FIP1L1 PDGFRA 3C B7 interaction was found reproducibly in the AML cell line (acute myeloid eosinophilic leukemia) EOL-1 (n=2, hydrolysis probe assays) using single step PCR. The loss of the topological insulation between FIP1L1 and PDGFRA in EOL-1 may in part be mediated by deletion.

The 462 base pair B7 interaction was amplified in two imatinib-sensitive cell lines: GDM-1 (n=1) and HL-60 (n=2). The mechanism of topological insulation loss between the FIP1L1 and PDGFRA genes is unknown, however, both cell lines respond to imatinib. The glioblastoma cell lines DBTRG-05MG (n=2 qPCR assays) and U-373 (n=1 qPCR assay) are also positive for the B7 interaction. The maximum copy number found in DBTRG-05MG was 29.89 copies (20 ng of template, Table 2).One glioma sample with no identified IDH1 mutation or SNP rs11554137 had 1.19 (per 20 ng) of FIPL1-PDGFRA 3C fragments. Two glioma samples with identified IDH1 R132H mutation were positive for FIPL1-PDGFRA 3C fragments.

The qPCR standard curves ($10^6$-1 copy) were produced from the sequenced PCR products. Analysis of the qPCR data was performed using the CFX manager software (Bio-Rad). Normalization was performed with a stable 3C interaction in MMP1. The standard curves showed selective amplification of the B7 interaction in AML and glioblastoma samples using single step qPCR.

The use of chromosome conformation successfully detected DNA sequences related to the loss of insulator function between FLIPL1 and PDGFRA in glioblastoma and AML-cell lines. Loss of insulation between the FIP1L1 and PDGFRA genes leads to a 3C alteration that is detectable in AML and glioblastoma using qPCR. These interactions would be undetectable using conventional sequencing methodology.

Example 2. The Development of Quantitative PCR Assays

To comply with the data and technical requirements for qPCR addressed in the MIQE guidelines we developed novel techniques for amplification and detection of 3C using qPCR. Quantitative real-time PCR (qPCR) permits the determination of DNA copy number at high sensitivity in target samples. This was found to be particularly suited to the demands of analysis of nucleic acids products relating to detection of chromosome interactions.

MIQE guidelines provide specifications for the minimum information that must be reported for a qPCR experiment to ensure its relevance, accuracy, correct interpretation, and repeatability. MIQE (Minimum Information for Publication of Quantitative Real-Time PCR Experiments) is modelled on similar guidelines drawn up for DNA microarray analysis, proteomics experiments, genome sequence specification, and those under discussion for RNA interference work and metabolomics, all of which are initiatives coordinated under the umbrella of MIBBI (Minimum Information for Biological and Biomedical Investigations)

Conventionally in 3C analysis in the instances where a fluorescence based PCR approach is used then multiple primer sets are designed in a defined 'constant' region of complex DNA of the 3C fragment. However such approaches do not adhere to the MIQE principles for qPCR, and are technically a derivation of nested PCR. Such approaches require at least one half of the interaction to be known.

In conventional detection techniques the DNA polymerase cleaves only probes that are hybridized to the known DNA target and if the reverse PCR primer binds to the same 3C library fragment. The increase in fluorescence occurs only if the target is complementary to the probe and is amplified during PCR. Because of these requirements, non-specific amplification is not detected.

From the quantity of genomic DNA required to detect ligation products, we estimate that some locus-specific ligation events may occur in only $\frac{1}{2,000}$ to $\frac{1}{20,000}$ mammalian cells. Therefore, reliable quantification of ligation products with conventional approaches is possible only if large amounts of DNA (i.e., many genome equivalents) are added to each PCR in conventional techniques. However we routinely use 20-100 ng of 3C template ($\sim 3.2 \times 10^4$-$1.6 \times 10^5$ genome equivalents) per PCR with the new technique we have developed. Our technology requires 3C hydrolysable probes to bind over the ligation junction. This also microarray analysis to be compatible with PCR analysis.

Why does the existing technology does not work using conventional techniques? Technical issues relating to specificity of detection and quantification of 3C copy number.

The conventional approach requires two set of primers, and two rounds of PCR. Technically this is a derivative of nested PCR with florescence based detection. Other approaches mimic this, but with one primer set and between forty-fifty cycles of PCR. While differences may be seen between samples the approach cannot be described as quantitative and contains a number of serious technical issues:

(a) Nested PCR is accepted as non-quantitative, efficiency differences between primer sets and the PCRs reaching the plateau phase in some reactions make accurate and precise quantification of low copy number impossible.
(b) Non-specific products can be amplified with nested primers.
(c) The assays are often not sequenced.
(d) With the two round PCR approach no 'true,' absolute quantification regarding copy number can be obtained from the data.
(e) Standard curves are not constructed (which require one round of PCR), making accurate and precise quantification of low copy number impossible.
(f) Existing kits do not comply with the guidelines established for safe clinical qPCR assays.
(g) TaqMan PCRs frequently amplify multiple PCR products raising serious technical issues with regards the specificity of the product.
(h) With respect to point (g) the use of hydrolysis probes for the detection of 3C, the probes are located in the 'constant region'.
(i) The constant region is not a sequence specific area for both the 3C fragments or the TaqI site—any specificity claim that the PCR product detected by the hydrolysis probe is a 3C fragment is therefore dubious.

Conventional Approaches Use the Following Controls:

Control 1. Make a control template that contains all ligation products in equal amounts. Use this template to normalize for differences in primer efficiency.

Control 2. Determine interactions between sites separated by increasing genomic distances to estimate the frequency of random interactions. A good starting point would be to test about a dozen interactions between sites separated by genomic distances ranging from 0 to 100 kb.

Control 3. When comparing two different cell types or two different conditions, determine interactions in a genomic region that is assumed to have a similar conformation in the two cases. Use this dataset for normalization so that data obtained from the region of interest can be quantitatively compared.

A specific interaction is detected when after normalization for primer efficiency (control 1), a local peak in interaction frequency is observed (control 2). Analysis of an unrelated genomic region (control 3) can then be used to compare different cells or cell state to establish whether the specific interaction is correlated with biological activities such as transcription of the locus.

However the technique we have developed does not require such controls to be in place. Specific amplification and detection is achieved due to the choice of binding targets of the primers and probe, combined with use of a fluorescence quencher labelling system. For example Table 3 lists some suitable fluorescent probes and quenchers.

Example 3. Characteristics of the Target Sequences

EpiSwitch™ qPCR technology uniquely utilizes for detection of the target hydrolysis probes spanning across a TaqI restriction site in ligated juxtaposed DNA fragments (Table 4). Normally, the sites chosen for detection with hydrolysis probes are chosen for the efficiency of hybridization against the probe and their propensity for formation of secondary structures and other biophysical properties that might interfere with probe hybridization process, including folding and bending properties and minimum free energy levels. This explains why, so far, any use of hydrolysis probes in the context of 3C detection targeted the probes within one part of the ligation fragment and did not overlap both. This strongly undermines specificity of the detection for only the ligated products vs all the ligated and unligated fragments within the target sequence.

The curvature of DNA and minimum free energy levels at the ligated juxtapositions of Check Point Charlie (CC) sites around TaqI restriction site indicate the secondary structure conformation differentiating conventional targeted sequences for hydrolysis probe hybridization. Probes are designed on the juxtaposed TaqI fragments spanning the restriction site. The curvature of DNA is calculated by BEND algorithm[1] by summing up the roll, tilt and twist angles of dinucleotide geometrics. The curvature is expressed as degrees per helical turn, e.g., 10.5° per helical turn or 1° per base pair. The minimum free energy, $\Delta G$, at the TaqI restriction site is calculated by Zuker[2] algorithm with the estimation of energy minimization using nearest neighbour energy parameters[3].

In EpiSwitch™ technology we scan up to 400 bases of upstream and downstream sequences from the TaqI site and calculate the curvature of the DNA. In consequence of ligating together two CC of high secondary structure, the sequences targeted at the ligation sites show quantitative difference in the curvature propensity in comparison to conventional target sequences for hydrolysis probe hybridization. The technology looks for a curvature propensity peak score of above >5° per helical turn. The values compared to the valley of neighbouring sequences below 5° per helical turn might show the DNA may adopt a curved conformation.

Also, we scan up to 20 bases of upstream and downstream sequences of the TaqI restriction site and calculate the minimum free energy, $\Delta G$, of linear DNA at 60° C. in the ionic conditions of 0 mM $Na^+$ and 4.5 mM $M^{++}$ with oligo correction as described in Zuker algorithm. The sequence with the thermodynamic structure with the free energy levels below <1.15 kcal/mol at 60° C. are selected for probe design.

Such sequences residing in a regulatory region of a gene like promoter, introns, terminators indicate a secondary structure conformation, identified by the EpiSwitch™ platform by calculating the curvature and free energy values. Probes were designed spanning the TaqI restriction site on the sequences selected with the curvature propensity and minimum free energy levels described above.

While conventional use of hydrolysis probes would not utilize to targeted hybridization such biophysically constrained sequences at the ligated junctures of CC sites, in the context of EpiSwitch processing and detection we are able to use hydrolysis probes specifically for the TaqI ligation site overlap with all the qPCR controls demonstrating efficient and proportionate detection of the ligated products by copy numbers against non-specific controls. This is first practical use of hydrolysis probes targeting 3C overlap, performed due and in the context of EpiSwitch assay, designed on the basis of the temperature gradient testing for the effective probe detection.

The examples below illustrate the methodology:

Sequence 1

(SEQ ID NO: 1)
TTCCACGTGGCCTACCACAGCATGTCAGGCCTGGGGGCAGAATCTTGCCAT

ACTGTGCAGCCCAAATTTGAATGCCAAAGGCTTTCGTTTGTCTCTGGGGGG

CCACAGTCTAGGTCTAGTTCTGTGCAGGAGTTGTAATATTTGCTCTTCTCT

CCCTCCTCCAGCTCGCAGACCTCTGAAGAGAGTGCCATTGAGACGGGTTCC

AGCAGTTCCACCTTCATCAAGAGAGAGGACGAGACCATTGAAGACATCGAA

AAGATAAAACAGGTGTTAGTGAGGATATGGGGAAATAAAACCCTCATACAC

TTCTGGTGGGATTGTAAAATGGTGCAGCTGCTTTGAAGAACAGCCTGGCCA

TTTTCTCAAATGGTGAAACATGGAGTTACCATGTGAGTCCTCCACCTTAGA

GGAATGAAAACATATTCAGACAAAAACTTGTACGTGAATATTCATAGCAGC

ATTATTCTTAATAGAAAGTGGAAAAAGAAAACCTCGCAGCTG

The curvature propensity profile of the sequence is plotted below. Here the profile shows a curvature propensity magnitude of above 5° between 50 and 100 bases and followed by a valley of low scores. This indicates a curvature conformation of the DNA. The DNA folding and free energy estimation of the sequence surrounding the TaqI region yielded the lowest thermodynamic structure free energy, $\Delta G$, of 1.13 kcal/mol at 60° C., 4.5 mM $Mg^{++}$ ionic condition. This region corresponds to the intronic region of FIP1L1 and 3' end of PDGFRA genes indicating a highly regulated region. This juxtaposed TaqI fragment was selected and a probe was designed spanning the restriction site. The TaqI restriction site in the sequence is shown in white on a black background.

Sequence 2

(SEQ ID NO: 2)
TGGGAGTGGGTGGAGTGAGAACCTGGGAGAAGGCCAGCCCTTTATATCCAG

GCAGACAGCTCCAAGTGCCACCATGGATCAGCCAGTCTTGCAGGGGTGATG

CTATTCAGCTACAGATGGCTTGATCCTGAGTCATTTCTTCCTTTTCCATGC

AGTGTGTCCACCGTGATCTGGCTGCTCGCAACGTCCTCCTGGCACAAGGAA

AAATTGTGAAGATCTGTGACTTTGGCCTGGCCAGAGACATCATGCATGATT

CGAAAAGATAAAACAGGTGTTAGTGAGGATATGGGGAAATAAAACCCTCAT

ACACTTCTGGTGGGATTGTAAAATGGTGCAGCTGCTTTGAAGAACAGCCTG

GCCATTTTCTCAAATGGTGAAACATGGAGTTACCATGTGAGTCCTCCACCT

TAGAGGAATGAAAACATATTCAGACAAAAACTTGTACGTGAATATTCATAG

CAGCATTATTCTTAATAGAAAGTGGAAAAAGAAAACCTCGCAGCTGCATCA

ACTGATGAATGGATAGATTAAATGTGTTATATCCATACAGCGGAATATTAT

TTGGCAAGGACAATAAAATGAAGTACTGGTAGATGTTACAACACGGATGAA

CCTTACAAATGTGGAAGCTAAAGATGTCAGTCCGT

A scan of 647 bp of sequences around TaqI of two juxtaposed fragments show a curvature propensity magnitude of above 5° per helical turn at position approx. 210 bp surrounding a valley of low scores. The DNA folding and free energy estimation of 44 bp sequence surrounding the TaqI region yielded the lowest thermodynamic structure free energy, $\Delta G$, of 0.78 kcal/mol at 60° C., 4.5 mM $Mg^{++}$ ionic condition.

Sequence 3

(SEQ ID NO: 3)
GCAGCTGCGAGGTTTTCTTTTTCCACTTTCTATTAAGAATAATGCTGCTAT

GAATATTCACGTACAAGTTTTTGTCTGAATATGTTTTCATTCCTCTAAGGT

```
GGAGGACTCACATGGTAACTCCATGTTTCACCATTTGAGAAAATGGCCAGG

CTGTTCTTCAAAGCAGCTGCACCATTTTACAATCCCACCAGAAGTGTATGA

GGGTTTTATTTCCCCATATCCTCACTAACACCTGTTTTATCTTTTCGAGGT

CCTTGCTGAACCTGGACCTATAAATGACGTCAATGATAGTGATCCCTACTG

CAGAAATCTACAAGTGGCTATAAAGAACTCTGTAGGTAAGAAATTCTGTAA

GATCAGAAAGTACAATGAATTCACTTCATAATAAATTACTTGGTGGACACC

AAATGGGTGCTAAATTGATTGGGTAGAAGGAATTGTATGCCCAAGCCACAT

GGC
```

A scan of 462 bp of sequences spanning upstream and downstream of TaqI restriction site showed approx. between 400 and 450 bp, the propensity magnitude of above 5° per helical turn with surrounding sequences values below 5° per helical turn. The DNA folding and free energy estimation of 44 bp sequence surrounding the TaqI region yielded the lowest thermodynamic structure free energy, ΔG, of −0.93 kcal/mol at 60° C., 4.5 mM $Mg^{++}$ ionic condition.

Sequence 4
(SEQ ID NO: 4)
```
AGTACTTCCTCTCCCCTCCCATATTGTTAAAAATAGTTTACATTGCTTCCC

AGGCTGGGCTGGTGGAGTTGGCACGAGATGTCAGAGGAACCTGAGTCATGC

TCAGGCCCAAGCCCTGTTGGCAGGCAGACCACTGCTTTCTGGCCTTCCGTG

ACTATCTGAAAAAAATCGTGAATGGCTAGAGCTACTCTTCACTTGCTGAAC

ATTTTCAAAAAGAATTGAGAACTTCTGGATTAAATTGCCTTCTTCCTCGAA

AAGATAAAACAGGTGTTAGTGAGGATATGGGGAAATAAAACCCTCATACAC

TTCTGGTGGGATTGTAAAATGGTGCAGCTGCTTTGAAGAACAGCCTGGCCA

TTTTCTCAAATGGTGAAACATGGAGTTACCATGTGAGTCCTCCACCTTAGA

GGAATGAAAACATATTCAGACAAAAACTTGTACGTGAATATTCATAGCAGC

ATTATTCTTAATAGAAAGTGGAAAAAGAAAACCTCGCAGC
```

A scan of 499 bp of sequences spanning upstream and downstream of TaqI restriction site showed two curvature propensity peaks at approx. 160 and 240 bp. The DNA folding and free energy estimation of 44 bp sequence surrounding the TaqI region yielded the lowest thermodynamic structure free energy, AG, of 1.14 kcal/mol at 60° C., 4.5 mM $M^{++}$ ionic condition.

Sequence 5
(SEQ ID NO: 5)
```
CCTCTCCCACACAAACCTGCTACTGAGTACCTTCGCTAACTTAACCATTCA

TTCACCCTGGAAGACCACCTACTAGCAGAAGGATTCTTAACAAATGTAAAG

AAAGTAAGGACTTTACACTAACAATACAAAACTAACTCTCTCTTTGACAAT

TCAAAAAACAAAAGATGTTGAACTTTGACATTTACAGAATTAAATGTCAAA

TGTGACACAATACCATCACATCTGGCTAACTAACTCTTATGCTTTTTTAG

TAAGGAACAACTTTTGAGCCTCAATATCTTAATTCTTAAAATGATAAAGAA

CACTTAACTCAATTTGTTGAGATCAAATAAGGTAATGTAAAAGTGGGATTT

TTATTTTTACTTATTTATTCGAAAACCCTGGGACCCTTCCAGATGGGACTA

ACTGGGGAAAGTGGACAAGTTACAAACAAAGAAACTCAAAGGAAAGTCATT

GGCACTGATCTCTAAGATGCTATCACATGTGATTGGTGGTTGATTTTATTA

ACAAATTATAAGCAAAGTACTACAAAGGTGGCTTTAAAAAGAAAATAAAGC

AATTCACAGAAACTACTTTTTCATGTAGCTTGTATGTGTGCTCCATGT
```

A scan of 609 bp of sequences spanning upstream and downstream of TaqI restriction site showed two curvature propensity peaks at approx. 200 and 500 bp with a valley of low scores. The DNA folding and free energy estimation of 44 bp sequence surrounding the TaqI region yielded the lowest thermodynamic structure free energy, ΔG, of 0.51 kcal/mol at 60° C., 4.5 mM $M^{++}$ ionic condition.

Sequence 6
(SEQ ID NO: 6)
```
AAATGATGAGGCACGGGTGAATAAGATAGTTGGAAGTGACACATACAGATT

TCAAATAATTCCCTAAAGGTGTATGGTTTTCTTTCCCTACAAATCCTACTT

TCAGTTCTTTTGTACATGGACCCAGAGTGGAATTGCTGGATCATATGATAA

TTCTATTTTTAACTTCTTGATGGACCTCTGTTTTTGTTTTGTTTTTTACAG

AGGCTGCAACATTTTATATTCCTACTAATAATGCACAGGGGTTCGGATTTC

TCCACATCCTTGCCAACACTTGATATTTCCTGGGTTTTTTGATAATGGCCA

TCCTAATAGGTGTGGGGACATGAGGTTTTCAATATGCTTGTGGGACATCGA

AAACCCTGGGACCCTTCCAGATGGGACTAACTGGGGAAAGTGGACAAGTTA

CAAACAAAGAAACTCAAAGGAAAGTCATTGGCACTGATCTCTAAGATGCTA

TCACATGTGATTGGTGGTTGATTTTATTAACAAATTATAAGCAAAGTACTA

CAAAGGTGGCTTTAAAAAGAAAATAAAGCAATTCACAGAAACTACTTTTTC

ATGTAGCTTGTATGTGTGCTCCATG
```

A scan of 586 bp of sequences spanning upstream and downstream of TaqI restriction site showed two curvature propensity peaks at approx. 300 and 500 bp with a valley of low scores. The DNA folding and free energy estimation of 44 bp sequence surrounding the TaqI region yielded the lowest thermodynamic structure free energy, ΔG, of 0.51 kcal/mol at 60° C., 4.5 mM $Mg^+$ ionic condition.

REFERENCES

1. Goodsell, D. S. and Dickerson, R. E. (1994) "Bending and curvature calculations in B-DNA" Nuc. Acids Res. 22, 5497-5503
2. Zuker (2003). Mfold web server for nucleic acid folding and hybridization prediction. Nuc. Acids Res. 31, 3406-3415
3. SantaLucia, Jr (1998) A unified view of polymer, dumbbell and oligonucleotide DNA nearest-neighbor thermodynamics. Proc. Natl. Acad. Sci. USA 95, 1460-1465

TABLE 1a

| Well | Size | ENSEMBL BLAT position FIP1L1 | ENSEMBL BLAT position PDGFRA | Distance (bp) between fragments | Primer 1 | Primer 2 |
|---|---|---|---|---|---|---|
| A1 | 501 | 4: 53379986-53380174* | 4: 54294960-5495285 RF | 914786 | TTCCACGTGGCCTACCACAG (SEQ ID NO: 7) | CAGCTGCAGGTTTTCTTTT (SEQ ID NO: 8) |
| A1 | 647 | 4: 53379986-53380318 | 4: 54285685-54285944 RF | 905367 | TGGGAGTGGGTGGAGTGAGA (SEQ ID NO: 9) | ACGGACTGACATCTTTAGCTTCC (SEQ ID NO: 10) |
| B1 and B7 | 462 | 4: 53379986-53380176 | 4: 54278879-54279091 RR | 898703 | GCAGCTGCGAGGTTTTCTTT (SEQ ID NO: 11) | GCCATGTGGCTTGGGCATAC (SEQ ID NO: 12) |
| C1 | 499 | 4: 53379986-53380194 | 4: 54281532-54281784 RF | 901338 | AGTACTTCTTCTCCCCTCCCA (SEQ ID NO: 13) | GCAGCTGCGAGGTTTTCTTTT (SEQ ID NO: 14) |
| D7 and E7 | 609 | 4: 53361094-53361416 | 4: 54281778-54281990 FR | 920362 | CCTCTCCCACACAAACCTGCTA (SEQ ID NO: 15) | ACATGGAGCACACATACAAGCTAC (SEQ ID NO: 16) |
| D7 | 586 | 4: 53369589-53369898 | 4: 54281778-54282010 FR | 911880 | AAATGATGAGGCACGGGTGAA (SEQ ID NO: 17) | CATGGAGCACACATACAAGCTAC (SEQ ID NO: 18) |

*Sequence from primer

TABLE 1b

Six recurrent FIP1L1 and PDGFRA interactions and base pair (BP) size

| No. | Interaction | Well no | Size in base pairs |
|---|---|---|---|
| 1 | FIP1L1PDGFRA_4_GBA461GB_GBA496A6_ FH15A743_FH161379_RF | A1 | 501 |
| 2 | FIP1L1 and PDGFRA_4_GBA461GB_GBA496A6_FH149644_FH15A108_RF A1 | A1 | 647 |
| 3 | FIP1L1 and PDGFRA_4_GBA461GB_GBA496A6_FH145047_FH147946_RR | B1 and B7 | B1: 462 |
| 4 | FIP1L1 and PDGFRA_4_GBA461GB_GBA496A6_FH145047_FH147946_RF | C1 | 499 |
| 5 | FIP1L1 and PDGFRA_4_GBAAA81A_GBAA7581_FH147946_FH149AA7_FR | D7 and E7 | D7: 609 |
| 6 | FIP1L1 and PDGFRA_4_GBA31931_GBA36063_FH147946_FH149AA7_FR | D7 | 586 |

TABLE 1c

Sequence of ligated fragments

No Sequence

1 TTCCACGTGGCCTACCACAGCATGTCAGGCCTGGGGGCAGAATCTTG
CCATACTGTGCAGCCCAAATTTGAATGCCAAAGGCTTTCGTTTGTCT
CTGGGGGGCCACAGTCTAGGTCTAGTTCTGTGCAGGAGTTGTAATAT
TTGCTCTTCTCTCCCTCCTCAGCTCGCAGACCTCTGAAGAGAGTGC
CATTGAGACGGGTTCCAGCAGTTCCACCTTCATCAAGAGAGAGGACG
AGACCATTGAAGCATCGAAAAGATAAAACAGGTGTTAGTGAGGATA
TGGGGAAATAAAACCCTCATACACTTCTGGTGGGATTGTAAAATGGT
GCAGCTGCTTTGAAGAACAGCCTGGCCATTTTCTCAAATGGTGAAAC
ATGGAGTTACCATGTGAGTCCTCCACCTTAGAGGAATGAAAACATAT
TCAGACAAAAACTTGTACGTGAATATTCATAGCAGCATTATTCTTAA
TAGAAAGTGG (SEQ ID NO: 19)

2 TGGGAGTGGGTGGAGTGAGAACCTGGGAGAAGGCCAGCCCTTTATAT
CCAGGCAGACAGCTCCAAGTGCCACCATGGATCAGCCAGTCTTGCAG
GGGTGATGCTATTCAGCTACAGATGGCTTGATCCTGAGTCATTTCTT
CCTTTTCCATGCAGTGTGTCCACCGTGATCTGGCTGCTCGCAACGTC
CTCCTGGCACAAGGAAAAATTGTGAAGATCTGTGACTTTGGCCTGGC
CAGAGACATCATGCATGATTCGAAAAGATAAAACAGGTGTTAGTGAG
GATATGGGGAAATAAAACCCTCATACACTTCTGGTGGGATTGTAAAA
TGGTGCAGCTGCTTTGAAGAACAGCCTGGCCATTTTCTCAAATGGTG
AAACATGGAGTTACCATGTGAGTCCTCCACCTTAGAGGAATGAAAAC
ATATTCAGACAAAAACTTGTACGTGAATATTCATAGCAGCATTATTC
TTAATAGAAAGTGGAAAAGAAAACCTCGCAGCTGCATCAACTGATG
AATGGATAGATTAAATGTGTTATATCCATACAGCGGAATATATTTG
GCAAGGACAATAAAATGAGTACTGGTAGATGTTACAACACGGATGA
ACCTTACAAATGTGGAAGCTAAAGATGTCAGTCCGT
(SEQ ID NO: 20)

3 GCAGCTGCGAGGTTTTCTTTTTCCACTTTCTATTAAGAATAATGCTG
CTATGAATATTCACGTACAAGTTTTTGTCTGAATATGTTTTCATTCC
TCTAAGGTGGAGGACTCACATGGTAACTCCATGTTTCACCATTTGAG
AAAATGGCCAGGCTGTTCTTCAAAGCAGCTGCACCATTTTACAATCC
CACCAGAAGTGTATGAGGGTTTTATTTCCCCATATCCTCACTAACAC
CTGTTTTATCTTTTCGAGGTCCTTGCTGAACCTGGACCTATAAATGA
CGTCAATGATAGTGATCCCTACTGCAGAAATCTACAAGTGGCTATAA
AGAACTCTGTAGGTAAGAAATTCTGTAAGATCAGAAAGTACAATGAA
TTCACTTCATAATAAATTACTTGGTGGACACCAAATGGGTGCTAAAT
TGATTGGGTAGAAGGAATTGTATGCCCAAGCCACATGGC
(SEQ ID NO: 21)

4 AGTACTTCCTCTCCCCTCCCATATTGTTAAAAATAGTTTACATTGCT
TCCCAGGCTGGGCTGGTGGAGTTGGCACGAGATGTCAGAGGAACCTG
AGTCATGCTCAGGCCCAAGCCCTGTTGGCAGGCAGACCACTGCTTTC
TGGCCTTCCGTGACTATCTGAAAAAAATCGTGAATGGCTAGAGCTAC
TCTTCACTTGCTGAACATTTTCAAAAAGAATTGAGAACTTCTGGATT
AAATTGCCTTCTTCCTCGAAAAGATAAAACAGGTGTTAGTGAGGATA
TGGGGAAATAAAACCCTCATACACTTCTGGTGGGATTGTAAAATGGT
GCAGCTGCTTTGAAGAACAGCCTGGCCATTTTCTCAAATGGTGAAAC
ATGGAGTTACCATGTGAGTCCTCCACCTTAGAGGAATGAAAACATAT
TCAGACAAAAACTTGTACGTGAATATTCATAGCAGCATTATTCTTAA
TAGAAAGTGGAAAAGAAAACCTCGCAGC (SEQ ID NO: 22)

5 CCTCTCCCACACAAACCTGCTACTGAGTACCTTCGCTAACTTAACCA
TTCATTCACCCTGGAAGACCACCTACTAGCAGAAGGATTCTTAACAA
ATGTAAAGAAAGTAAGGACTTTACACTAACAATACAAAACTAACTCT
CTCTTTGACAATTCAAAAAACAAAAGATGTTGAACTTTGACATTTAC

TABLE 1c-continued

Sequence of ligated fragments

| No | Sequence |
|---|---|
| | AGAATTAAATGTCAAATGTGACACAATACCATCACATCTGGCTAACT<br>AACTCTTATGCTTTTTTTAGTAAGGAACAACTTTTGAGCCTCAATAT<br>CTTAATTCTTAAAATGATAAAGAACACTTAACTCAATTTGTTGAGAT<br>CAAATAAGGTAATGTAAAAGTGGGATTTTTATTTTTACTTATTTATT<br>CGAAAACCCTGGGACCCTTCCAGATGGGACTAACTGGGGAAAGTGGA<br>CAAGTTACAAACAAAGAAACTCAAAGGAAAGTCATTGGCACTGATCT<br>CTAAGATGCTATCACATGTGATTGGTGGTTGATTTTATTAACAAATT<br>ATAAGCAAAGTACTACAAAGGTGGCTTTAAAAAGAAAATAAAGCAAT<br>TCACAGAAACTACTTTTTCATGTAGCTTGTATGTGTGCTCCATGT<br>(SEQ ID NO: 23) |
| 6 | AAATGATGAGGCACGGGTGAATAAGATAGTTGGAAGTGACACATACA<br>GATTTCAAATAATTCCCTAAAGGTGTATGGTTTTCTTTCCCTACAAA<br>TCCTACTTTCAGTTCTTTTGTACATGGACCCAGAGTGGAATTGCTGG<br>ATCATATGATAATTCTATTTTTAACTTCTTGATGGACCTCTGTTTTT<br>GTTTTGTTTTTTACAGAGGCTGCAACATTTTATATTCCTACTAATAA<br>TGCACAGGGGTTCGGATTTCTCCACATCCTTGCCAACACTTGATATT<br>TCCTGGGTTTTTTGATAATGGCCATCCTAATAGGTGTGGGGACATGA<br>GGTTTTCAATATGCTTGTGGGACATCGAAAACCCTGGGACCCTTCCA<br>GATGGGACTAACTGGGGAAAGTGGACAAGTTACAAACAAAGAAACTC<br>AAAGGAAAGTCATTGGCACTGATCTCTAAGATGCTATCACATGTGAT<br>TGGTGGTTGATTTTATTAACAAATTATAAGCAAAGTACTACAAAGGT<br>GGCTTTAAAAAGAAAATAAAGCAATTCACAGAAACTACTTTTTCATG<br>TAGCTTGTATGTGTGCTCCATG (SEQ ID NO: 24) |

TABLE 2

| Indication | Cell line or clinical sample | IDH1 SNP rs11554137 status | IDH1 R132H status | FIP1L1-PDGFRA 3C DNA copies in 20 ng (+/−) | MMP1 3C copies in 20 ng |
|---|---|---|---|---|---|
| Acute Myeloid Leukemia (AML) | AML-193 | Wild-type | Wild-type | + (0.04) | 0.37 |
| Anaplastic oligoastrocytoma | BT-412 | Wild-type | R132H** | Not in assay | |
| Glioblastoma multiforme | DBTRG-05MG | Wild-type | Wild-type | + (0.05) | 0.35 |
| AML (Eosinophilic) | EOL-1 | Wild-type | Wild-type | + (0.03) | 0 |
| Acute Myelomonocytic Leukemia | GDM-1 | Wild-type | Wild-type | + (1.99) | 7.3 |
| AML | HL-60 | rs11554137* | Wild-type | + (0.18) | 1.24 |
| AML | KG-1 | rs11554137 | Wild-type | − (0) | 4.2 |
| Glioblastoma Astrocytoma | U-373 | Wild-type | Wild-type | + (2.01) | 1.24 |
| Glioblastoma Astrocytoma | U87 | Wild-type | Wild-type | Not in assay | — |
| Oligodendroglioma | 47436 | Wild-type | R132H | − (0) | 1.89 |
| Oligodendroglioma | 47679 | Wild-type | Wild-type | + (1.19) | 2 |
| Oligodendroglioma | 81600 | Wild-type | R132H | − (0) | 0.96 |
| Oligodendroglioma | 174694 | Wild-type | R132H | + (0.04) | 0.61 |
| Oligodendroglioma | 184263 | Wild-type | Wild-type | + (0.06) | 5.19 |
| Oligoastrocytoma | 30736 | Wild-type | Wild-type | − (0) | 1.12 |
| Adipose Biopsy | 91013A | Wild-type | Wild-type | − (0) | 6.05 |
| Normal Blood | 17153 | Not analysed | Not analysed | − (0) | 4.53 |
| Normal Blood | 17335 | Wild-type | Wild-type | − (0) | 2.18 |
| Normal Blood | 17353 | Wild type | Wild-type | − (0) | 3.09 |

*Previously positive, Dodémont et al., 2011
**Previously positive, Flavahan et al., 2016

TABLE 3

| Flurophore | Abs [nm] | Em [nm] | 3' Quencher |
|---|---|---|---|
| FAM | 495 | 520 | TAM, BHQ1, DAB, Eclip |
| TET | 521 | 536 | TAM, BHQ1 |
| JOE | 520 | 548 | TAM, BHQ1, BHQ2 |
| Yakima Yellow | 530 | 549 | BHQ1, Eclip |
| HEX | 535 | 556 | TAM, BHQ1, BHQ2, Eclip, BBQ650 |
| Cyanine3 | 552 | 570 | BHQ1, BHQ2, BBQ650 |
| ATTO 550 | 554 | 576 | TAM, BHQ2 |
| TAMRA | 544 | 576 | BHQ2 |
| ROX | 575 | 602 | TAM, BHQ2, BBQ650 |
| Texas Red | 583 | 603 | BHQ2, BBQ650 |
| Cyanine3.5 | 588 | 604 | BHQ2 |
| LC 610 | 590 | 610 | BHQ2 |
| LC 640 | 625 | 640 | BHQ2, BBQ650 |
| ATTO 647N | 644 | 669 | BHQ2, BBQ650 |
| Cyanine5 | 649 | 670 | BHQ2, BBQ650 |
| Cyanine5.5 | 675 | 694 | BHQ2, BBQ650 |
| ATTO 680 | 680 | 700 | BBQ650 |

TABLE 4

Details of Probes

| | | |
|---|---|---|
| Probe Name | 45047FPRC | |
| Probe Sequence | 5'-Texas RED-TCAGCAAGGACCTCGAAAAGATAAAACA-BHQ2-3' (SEQ ID NO: 25) | |
| Forward Primer | 5'-GCAGCTGCGAGGTTTTCTTT-3' (SEQ ID NO: 27) | |
| Reverse Primer | 5'-GCCATGTGGCTTGGGCATAC-3' (SEQ ID NO: 29) | |
| Interaction Identifier | B7 462 bp, PCR 8. | |
| Genomic Location | 4:54278879-54279091 | 4:53379986-53380176 |
| Orientation | Forward | Reverse |
| Overlapping genes | RP11-231C18.3, PDGFRA | FIP1L1, RP11-231C18.3 |
| Query start-End | 188-400 | 1-191 |
| Length | 213 | 191 |
| Score | 413 | 368 |
| E-val | 1.6E-115 | 5.6E-102 |
| % ID | 100.00 | 99.48 |
| Probe Name | OBDFH010_03_FAM | |
| Probe Sequence | 5'-FAM-ATTTATTCGAAAACCCTGGGACCC-BHQ1-3' (SEQ ID NO: 26) | |

TABLE 4-continued

Details of Probes

| | | |
|---|---|---|
| Forward Primer | 5'-CCTCTCCCACACAAACCTGCTA-3' (SEQ ID NO: 28) | |
| Reverse Primer | 5'-ACATGGAGCACACATACAAGCTAC-3' (SEQ ID NO: 30) | |
| Interaction Identifier | D6/E7, 609 bp. | |
| Genomic Location | 4:53361094-53361416 | 4:54281778-54281990 |
| Orientation | Forward | Forward |
| Overlapping genes | SCFD2 | RP11-231C18.3, PDGFRA |
| Query start-End | 1-323 | 320-532 |
| Length | 323 | 213 |
| Score | 620 | 412 |
| E-val | 6.5E-178 | 3.9E-115 |
| % ID | 100.00 | 100.00 |

Example 4. Further Work

Detection of ectopic tyrosine kinase activation is currently missed by conventional diagnostic methodology (e.g. sequencing) in multiple indications.

Tyrosine kinase inhibitors e.g dasatinib, imatinib and Ibrutinib/Imbruvica (Janssen-Cilag Ltd) are being developed for numerous malignancies (Chronic) and constitutional disorders. Examples of potential non-malignant indications for Bruton Tyrosine Kinase (BTK) inhibitors include arthritis.

Clinicians require evidence of a molecular lesion in a target tyrosine kinase prior to the prescription of a tyrosine kinase inhibitor. Potentially life-saving therapeutic diagnostic interventions using tyrosine kinase inhibitors (TKI) will be missed using conventional diagnostics.

Aspects of the Invention Relating to Drug Treatment:

(a) Imatinib Therapeutically Targets 3C Conformations:

We demonstrate that the ATP mimetic imatinib known to act on directly activated tyrosine kinases also acts directly on 3C chromosome confirmations in imatinib responsive genes such as cKIT.

(b) GSK Therapeutically Targets 3C Conformations:

Data is provided for the IDH1 inhibitor GSK864 that demonstrates this drug directly inhibits chromosome conformations in multiple cell lines. The stratification of oncology patients for effective treatment can be performed by identifying activating mutations in tyrosine kinase genes and acquired changes in other pathways. Diagnostic procedures that help stratify patients in this manner are of great potential benefit. Conformational changes to the FIP1L1 and PDGFRA enhancer regions upregulate PDGFRA expression in glioma patients with IDH1 R132H mutations. Ectopic PDGFRA over expression is treatable with imatinib.

The following data relates to 3C markers and their use in a functional qPCR assay. ABL1 and cKIT show binary difference between the non-malignant sample and the cell line.

RC=reverse complement. The true reverse primer sequence is adjacent to the RC sequence.

Genes for which 3C Interactions were Identified and the Indications they are Involved in:

1. ABL1, cytoplasmic tyrosine kinase gene located at 9q34: Disease indications: Acute Myeloid Leukaemia (AML), Chronic Lymphocytic Leukaemia (CLL), Breast Cancer. Chronic Myeloid Leukemia (CML) and CML-blast crisis or Gastrointestinal Stromal Tumor (GIST). Myelodysplastic Syndromes (MDS) or Myeloproliferative Disorders (Myeloproliferative Neoplasms, MPN).

2. Bruton Tyrosine Kinase, cytoplasmic tyrosine kinase gene located at Xq22.1: Disease indications:
   X-linked agammaglobulinemia (XLA), B cell malignancy. NHL, Lymphoma (all classifications), Myeloma. Chronic Lymphocytic Leukemia. Patients with Recurrent Mature B-Cell Neoplasms. Chronic Graft Versus Host Disease. Relapsed Hairy Cell Leukemia. Relapsed or Refractory Solid Tumors. Refractory Mantle Cell Lymphoma. Amplified Oesophagogastric Carcinoma and Rheumatoid Arthritis.

3. cKIT, receptor tyrosine kinase gene located at 4q12 disease indications:
   Mastocytosis and Mast Cell Leukaemia and Prostate Tumours. Advanced Melanoma, mutated Malignant Melanoma, 2nd Line. Unresectable or Metastatic Gastrointestinal Stromal Tumors (GIST), Expressing Malignant Mesothelioma. Advanced, Platinum-Refractory Ovarian Cancer. Relapsed Ovarian Epithelial, Fallopian Tube, or Primary Peritoneal Cancer, or Ovarian Low Malignant Potential Tumor. Patients with Uterine Papillary Serous Carcinoma, extensive-Stage Small Cell Lung Cancer, locally Advanced Nasopharyngeal Carcinoma, relapsed/Refractory Non-Hodgkin's Lymphoma. Metastatic Renal Cell Cancer, Metastatic Gastroenteropancreatic Neuroendocrine Tumor, recurrent Ovarian Clear Cell Carcinoma, Esophageal Squamous Cell Carcinoma, Persistent Uterine Cancer and Breast tumours.

4. FGFR1, receptor tyrosine kinase gene located at 8p11: Disease indications: Thyroid cancer, Oral adenoma, Chronic Leukaemia, Acute Leukaemia, Prostate Tumours and Breast Cancer. Translocated FGFR1-3, Mutated, or Amplified Recurrent Head and Neck Cancer. Recurrent Malignant Glioma expressing the FGFR-TACC Gene Fusion. Patients with Advanced Non-Small Cell Lung Cancer.

5. FIP1L1, polyadenylation specificity factor frequently fused to PDGFRA (4q12). The non-tyrosine kinase gene: iHES, Chronic Leukaemia's.

6. FLT3 receptor tyrosine kinase gene located at 13q11-12.2: Disease indications: Chronic Leukaemia's, Acute Myeloid Leukaemia and Breast Cancer, iHES, Chronic Leukaemia's. Non-small Cell Lung Cancer (NSCLC). Colorectal Cancer, Metastatic Melanoma or Renal Cell Cancer, Glioma, Refractory Hodgkin'S Lymphoma. Previously Treated Ovarian Cancer. Locally Advanced Nasopharyngeal Carcinoma. Refractory Chronic Lymphocytic Leukemia/Small Lymphocytic Lymphoma (CLL/SLL). Sumitinib-failed Gastrointestinal Stromal Tumors (GIST).

7. PDGFRA a receptor tyrosine kinase gene located at 4q12: Disease indications: Glioma. Chronic Leukaemia's, Acute Myeloid Leukaemia and Breast Cancer, iHES, Chronic Leukaemia's.

TABLE 5

ABL1 3C interaction No 1.

Name of the interaction: ORF1_9_130700600_130703071_130719461_130720884_FR

Selected sequence for probes. Insert 25 bp region either side of the Taq I junction.
5'-CTTATAGCCTGTCTCTCTTGCTGATCGAGGTTGCAACGAGCTGAGATTGC-3' (SEQ ID NO: 31)

Sequence of forward primer: 5'-TTGGAGTTCCAGGGTGATACTGTC-3' (SEQ ID NO: 32)

Sequence of reverse primer: 5'-ACCAACGCTATTCTTGGCTTCCA-3' (SEQ ID NO: 33)

Position of the PCR sequence BLAT. Please note the first two rows are the true homologies.

| Genomic Location | Overlapping Gene(s) | Orientation | Query start | Query end | Length | Score | E-val | % ID |
|---|---|---|---|---|---|---|---|---|
| 9:130719465-130719839 | ABL1 | Forward | 96 | 470 | 375 | 715 | 2.00E-206 | 99.20 |
| 9:130702984-130703074 | EXOSC2 | Forward | 5 | 95 | 91 | 172 | 6.00E-43 | 96.70 |
| X:136026579-136026620 | SLC9A6 | Reverse | 93 | 137 | 45 | 65 | 1.10E-10 | 93.33 |

A blood based test that discriminates normal and malignant material (CML, CML-BC, CLL, Breast Cancer) using peripheral blood samples. The positive control is the CML blast crisis cell line K562.
Cycle qPCR (W|103). 3C assay sequenced product used for the standard curve. The hydrolysis probe targets the junction of the 3C fragment

>ORF1_9_130700600_130703071_130719461_130720884_FR
(SEQ ID NO: 34)

GCAAGCTCCACCTCCTGGGTTCAAGTGATTCTCCTGCCTCAGCCTCCTGAGTAGCTGGGATTACAGGTGTGCCCCACCAT

GCTCTGCTAATTTATCTATTTTTAGTAGAGATGGGGTTTCACCATGTTGGTCAGGCTGGTCTTGAATTCCTGACCTTGTG

ATCCACCCGCCTCGGCCTCCCAAAGTGCTGGGATTACAGACATGAGACACTGCACCCTGCCCCATTCCTTTTAATCTCCC

TTGGAATTAGCTGTTTGGTTGATTTGGAGTTCCAGGGTGATACTGTCTGAGTCATAAATGATTTATTTGTGAATTTCTGT

GGCTGGTCACGTATTTTGGTCCTGTTTGTATTTCCCTTCCCCTCTCTGTGTCTCCTTATAGCCTGTCTCTCTTGCTGATC

GAGGTTGCAACGAGCTGAGATTGCACGCCACTGCACTCCCAGCCTGGGCGACGGAGTGAGACTCCATCTCANNNNNNNNN

NNNNNNNNNNNNNNNNNNNNNNNTGATGACAGCCCAACCTGTCACTTTTTCAGATCCCTTTTTATGAAAGAATTTGCT

TAAGTTGTGTCTGAAGACAAACCAATTTCTTTGGACCCTGGGTATTCTTTTTCTAAGGGAATACCATGTTATTTTGTGTT

ACAGATTGTTTGCGATCTTTCATAGGCTGATCTTTCTAGAGTTGGTTAATATCCATGTAGGTTAGATTGAAAAACTTGAA

TTCAGAAATGTACGGTGTTGGAGCAGACATGGATCTGGAAGCCAAGAATAGCGTTGGTGTTGTTGTTGATGGTGAATCTG

Lab Chip data shows amplification of a 3C interaction in the normal material (patient 375) but not in the chronic myeloid leukemia blast crisis cell line K562 (68° C. primer annealing temperature). This pattern was also found at annealing temperatures 67.5° C. and 66.4° C. Expected product size: 515 bp.

TABLE 6

ABL 3C interaction No 2.

Name of the interaction: ORF1_9_130700600_130703071_130719461_130720884_RF

Selected sequence for probes (to be tested). Insert 25 bp region either side of the Taq I junction.
5'-GGGCCAAGTGTGACTCTCAGGTTTTCGACCTGCCTCAGCCTCCCAAAGT-3' (SEQ ID NO: 35)

Sequence of forward primer: 5'-ATGCAGGAGGTAAAATGGAGGGT-3' (SEQ ID NO: 36)

Sequence of reverse primer: 5'-CAAAGAGACAGCTCCGTCAGAGA-3' (SEQ ID NO: 37)

Position of the PCR sequence BLAT. Please note the first two rows are the true homologies.

| Genomic Location | Overlapping Gene(s) | Orientation | Query start | Query end | Length | Score | E-val | % ID |
|---|---|---|---|---|---|---|---|---|
| 9:130720517-130720886 | ABL1 | Reverse | 256 | 625 | 370 | 724 | 4.40E-209 | 100.00 |
| 9:130700586-130700859 | EXOSC2 | Reverse | 1 | 273 | 275 | 497 | 7.90E-141 | 97.82 |

A blood based test that discriminates normal and malignant material (CML, CML-BC, CLL, Breast Cancer) using peripheral blood samples.
Cycle qPCR (W|103). 3C assay sequenced product used for the standard curve. The hydrolysis probe targets the junction of the 3C fragment

>ORF1_9_130700600_130703071_130719461_130720884_RF
(SEQ ID NO: 38)

CCACTGCACCAGAGCAAAGAGCAAAAGGAGAGATGCAGGAGGTAAAATGGAGGGTGG-
GAAGAGAATGGCTGAAGGAGAGG

GTGGCCTTATTGGCCCATTTCAAGGATTTTGACTTTGATTCATATGATGTGG-
GAAGGCCTTGGAGAATTTTCCGAGGGGA

CTATACTATCTGATGTATGTTTCAGTATGAAATAGAATCTCTCTGGCTGCTATGATCT-
GAAGGAGGACAAGGGAGCAGGG

ATTCCACGGGGCATTGATTGCACAGAGCCAGGTAAGAGTGATGATGCTTGGAC-
CAAAGTGGTGGCACTGGGTGGAGGGT

CAGAACCGACAAGATTTGCTCTCGGATTAGATGTGGGATATGGGGGTGTGAGAGGGGC-
CAAGTGTGACTCTCAGGTTTTC

GACCTGCCTCAGCCTCCCAAAGTGCTGGGATTACAGGTGTGAGC-
CACCGCACCTGGCCTTCTGTCTGTATTTTTAAAAAA

AAGATATTCATGACAACCAAGGGGAGAGGTAAGGTCACAGTGATGTGCTCTGGGTCAAA-
GATTGTTGAGCCTGGACCATT

GGAGAGGGGAGGAAAAGATGGAGGTGTGGGGTCAAGGG-
GAGAGGCTGCAGAGGACAGGACAGTGTGTGGCCAAGGCTGCT

GTTTGTTCCTTCATCACCCTGGCCAGGCTGAGGTCCAGGCAGTGTTCTCTGACG-
GAGCTGTCTCTTTGCACACGAGGAGC

CTGAAATATGGAAAAGTAAGTCGGGCTCTTGATGTTCCTGTTTGCTGACTGAGACTA-
CAAGGCTATTTTTGAATCCCCAT

Lab Chip data shows amplification of 3C interaction in the normal material (patient 375) but not in the malignant material (derived from the cell line K562) at 67.5° C. Expected product size: 676 bp

TABLE 7

Bruton Tyrosine Kinase 3C interactions No 1:

Name of the interaction: ORF2_X_101355470_101357976_101407183_101408846_FR

Selected sequence for probes.
5'-TTGAGGACAAGGACCTCGAGATACTGCCGAGAAATCC-3' (SEQ ID NO: 39)

Sequence of forward primer. 5'-ATGTTGTCTAACCTGTATGTTCT-3' (SEQ ID NO: 40)

Sequence of reverse primer. 5'-CTTCCTCTGCCGGGTGCTAA-3' (SEQ ID NO: 41)

Position of the PCR sequence BLAT. Please note the first two rows are the true homologies.

TABLE 7-continued

Bruton Tyrosine Kinase 3C interactions No 1:

| Genomic Location | Overlapping Gene(s) | Orientation | Query name | Query start | Query end | Query ori | Length | Score | E-val | % ID |
|---|---|---|---|---|---|---|---|---|---|---|
| X:101407180-101407241(3 bp) | RPL36A-HNRNPH2, GLA | Reverse | Query_1 | 5 | 66 | Forward | 62 | 123 | 3.00E-25 | 100.00 |
| X: (2 bp) 101357937-101357978 | BTK | Reverse | Query_1 | 61 | 102 | Forward | 42 | 83.8 | 3.00E-13 | 100.00 |
| 5:154143558-154143584 | MFAP3 | Forward | Query_1 | 65 | 91 | Forward | 27 | 46.1 | 0.057 | 96.30 |
| 12:41941194-41941215 | | Reverse | Query_1 | 69 | 90 | Forward | 22 | 44.1 | 0.22 | 100.00 |

A blood based test that discriminates normal and malignant material (B-Cell leukaemia) usingperipheral blood samples. Positive control cell line RAMOS (Burkitt's lymphoma line).
Cycle qPCR (W|103). 3C assay sequenced product used for the standard curve. The hydrolysis probetargets the junction of the 3C fragment
B cell malignancies = any malignancy thought to involve the Bruton Tyrosine kinase.

>ORF2_X_101355470_101357976_101407183_101408846_FR
(SEQ ID NO: 42)
ATGAGTCCTGAAACAGAGAGAGAGGTCATG

CTGTTGGTGTGGTGTAGGAGGTGGGATGCC

TCACACATCCTCACTTAAAGCCTCACACTT

CCGGTGTGTATCTTTCTAGTACATTTTGAA

TCCCAGAAGACCTCCATGAACCCACATATT

TCCAGAGGTTTCTCCTCTCACAAAATACTT

TTCAGGGACAAAAAAGAGAAAATACTAATT

GAAATACACTGCCTAACTGAATATATTCCC

ACCTCCCAGCCCAGGCTTAGCTCACATCCT

ACCTTCTTGATGAAGCTGTTCCCCCATATC

CATGCCCTCACTAATGTCTCAGTTTTTAGA

AATTTTACAGTGCTTATAAACTTTCTTCTG

ATGTTGTCTAACCTGTATGTTCTTTGAGGA

CAAGGACCTCGAGATACTGCCGAGAAATCC

ACGACCCCAAAAGGAGAAAAAATGGCACGA

ATCTTAGTTCCCCATTCCTCCTACCCACCC

TAGATGTTCTAACGGTTAGCACCCGGCAGA

GGAAGAGCAGAAGTTCACAAGAAGGGTCTG

Lab Chip data shows amplification of 3C interaction in the cell line only at this annealing temperature. Expected product size: 155 bp.

TABLE 8 cKIT tyrosine kinase interaction No 1:

Name of the interaction: ORF3_4_54711719_54715167_54736749_54740853_FR

Selected sequence for probes (to be tested):
TCACCCAGAATAAGGCTTCTCGATTCTAAGTTCTACAAGA (SEQ ID NO: 43)

Sequence of forward primer (s). cKIT_003 (5'-CAGTGCGGTGGGAGTACTGT-3') (SEQ ID NO: 44)

Sequence of reverse primer (s). cKIT_004 (5'-TTCAGCAGGTGCGTGTTCAG-3') (SEQ ID NO: 45)

Sequence of forward primer (s). cKIT_001 (5'-AGTGCGGTGGGAGTACTGTG-3')* (SEQ ID NO: 46)

Sequence of reverse primer (s). cKIT_002 (5'-ACATTTCAGCAGGTGCGTGT-3')* (SEQ ID NO: 47)

Both primer sets (001/002 and 003/004) amplify the interaction. Position of the PCR sequence BLAT for primer sequence is for cKIT003 and CKIT004 (single step PCR and sequencing data has also been confirmed for the additional primers).

| Genomic Location | Overlapping Gene(s) | Orientation | Query name | Query start | Query end | Query ori | Length | Score | E-val | % ID |
|---|---|---|---|---|---|---|---|---|---|---|
| 4:54714861-54715168 | KIT | Forward | | 1 | 307 | Forward | 308 | 585 | 2.80E-167 | 99.68 |
| 4:54736751-54736823 | KIT | Forward | | 308 | 381 | Forward | 74 | 134 | 1.80E-31 | 98.65 |

A blood based test that discriminates normal and malignant material (EOL1) using peripheral blood samples. The positive control cell line EOLI (eosinophillic leukaemia) and BT142 (Glioma).
Cycle qPCR (W|103). 3C assay sequenced product used for the standard curve. The hydrolysis probe targets the junction of the 3C fragment.
*Please note these primer combinations produce single step products and have not been used for nested PCR.

1>ORF3_4_54711719_54715167_54736749_54740853_FR
(SEQ ID NO:48)
TCCCATTTTGAAAGCTTATCCTTTAATGAC

GAGCTTCAGCCAGTGCGGTGGGAGTACTGT

GATCCTCACGTGGTGGTGACGGGGAGGCAG

ACATTGAGAACTGAAGGGCTCCCTTTGATC

ATTAGCCTTACATAGGATGCCTTTAATGTT

GAGCTAGATTGGAAGCCCAAGTGACTGCTG

AAGTGCACCAAATTAACTCAGAAGTCACCA

ATTTCACTCCATTTATGGAAGGGTATTAAC

AGGGGGTTGAGAAACAATTTAAGGAAATGT

TAAATAATGTATTATTTCCAAATCACTGCA

TCATATAATTAACATCCTACCTGTTGTTAG

CAATTATTTATAGGTCATACAGTATACCAA

AATCAGCCAAAGCAATAAATCACCCAGAAT

AAGGCTTCTCGATTCTAAGTTCTACAAGAT

GATCAAGGAAGGCTTCCGGATGCTCAGCCC

TGAACACGCACCTGCTGAAATGTAAGAGCC

AAAAAATTTTTCCTTTAGGTCACGTTTTCC

CTTTTATTTTTCTTTTTAGAGACAGAAACC

CAGATGTTGAGGGTTTTCATAACACAGTTT

GAAATGTCACTTGGATTCTTTATGACACAC

TGGTCAAATGTCATTTCTGTAGTTTATTTT

CATAATCTCTTGTCACCAAAAATACAGAAA

GTTTCAGTAATATTTCATACATGCAGTGTT

TTATGTTATCTATATGTCAGTCCATATGTC

CAGTTGCATAGCCCTGGAATTATTACTGAA

GTTGCTGGATGCCCATACATTTGAAAACAA

GCTGAGGGCATTGAGGAGGG

Lab Chip data shows amplification of 3C interaction in the normal material but not in the malignant material (derived from the cell line EOL1). The expected product size is 429 bp.

TABLE 9

FGFR1 3C interaction No 1:

Name of the interaction: ORF4_8_38427499_38430449_38480545_38486034_FF

Selected sequence for probes (to be tested). Insert 25 bp region either side of the Taq I junction.
5'-AAACCCCAGCAGCCCCTGCCCAAGTCGAGGGAGCAGCTCCCCACCCAGCCC-3' (SEQ ID NO: 49)

Sequence of forward primer: 5'-AGAAAGAGGCAAAGTTAGGAAGCA-3' (SEQ ID NO: 50)

Sequence of reverse primer: 5'-AAAACAGCAACCTATTCAGAGAGC-3' (SEQ ID NO: 51)

Position of the PCR sequence BLAT. Please note the first two rows are the true homologies.

| Genomic Location | Overlapping Gene(s) | Orientation | Query start | Query end | Length | Score | E-val | % ID |
|---|---|---|---|---|---|---|---|---|
| 8:38430233-38430452 | FGFR1 | Forward | 9 | 228 | 220 | 422 | 2.90E-118 | 97.27 |
| 8:38485833-38486036 | | Reverse | 224 | 427 | 204 | 403 | 2.00E-112 | 100.00 |

A blood based test that discriminates normal and malignant material (Thyroid cancer, Oral adenoma, Chronic Leukaemia, Acute Leukaemia, Prostate Tumours and Breast Cancer) using peripheral blood samples. Positive control cell line CCL30 (squamous cell carcinoma).
Cycle qPCR (W|103). 3C assay sequenced product used for the standard curve. The hydrolysis probe targets the junction of the 3C fragment >ORF4_8_38427499_38430449_38480545_38486034_FF (5)
(SEQ ID NO: 52)
GAGCCGCACCATCCTGGGCATCACTTACTGGAGGCTACTGAGCCAGGGCAGTGGGAATTG-GAGCATGGGTCAG

TGGGGAAAACAGCTGGCTGCCTGGGAACCCCCATCTCTTTTCCACCCCACTCCTC-CAAAAGTCAAAGGAAGAA

AGAGGCAAAGTTAGGAAGCAGCTGTAGCAGCATTAAGCGCATTTCATTTCCCC-CATCCTAAGGGGAAAGGTCG

GCCCTCCCCAGGACTTCTTTGTGTCCGGAGTTGCCCCCTCCCCA-GATGCTCAGTTCTTTGCCAAGATTGCCAC

TTGCCAGAGGAACACCCCATTTCCTTTGGGATAGCTCAGCCT-CACCCTTCCCTAGCAACAGCTGAACAAACCC

-continued

CGCCCCTCAAAACCCCAGCAGCCCCTGCCCAAGTCGAGGGAGCAGCTCCC-
CACCCAGCCCCAGGATCTGGGTC

CAGCAGACCTGGAGAGTCTGCCCTGGCTGCACAGACCGTGGTGGGACTGTCTGGCG-
GAACTGTTGTCTGGAGA

CAATGCAGCCCATGTGACAGGCCTTAATGAGTCCCTTCTGGAATCCCACAATGGC-
CAAGTGGCACAGGCTCTC

TGAATAGGTTGCTGTTTTTCAGCAGTGGCAGGGGCTGTGTTGTGGCAACCTCCTCTCTT-
ATTCAACCTCCGGC

ATCTCTCTTCTTTTCCTTTCTTTCTTACCTTTGTCTTTTATCTACTT-
TAACTCTCCTGTTCCCTTTTGATCTC

TTCCTTCTCCTCCACCCTCCIGATTTCTGTTGTTTCTTAGACACAAAATCGCCCTTCACTCCTGCCCTGT

Lab Chip data shows amplification of 3C interaction in the normal material (patient 375) but not in the malignant material (cell line CCL30) at 68° C. Expected product size: 460 bp.

TABLE 10

FIP1L1 3C interaction No 1:

Name of the interaction:
>FIP1L1PDGFRA_4_54231931_54236063_55143356_55145047_FR

Selected sequence for probes (to be tested).
5'-TATGCTTGTGGGACATCGACAAAAGCAATTATGC-3' (SEQ ID NO: 53)

Sequence of forward primer. 5'-TGGAAGTGACACATACAGATTTCAA-3' (SEQ ID NO: 54)

Sequence of reverse primer. 5'-CTTTCTGCACCGTAGCCAGC-3' (SEQ ID NO: 55)

Position of the PCR sequence BLAT. Please note the first two rows are the true homologies.

| Genomic Location | Overlapping Gene(s) | Orientation | Query start | Query end | Length | Score | E-val | % ID |
| --- | --- | --- | --- | --- | --- | --- | --- | --- |
| 4:53369634-53369898 | | Forward | 10 | 274 | 265 | 517 | 3.00E-143 | 99.62 |
| 4:54277188-54277335 | AC058822.1, PDGFRA | Forward | 271 | 418 | 148 | 293 | 7.00E-76 | 100.00 |
| 10:61991285-61991356 | ARID5B | Forward | 123 | 194 | 72 | 87.7 | 8.00E-14 | 90.28 |
| 10:103537280-103537327 | NEURL1 | Forward | 35 | 82 | 48 | 87.7 | 8.00E-14 | 97.92 |

A blood based test that discriminates normal and malignant material (Acute myeloid leukemia) using peripheral blood samples. Positive control cell line EOLI (Eosinophilic acute leukaemia line).
Cycle qPCR (W|103). 3C assay sequenced product used for the standard curve. The hydrolysis probe targets the junction of the 3C fragment.

>FIP1L1PDGFRA_4_54231931_54236063_
55143356_55145047_FR
(SEQ ID NO: 56)
CAGCTAAAGACTACTTTTCCAAGCCTCTTG

CAGCTAGCTATGGACAAATGATGAGGCACG

GGTGAATAAGATAGTTGGAAGTGACACATA

CAGATTTCAAATAATTCCCTAAAGGTGTAT

GGTTTTCTTTCCCTACAAATCCTACTTTCA

GTTCTTTTGTACATGGACCCAGAGTGGAAT

TGCTGGATCATATGATAATTCTATTTTTAA

CTTCTTGATGGACCTCTGTTTTTGTTTTGT

-continued

TTTTTACAGAGGCTGCAACATTTTATATTC

CTACTAATAATGCACAGGGGTTCGGATTTC

TCCACATCCTTGCCAACACTTGATATTTCC

TGGGTTTTTTGATAATGGCCATCCTAATAG

GTGTGGGGACATGAGGTTTTCAATATGCTT

GTGGGACATCGACAAAAGCAATTATGCTAA

TTTCCTTCCCTGTGGGCTCAATTCCTTTTT

TGACACGATGACTTGGAGGAGTCATTATGA

TTACTCCAAACAGGAAAGACACTCGCCCAG

-continued

CTGTCCGCCCGCAGAGAGCTGGCTACGGTG

CAGAAAGCTGAGGAGGCGTCTGGAGTTTTT

GGGTGTTAATGATTCTGCCTGCCCACAGGT

CGGGTCTTGGGGTCTGGAGCGTTTGGGAAG

GTGGTTGAAGGAACAGCCTATGGATTAAGC

-continued

CGGTCCCAACCTGTCATGAAAGTTGCAGTG

AAGATGCTAAAACGTAAGTGCTCCTTCCTG

GGGATTTTTTGAGCACGGGGATTTTTTGAG

CATGGGGATATTAAGGGAATTTCTCAAAAT

CATGCAGCTAGTAAATAAGA

TABLE 11

FLT3 3C interaction No 1:

Name of the predicted interaction: ORF5_13_28025286_28026644_28116701_28118054_RF Selected sequence for probes (to be tested). Insert 25 bp region either side of the Taq I junction.
5'-CCTCGGCGACAGAGTGAGACTCTGTCGATCTCATTCTTTGGTTTCTGAAC-3' (SEQ ID NO: 57)

Sequence of forward primer: 5'-GGTATGTGCCTGTAGTCCCAACT-3' (SEQ ID NO: 58)

Sequence of reverse primer: 5'-GAAGGATGGTGAAACGCTTACGG-3' (SEQ ID NO: 59)

Position of the PCR sequence BLAT. Please note the first two rows are the true homologies.

| Genomic Location | Overlapping Gene(s) | Orientation | Query start | Query end | Length | Score | E-val | % ID |
|---|---|---|---|---|---|---|---|---|
| 13:28025285-28025376 | FLT3 | Forward | 81 | 172 | 92 | 174 | 1.50E-43 | 96.74 |
| 13:28117987-28118056 | | Forward | 15 | 84 | 70 | 139 | 5.30E-33 | 100.00 |

A blood based test that discriminates normal and malignant material (Acute Myeloid Leukaemia) using peripheral blood samples. Cycle qPCR (W|103). 3C assay sequenced product used for the standard curve. The hydrolysis probe targets the junction of the 3C fragment.

>ORF5_13_28025286_28026644_28116701_28118054_RF (SEQ ID NO: 60)

TAATTGCATCACTGCACTCCAGCCTGGGCAACAGTGAGAACTTGTCT-
TAAAGAAACAAAGCAGGTTCTTTCCT

CTCAGAAGCCCCTCTCTCTTACTAGAGAGAGAGCTGTTCTCCTCTCTCTTTCTTCTAT-
TAAACCTCCGCTCCT

AAAAACA-
CANNNNNNNNNNNNNNNNNNNNNNNNNNNNNNNNNNNNNCCCTAAAAAACTAGCCTGGGCAACATGG

TAAAACCCTGTCTCTA-
CAAAAAACACAAATAAACTAGCCAGGCCTGGTGGTATGTGCCTGTAGTCCCAACTAT

TCAGGGAAGCTGAGGTGGGAGGTTTGCTTGAGACCGGGAAGTCCAGGCTGCAGT-
GAGCCGAGATGGCGCCACT

GCACTCTAGCCTCGGCGACAGAGTGAGACTCTGTCGATCTCATTCTTTGGTTTCT-
GAACTCAGCCCACTTTCC

CTCACATAATACAGATCTTCCCGAGAGTCCCGTAAGCGTTTCAC-
CATCCTTCTTTTTTCCAGTTTGCCTTTGT

AAAGCTCATTTCTTTTTACTGTGAAATTAATAAATAGCAATAATACAAATCTCTTT-
TAAGGTATATAAAAATT

CTTCCCTGAGGAGCTCTGTAGGAATTATAAGTAGATCACGATTCAATTTAT-
TCTAATATACGAGTTTAACCCA

ATTTACAATTTACATATCTTTAGGAAATGGCTTCATGCTTTCAGACCACAAATATTC-
CAAAAGGAATAATTTC

AGTGTATTTAATATTCCAGTGAACAGAACGAATCAAAGGGGCTAAGTACTGACCAGTGGATACTGGTCAC

Lab Chip data—row B. This shows amplification of 3C interaction in the normal material (Patient 376) but not in the malignant material (derived from AML patient 277) at 67.5° C. Expected product size: 223 bp.

TABLE 12

Flt3 3C interaction No 2:

Name of the interaction: ORF5_13_28025286_28026644_28116701_28118054_FF

Selected sequence for probes (to be tested). Insert 25 bp region either side of the Taq I junction.
5'-ACTTTACTGTGTCCCCATCACGTGTCGACAGAGTCTCACTCTGTCGCCGA-3' (SEQ ID NO: 61)

Sequence of forward primer: 5'-CAAGCATCTCTCAGGATCCCCAT-3' (SEQ ID NO: 62)

Sequence of reverse primer: 5'-ACTATTCAGGGAAGCTGAGGTGG-3' (SEQ ID NO: 63)

Position of the PCR sequence BLAT. Please note the first two rows are the true homologies.

| Genomic Location | Overlapping Gene(s) | Orientation | Query start | Query end | Length | Score | E-val | % ID |
|---|---|---|---|---|---|---|---|---|
| 13:28026554-28026646 | FLT3 | Reverse | 66 | 158 | 93 | 180 | 1.60E-45 | 98.92 |
| 13:28117990-28118056 | | Forward | 3 | 69 | 67 | 133 | 3.30E-31 | 100.00 |
| 11:35604073-35604129 | | Forward | 7 | 63 | 57 | 110 | 1.70E-24 | 98.25 |

A blood based test that discriminates normal and malignant material (Acute Myeloid Leukaemia) using peripheral blood samples. Cycle qPCR (W|103). 3C assay sequenced product used for the standard curve. The hydrolysis probe targets the junction of the 3C fragment.

35

No 3 >ORF_5_13_28025286_28026644_28116701_28118054_FF (SEQ ID NO: 64)

NNNNNNNNNNNNNNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNAAGAATGCTCCAAGGCTC

AACGAATGCCTCCATCAGAATGCCTGGGAATCCATTCAGAGAAAGGTGCTACAAAGCCATGATGCTCAAGTAA

TTAGCAAGAAAGTTCAAGGATGAGGAGGAGATCCAGCAAACTCCTACAGCCCTCATTTATGCCCGCTAAAGCA

ATAAATCCCTGCAGGACCAAGCATCTCTCAGGATCCCCATGGATGCGGAGGATATY-
ACACAGAGCAGAGACAAG

GTTACTGCTACTTTACTGTGTCCCCATCACGTGTCGACAGAGTCTCACTCTGTCGCCGAGGCTAGAGTGCAGT

GGCGCCATCTCGGCTCACTGCAGCCTGGACTTCCCGGTCTCAAGCAAACCTCCCACCTCAGCTTCCCTGAATA

GTTGGGACTACAGGCACATACCACCAGGCCTGGCTAGTTTATTTGTGTTTTTTGTAGAGACAGGGTTTTACCA

TGTTGCCCAGGCTAGTTTTTTAGGGNNNNNNNNNNNNNNNNNNNNNNNNNNNNNNNNNNTGTGTTTTTAGG

AGCGGAGGTTTAATAGAAGAZVAGAGAGAG-
GAGAACAGCTCTCTCTCTAGTAAGAGAGAGGGGCTTCTGAGAGG

AAAGAACCTGCTTTGTTTCTTTAAGACAAGTTCTCACTGTTGCCCAGGCTGGAGTGCAGTGATGCAATTA

Lab Chip data shows amplification of 3C interaction in the normal material (Patient 376) but not in the malignant material (Derived from AML patient 277) at 68.0° C. Expected product size: 204 bp.

TABLE 13

FLT3 3C interaction No 3:

Name of the interaction: ORF5_13_28025286_28026644_28116701_28118054_RR

Selected sequence for probes (to be tested). Insert 25 bp region either side of the Taq I junction.
5'-GAGTTCAGAAACCAAAGAATGAGATCGAGTGATTGCTAGGTGATGGACCT-3' (SEQ ID NO: 65)

Sequence of forward primer: 5'-GAAGGATGGTGAAACGCTTACGG-3' (SEQ ID NO: 66)

Sequence of reverse primer: 5'-TGCACCCCAACAGGAGTTTTCTA-3' (SEQ ID NO: 67)

Position of the PCR sequence BLAT. Please note the first two rows are the true homologies.

| Genomic Location | Overlapping Gene(s) | Orientation | Query start | Query end | Length | Score | E-val | % ID |
| --- | --- | --- | --- | --- | --- | --- | --- | --- |
| 13:28116700-28116784 | | Forward | 50 | 134 | 85 | 164 | 1.40E-40 | 98.82 |
| 13:28025280-28025338 | FLT3 | Reverse | 1 | 57 | 59 | 93 | 2.40E-19 | 96.61 |

A blood based test that discriminates normal and malignant material (Acute Myeloid Leukaemia) using peripheral blood samples.
Cycle qPCR (W|103). 3C assay sequenced product used for the standard curve. The hydrolysis probe targets the junction of the 3C fragment.

>ORF5_13_28025286_28026644_28116701_28118054_RR
(SEQ ID NO: 68)

GTGACCAGTATCCACTGGTCAGTACTTAGCCCCTTTGATTCGTTCTGTTCACTGGAATAT-
TAAATACACTGAA

ATTATTCCTTTTGGAATATTTGTGGTCTGAAAGCATGAAGCCATTTCCTAAAGA-
TATGTAAATTGTAAATTGG

GTTAAACTCGTATATTAGAATAAATTGAATCGTGATCTACTTATAATTCCTA-
CAGAGCTCCTCAGGGAAGAAT

TTTTATATACCTTAAAAGAGATTTGTATTATTGCTATTTATTAATTT-
CACAGTAAAAGAAATGAGCTTTACA

AAGGCAAACTGGAAAAAAGAAGGATGGTGAAACGCTTACGGGACTCTCGGGAAGATCTGT-
ATTATGTGAGGGA

AAGTGGGCTGAGTTCAGAAACCAAAGAATGAGATCGAGTGATTGCTAGGT-
GATGGACCTGTAGGGAGAGATCA

CTAGATGAGTTCAGGTGGTAAATAGAAAACTCCTGTTGGGGTGCAGTGAGAGAT-
GAAGGTAGTGAAATGAAAG

GATGGGATCAATTTTATATGAGGGCTTTAATTTGAAATGGGAATTTGGTGATAT-
TCTCAGAGCAGCACAAGT

TTTCATGCCATGGAAAAGCAGCAGGAAAAATGTAAACCTTGCCAATAACACGG-
GAAAGTCTCCAAGGGTGCCC

AGTGACTTACTTGCCTATAAACAAAGCCATTCCTGAGCACTTCTGGCTATGAAATTT-
CAAAATACATGTTTTA

GAGAATTTTACTGACACTTTTATGATTTTAGAGGATAATTTAGATTTCATAAATTTTGTTTCCTTCCCTT

Lab Chip data shows amplification of 3C interaction in the normal material (Patient 376) but not in the malignant material (Derived from AML patient 277) at 68.0° C. Expected product size: 173 bp.

TABLE 14

FLT3 3C interaction: No 4:

Name of the interaction: ORF5_13_28009061_28014204_28025286_28026644_FR

Selected sequence for probes (to be tested). Insert 25 bp region either side of the Taq I junction.
5'-GCTGGAGGATTGCTTGAGCTTGGGAGGTCGATCTCATTCTTTGGTTTCTGAAC-3' (SEQ ID NO: 69)

Sequence of forward primer: 5'-GCTTCTGGAGGCCAGGGATTAT-3' (SEQ ID NO: 70)

Sequence of reverse primer: 5'-AGCCCCTTTGATTCGTTCTGTTC-3' (SEQ ID NO: 71)

Position of the PCR sequence BLAT. Please note the first two rows are the true homologies.

| Genomic Location | Overlapping Gene(s) | Orientation | Query start | Query end | Length | Score | E-val | % ID |
|---|---|---|---|---|---|---|---|---|
| 13:28025286-28025660 | FLT3 | Forward | 325 | 699 | 375 | 723 | 6.80E-209 | 100.00 |
| 13:28013880-28014203 | FLT3 | Forward | 1 | 324 | 324 | 627 | 6.70E-180 | 99.07 |
| X:47532217-47532398 | | Reverse | 132 | 313 | 182 | 267 | 1.10E-71 | 84.07 |

A blood based test that discriminates normal and malignant material (Acute Myeloid Leukaemia) using peripheral blood samples.
Cycle qPCR (W|103). 3C assay sequenced product used for the standard curve. The hydrolysis probe targets the junction of the 3C fragment.

>ORF5_13_28009061_28014204_28025286_28026644_FR
(SEQ ID NO: 72)
CACACTCATGCTTCATAAGAAAGGGCTAGTGGCTTCTGGAGGCCAGGGATTATTTTTATT-
TAGTTTTATTTAG

TTGTCTACTTCACTGCACTGAACTCTTAAGAGCTTTTAATTTATTAATCATTTGGCT-
GAAATCAGGAAAGGTG

TTTTTTTTCCCTAAAAACATTTTTATCAATATGTCTTAGGGCAGGCAGAGGAGCT-
CATGCCCTGTGATCCCAG

CACTTTGGGAGGCTGAGGTGGGGGAATCGCTTGAGCCCAGGAGTTCAA-
GACCAGCCTGGGCAATACAGTGATA

CCCTATTTCTACAAAAAATAAAAAACTTAGCCTGGCGTGGTGCTGCCCTCC-
CATGGTCCTAGCTACTTGGAAG

GCCGTGGCTGGAGGATTGCTTGAGCTTGGGAGGTCGATCTCATTCTTTGGTTTCT-
GAACTCAGCCCACTTTCC

CTCACATAATACAGATCTTCCCGAGAGTCCCGTAAGCGTTTCAC-
CATCCTTCTTTTTTCCAGTTTGCCTTTGT

AAAGCTCATTTCTTTTTACTGTGAAATTAATAAATAGCAATAATACAAATCTCTTT-
TAAGGTATATAAAAATT

CTTCCCTGAGGAGCTCTGTAGGAATTATAAGTAGATCACGATTCAATTTAT-
TCTAATATACGAGTTTAACCCA

ATTTACAATTTACATATCTTTAGGAAATGGCTTCATGCTTTCAGACCACAAATATTC-
CAAAAGGAATAATTTC

AGTGTATTTAATATTCCAGTGAACAGAACGAATCAAAGGGGCTAAGTACTGACCAGTGGATACTGGTCAC

Lab Chip data shows amplification of 3C interaction in the normal material (patient 376) but not in the malignant material (derived from AML patient 277) at 68° C. Expected product size: 742 bp.

Additional Data

Confirmation of the temperature gradient data is provided in the following below. Selected interactions for each gene in alphabetical order are presented below, the average copy for each interaction in 20 ng (per reaction=one well per 96 well plate) is included.

1. ABL1 ABL1-515 SYBR-based qPCR assay of material derived from K562 cell line and normal blood (10 ng/reaction).

K562 shows a reduced average copy number (12.36333, SD+/−15.67294) in 20 ng, compared to copies 33.24667, SD+/−35.04153 per 20 ng in normal blood, (p=0.143245 TTest).

2. Bruton Tyrosine Kinase
ORF2_X_101355470_101357976_101407183_101408846_FR

Cell lines (BT142, EOL1 and HL60) show a reduced average copy number (20.99338 SD+/−43.413166) in 20 ng, compared to copies, 43.83277 SD+/−72.808926 per tong in normal blood, (0.41426 TTest).

3. cKIT experiment: Highly significant difference.
ORF3_4_54711719_54715167_54736749_54740853_FR Malignant cell lines (BT142, EOL1 and HL60) show a reduced average copy number (0.2051355D+/−0.453526) in 20 ng, compared to copies 2.639932 (SD+/−1.742175) per 20 ng in normal blood, (p=0.001294 TTest). This is a highly significant difference between the cell lines and non-malignant samples.

4. FGFR1,
ORF4_8_38427499_38430449_38480545_38486034_F

Malignant cell line CCL30 shows an increased average copy number 2.05 (SD+/−0.843267) in 20 ng, compared to copies 1.242222, (SD+/−1.715319) per 20 ng in normal blood, (p=0.314743 TTest).

5. FIP1L1 experiment
FIP1L1PDGFRA_4_54231931_54236063_55143356_55j145047_FR

Malignant cell lines (BT142, EOL1 and HL60) shows a reduced average copy number 13.07325 (SD+/−19.46042) in 20 ng, compared to copies 32.61117 (SD+/−38.58252) per 20 ng in normal blood, (p=0.147896 TTest).

6. FLT3 experiment:
ORF5_13_28009061_28014204_28025286_28026644_F:
Significant difference Malignant patient material shows a reduced average copy number 0.427619 (SD+/−0.667599) in 20 ng, compared to copies 6.587778, SD+/−7.672794 per 20 ng in normal blood, (p=0.043238 TTest).

Drug Sensitivity and Imatinib

Imatinib (Glivec) shows activity against multiple tyrosine kinases including ABL1, cKIT and PDGFRA. The success of the clinical trials in chronic myeloid leukaemia provided the impetus for the identification of a pharmacogenetic strategy.

Example of novel data regarding the action of imatinib in the following imatinib responsive selected gene is described below. 20 ng of template was added to each well for samples treated with imatinib.

cKIT interaction named above (ORF3_4_54711719_54715167_54736749_54740853_FR) and imatinib:

cKIT and exemplary data. The BT142 cells have been treated with 1 μm of imatinib. 20 ng of template was loaded into each well. Please note for the cKIT 3C interaction is completely absent in the imatinib treated cell lines (see below).

The product in well C1 has been confirmed as the cKIT interaction named above (ORF3_4_54711719_54715167_54736749_54740853_FR). This data illustrate direct action of imatinib on a cKIT 3C chromosome conformation.

The MMP1 interaction in the BT142 cell line is shown below. This confirms the quality of the samples. This is a hydrolysis probe based assay.

| Cell line | Cq | MMP1 copy number |
|---|---|---|
| BT142 ctrl | 37.29354288 | 12.16144613 |
| BT142 ctrl | 35.68147305 | 36.19699893 |
| BT142 ctrl | 36.33204621 | 23.30823893 |
| BT142 Imatinib (IM) 1 μM | 35.6402365 | 37.2211193 |
| BT142 1 μM | 36.14604001 | 26.43413752 |
| BT142 1 μM | 35.88943195 | 31.44606744 |

The Action of GSK864 on the Treated Cells Lines

MMP-1 3C quantification with no-fixation controls and a formaldehyde treated samples. The exemplary cell lines used in this application are:

(a) DBTRG-05MG (glioblastoma).

(b) HL-60 (acute myeloid leukaemia).

Figure 8:
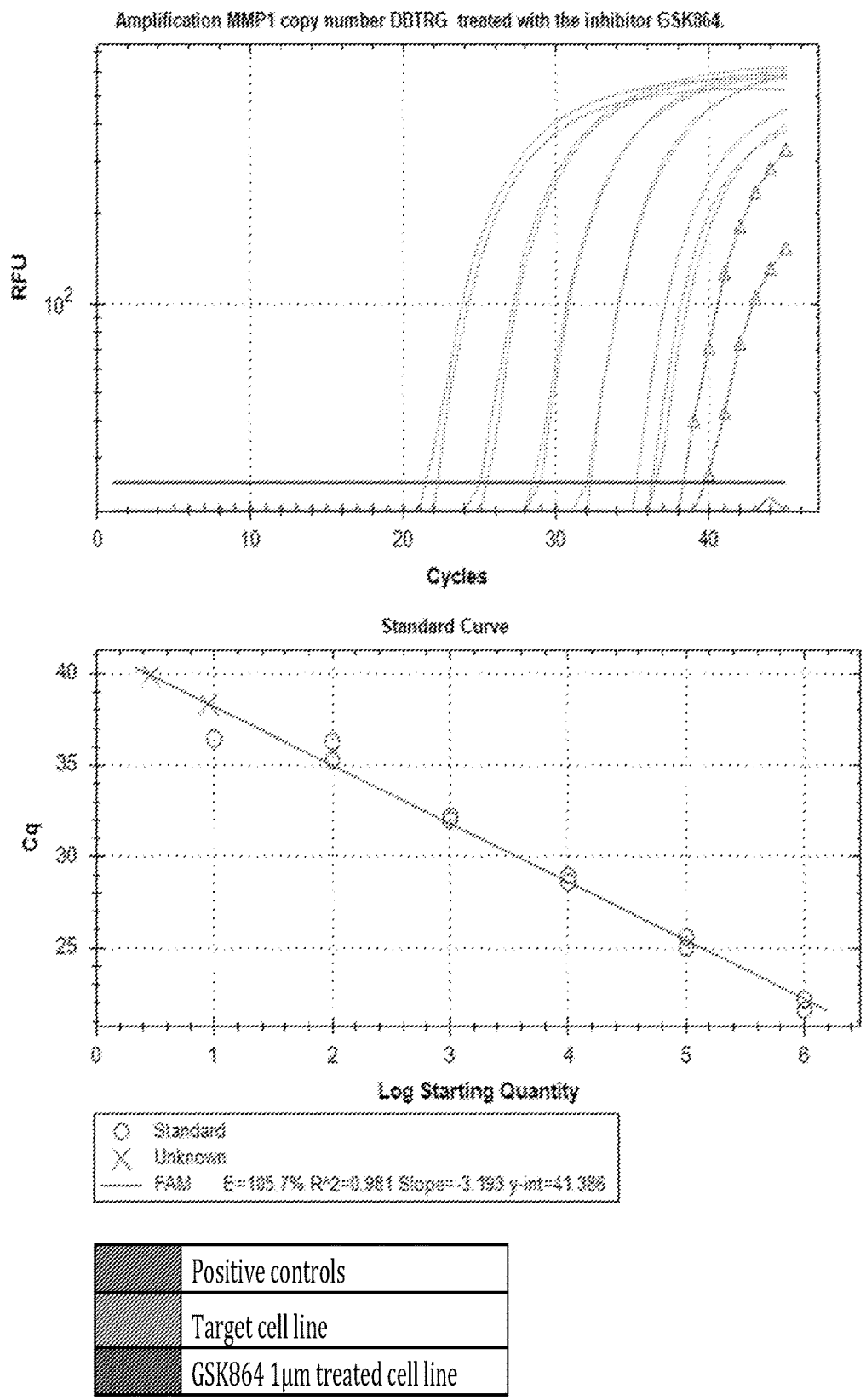
FIGS. 8 and 9 show data relating to therapeutic embodiments.

These cell lines have been treated with the IDH1 inhibitor GSK864 over 24 hrs and 48 hrs. A binary difference is observed in the cell line DBTRG, and quantitative differences in HL60 showing a direct action of the compound on MMP1 chromosome confirmations (see FIG. 8).

| Cell line | Cq | Copy number in 20 ng |
|---|---|---|
| DBTRG 24 hr Ctrl | 39.91101 | 2.898388 |
| DBTRG 24 hr Ctrl | 38.34145 | 8.990504 |
| DBTRG 24 hr Ctrl | NaN | NaN |
| DBTRG 24GSK 1 um | NaN | NaN |
| DBTRG 24GSK 1 um | NaN | NaN |
| DBTRG 24GSK 1 um | NaN | NaN |
| NaN = 0 copies | | |

Figure 9:
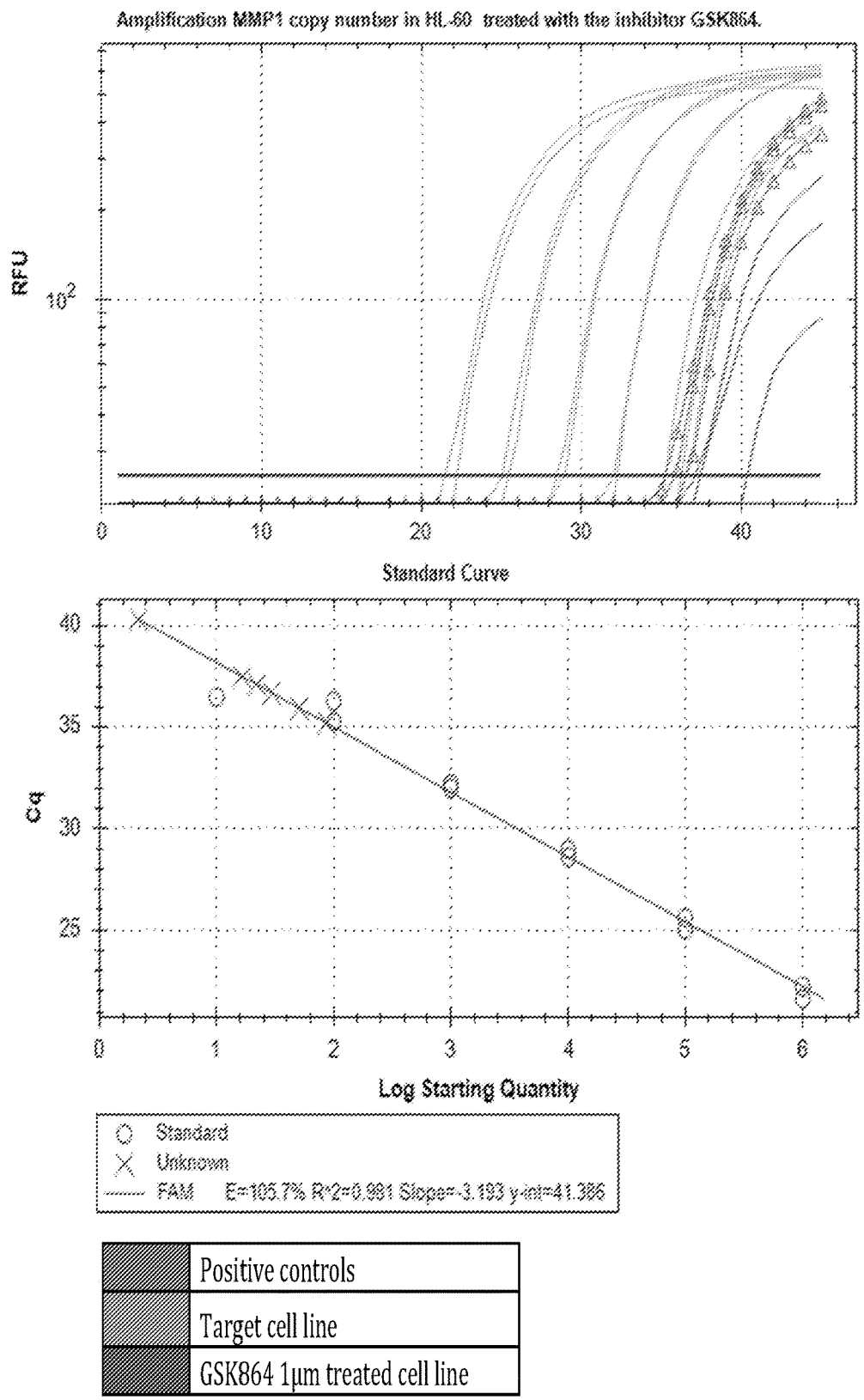

The HL60 cell lines have been treated with the IDH1 inhibitor GSK864 over 24 hrs and 48 hrs. A binary quantitative difference is observed in the 3C MMP1 copy number in the cell line HL60 showing a direct action of the compound on MMP1 chromosome confirmations (see FIG. 9).

| Cell line | Cq | Copy number in 20 ng |
|---|---|---|
| HL-60 48 hr Ctrl | 35.94292 | 50.70651 |
| HL-60 48 hr Ctrl | 35.20558 | 86.30136 |
| HL-60 48 hr Ctrl | 36.69911 | 29.39049 |
| HL-60 48 hr GSK864 | 40.32569 | 2.149149 |
| HL-60 48 hr GSK864 | 37.49586 | 16.54413 |
| HL-60 48 hr GSK864 | 37.10877 | 21.87217 |
| 20 ng = one reaction well. | | |

Summary

These single step assays using SYBR green detection show discrimination between normal blood and malignant material (please see the cell lines described in the tables above). The qPCR 3C copy number can be significantly reduced in the malignant cell lines when compared to normal material (e.g. cKIT and FLT3) or gained e.g. the CCL30 FGFR1 cell line.

The drug imatinib (Glivec: Novartis PLC) is thought to act against the BCR-ABL protein. We demonstrate a direct novel action of imatinib against 3C conformation interactions identified in the gene cKIT. The data shows a direct therapeutic action of imatinib on the 3C conformations.

In addition the GSK864 (an IDH1 mutant inhibitor) shows a direct action on 3C MMP1 copy number at 1 µm in the cell lines DBTRG and HL60.

The invention claimed is:

1. A method of detecting a presence or absence of at least one epigenetic chromosome interaction on a chromosome which relates to one or more genes selected from the group consisting of: FIP1L1, PDGFRA, Flt3, ABL1, FGFR1, cKIT and Bruton tyrosine kinase, (i) wherein the two chromosome regions that form said chromosome interaction may be detected by a probe selected from the group of probes consisting of:

(a) 5'-CTTATAGCCTGTCTCTCTTGCTGATCGAGGTTGCAACGAGCTGAGATTGC-3' (SEQ ID NO: 31)

(b) b'-GGGCCAAGTGTGACTCTCAGGTTTTCGACCTGCCTCAGCCTCCCAAAGT-3' (SEQ ID NO: 35)

(c) 5'-TTGAGGACAAGGACCTCGAGATACTGCCGAGAAATCC-3' (SEQ ID NO: 39)

(d) 5'-TCACCCAGAATAAGGCTTCTCGATTCTAAGTTCTACAAGA-3' (SEQ ID NO: 43)

(e) 5'-AAACCCCAGCAGCCCCTGCCCAAGTCGAGGGAGCAGCTCCCCACCCAGCCC-3' (SEQ ID NO: 49)

(f) 5'-TATGCTTGTGGGACATCGACAAAAGCAATTATGC-3' (SEQ ID NO: 53)

(g) 5'-CCTCGGCGACAGAGTGAGACTCTGTCGATCTCATTCTTTGGTTTCTGAAC-3' (SEQ ID NO: 57)

(h) 5'-ACTTTACTGTGTCCCCATCACGTGTCGACAGAGTCTCACTCTGTCGCCGA-3' (SEQ ID NO: 61)

(i) 5'-GAGTTCAGAAACCAAAGAATGAGATCGAGTGATTGCTAGGTGATGGACCT-3' (SEQ ID NO: 65)

(j) 5'-GCTGGAGGATTGCTTGAGCTTGGGAGGTCGATCTCATTCTTTGGTTTCTGAAC-3' (SEQ ID NO: 69)

(k) 5'-TCAGCAAGGACCTCGAAAAGATAAAACA-3' (SEQ ID NO: 25)

(l) 5'-ATTTATTCGAAAACCCTGGGACCC-3' (SEQ ID NO: 26)

or
(ii) wherein the two chromosome regions that form said chromosome interaction may be detected by a primer pair selected from the group of primer pairs consisting of:

(m) TTCCACGTGGCCTACCACAG (SEQ ID NO: 7) and

CAGCTGCGAGGTTTTCTTTT (SEQ ID NO: 8)

(n) TGGGAGTGGGTGGAGTGAGA (SEQ ID NO: 9) and

ACGGACTGACATCTTTAGCTTCC (SEQ ID NO: 10)

(o) GCAGCTGCGAGGTTTTCTTT (SEQ ID NO: 11) and

GCCATGTGGCTTGGGCATAC (SEQ ID NO: 12)

(p) AGTACTTCCTCTCCCCTCCCA (SEQ ID NO: 13) and

GCAGCTGCGAGGTTTTCTTTT (SEQ ID NO: 14)

(q) CCTCTCCCACACAAACCTGCTA (SEQ ID NO: 15) and

ACATGGAGCACACATACAAGCTAC (SEQ ID NO: 16)

(r) AAATGATGAGGCACGGGTGAA (SEQ ID NO: 17) and

CATGGAGCACACATACAAGCTAC, (SEQ ID NO: 18)

wherein detecting of the chromosome interaction is carried out by determining whether distal regions on a chromosome have come together to form a chromosome interaction, said method comprising the steps of:
(i) in vitro cross-linking of chromosome regions which have come together in a chromosome interaction to form cross-linked nucleic acid;
(ii) subjecting said cross-linked acid to restriction digestion cleavage with an enzyme; and
(iii) ligating said cross-linked cleaved nucleic acid ends to form a ligated product,
wherein determining the presence or absence of the ligated product shows the presence or absence of said chromosome interaction.

2. The method according to claim 1 wherein said determining the presence or absence of said ligated product comprises specific detection of the ligated product by quantitative PCR (qPCR) which uses primers capable of amplifying the ligated product and a probe which binds a ligation site during the PCR reaction, wherein said probe comprises sequence which is complementary to sequence from each of the chromosome regions that have come together in the chromosome interaction.

3. The method according to claim 2 wherein said probe comprises:
   an oligonucleotide which specifically binds to said ligated product, and/or
   a fluorophore covalently attached to the 5' end of the oligonucleotide, and/or
   a quencher covalently attached to the 3' end of the oligonucleotide, and
   optionally said fluorophore is selected from HEX, Texas Red and FAM.

4. The method according to claim 1 which is carried out to determine prognosis or therapy for any of the following cancers:
   (a) idiopathic hypereosinophilic syndrome (iHES)
   (b) chronic and acute eosinophilic leukemias
   (c) acute myeloid leukemia (AML)
   (d) PDGFRA positive non-small cell lung carcinoma
   (e) glioblastoma, including glioblastoma multiforme and astrocytoma
   (f) prostate cancer
   (g) advanced ovarian cancer
   (h) gastrointestinal stromal tumour (GIST).

5. The method according to claim 1 further comprising administering a therapeutic agent, optionally a tyrosine kinase inhibitor, for treatment and/or prophylaxis of a cancer in an individual based on the detection of the presence or absence of the chromosome interaction.

6. A method for quantitatively detecting a ligated sequence which is relevant to a chromosome interaction using a probe which is detectable upon activation during a PCR reaction,
   wherein said ligated sequence comprises sequences from two chromosome regions that come together in an epigenetic chromosome interaction,
   wherein said method comprises contacting the ligated sequence with the probe during a PCR reaction, and detecting the extent of activation of the probe, and
   wherein said probe binds a ligation site, and
   the ligated sequence is a ligated product made by the method of claim 1.

* * * * *